(12) United States Patent
Dixon et al.

(10) Patent No.: US 10,634,680 B2
(45) Date of Patent: Apr. 28, 2020

(54) TARGET-BINDING ACTIVATED SPLIT REPORTER SYSTEMS FOR ANALYTE DETECTION AND RELATED COMPONENTS AND METHODS

(71) Applicant: UNIVERSITY OF UTAH RESEARCH FOUNDATION, Salt Lake City, UT (US)

(72) Inventors: Andrew S. Dixon, Salt Lake City, UT (US); Shawn Owen, Salt Lake City, UT (US); Julio C. Delgado, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 207 days.

(21) Appl. No.: 15/498,291

(22) Filed: Apr. 26, 2017

(65) Prior Publication Data

US 2018/0172692 A1    Jun. 21, 2018

Related U.S. Application Data

(60) Provisional application No. 62/327,920, filed on Apr. 26, 2016.

(51) Int. Cl.

| | | |
|---|---|---|
| *G01N 33/574* | (2006.01) | |
| *C12Q 1/66* | (2006.01) | |
| *G01N 33/58* | (2006.01) | |
| *G01N 33/542* | (2006.01) | |
| *C07K 16/24* | (2006.01) | |
| *C12Q 1/6804* | (2018.01) | |

(52) U.S. Cl.
CPC ..... *G01N 33/57488* (2013.01); *C07K 16/241* (2013.01); *C12Q 1/66* (2013.01); *G01N 33/542* (2013.01); *G01N 33/581* (2013.01); *C07K 2317/24* (2013.01); *C12Q 1/6804* (2013.01); *G01N 2333/525* (2013.01)

(58) Field of Classification Search
None
See application file for complete search history.

(56) References Cited

U.S. PATENT DOCUMENTS

| | | | |
|---|---|---|---|
| 4,975,278 A | 12/1990 | Senter et al. | |
| 5,256,395 A | 10/1993 | Barbet et al. | |
| 5,837,242 A | 11/1998 | Hollinger et al. | |
| 6,077,499 A | 6/2000 | Griffiths et al. | |
| 7,335,478 B2 | 2/2008 | Balint et al. | |
| 7,544,477 B2 | 6/2009 | Balint et al. | |
| 7,833,528 B2 | 11/2010 | Griffiths et al. | |
| 8,623,356 B2 | 1/2014 | Christopherson et al. | |
| 2006/0257406 A1 | 11/2006 | Winter et al. | |
| 2008/0248463 A1 | 10/2008 | Weiss et al. | |
| 2010/0291543 A1* | 11/2010 | De Las Heras | C12N 9/86 435/5 |
| 2013/0004981 A1 | 1/2013 | Chiang et al. | |
| 2013/0344094 A1 | 12/2013 | Gerg et al. | |
| 2014/0011214 A1 | 1/2014 | McNaughton et al. | |
| 2014/0271687 A1 | 9/2014 | Kovesdi et al. | |
| 2014/0363375 A1 | 12/2014 | Dixon et al. | |
| 2015/0079093 A1 | 3/2015 | Stuhler | |

FOREIGN PATENT DOCUMENTS

| | | |
|---|---|---|
| WO | 2012061530 | 5/2012 |
| WO | 2013126962 | 9/2013 |
| WO | 2014151736 | 9/2014 |

OTHER PUBLICATIONS

Jamieson et al. (J. Immunological Methods 2009 vol. 345, p. 106-111). (Year: 2009).*
Franciotta et al. (Clinical Chem. 1999 vol. 45. page (Year: 1999).*
Ben-Horin et al. (J. Crohn's and Colitis 2011 vol. 5, p. 555-558). (Year: 2011).*
Di Gioia, et al., "Serum HER2 supports HER2-testing in tissue at the time of primary diagnosis of breast cancer", Clinica Chimica Acta, 430, 2014, pp. 86-91.
Engvall, et al., "Enzyme-linked immunosorbent assay (ELISA) Quantiative assay of immunoglobulin G", IMM vol. 8, No. 9, 1971, pp. 871-874.
Remy, et al., "A highly sensitive protein-protein interaction assay based on Gaussia Luciferase", Nature Methods, vol. 3, No. 12, Dec. 2006, pp. 977-979.
Shekhawat, et al., "Split-protein systems: beyond binary protein-protein interactions", Current Opinion in Chemical Biology, 15, 2011, pp. 789-797.
Armbruster, et al., "Limit of Bank, Limit of Detection and Limit of Quantitation", Clin. Biochem. Rev., vol. 29 Suppl. (i), Aug. 2008, pp. S49-S52.
Backer, et al., "Self-Assembled "Dock and Lock" System for Linking Payloads to Targeting Proteins", Bioconjugate Chem. 17, 2006, pp. 912-919.
Cabantous, et al., "A New Protein-Protein Interaction Sensor Based on Tripartite Split-GFP Association", Scientific Reports, 3 : 2854, Oct. 4, 2013, 9 pages.
Carter, et al., "Humanization of an anti-p185HER2 antibody for human cancer therapy", Proc. Natl. Acad. Sci. USA, vol. 89, May 1992, pp. 4285-4289.
Cho, et al., "Structure of the extracellular region of HER2 alone and in complex with the Herceptin Fab", Nature, vol. 421, Feb. 13, 2003, pp. 756-760.

(Continued)

*Primary Examiner* — Changhwa J Cheu
(74) *Attorney, Agent, or Firm* — Michael Best & Friedrich LLP

(57) ABSTRACT

Split enzyme reporter systems are disclosed for detecting an analyte in a mixture. Fragments of the split enzyme may be covalently bound to targeting domains that bind to target regions of an analyte, thereby causing formation of an active complex. Some split enzyme reporter systems can be used to detect an analyte without the use of analyte immobilization, blocking, or wash steps. Some reporter systems also enable rapid detection of the analyte of interest.

20 Claims, 37 Drawing Sheets
Specification includes a Sequence Listing.

(56) References Cited

OTHER PUBLICATIONS

Dixon, et al., "NanoLuc Complementation Report Optimized for Accurate Measurement of Protein Interactions in Cells", ACS Chem. Biol. 11, 2016, pp. 400-408.
Dixon, et al., "NanoLuc Complementation Reporter Optimized for Accurate Measurement of Protein Interactions in Cells", 33 pages.
Eigenbrot, et al., "Structural basis for high-affinity HEr2 receptor binding by an engineered protein", PNAS, vol. 107, No. 34, Aug. 24, 2010, pp. 15039-15044.
EPA, "Structural Model for the Interaction of a Designed Ankyrin Repeat Protein with the Human Epidermal Growth Factor Receptor 2", PLOS One, vol. 8, Issue 3, Mar. 2013, pp. 1-10.
Esteva, et al., "Clinical utility of serum HER2/neu in monitoring and predicition of prograssion-free survival in metastatic breast cancer patients treated with trastuzumab-based therapies", Breast Cancer Research; 7, 2005, pp. R436-R443.
Fisher, et al., "Structure of the Complex between HER2 and an Antibody Paratope Formed by Side Chains from Tryptophan and Serine", J. Mol. Biol.; 402, 2010, pp. 217-229.
Franklin, et al., "Insights into ErbB signaling from the structure of the ErbB2-pertuzumab complex", Cancer Cell, vol. 5, Apr. 2004, pp. 317-328.
Girish, et al., "Clinical pharmacology of trastuzumab emtansine (T-DM1): an anti-body-drug conjugate in development for the treatment of HER2-positive cancer", Cancer Chemother Pharmacol 69, 2012, pp. 1229-1240.
Hall, et al., "Engineered Luciferase Reporter from a Deep Sea Shrimp Utilizing a Novel Imidazopyrazinone Substrate", ACS Chem. Biol. 7, 2012, pp. 1848-1857.
Hechtman, et al., "HER2/neu Gene Amplification and Protein Overexpression in Gastric and Gastroesophageal Junction Adenocarcinoma", Arch Pathol Lab Med, vol. 136, Jun. 2012, pp. 691-697.
Heinmoller, et al., "HER2 Status in Non-Small Cell Lung Cancer: Results from Patient Screening for Enrollment to a Phase II Study of Herceptin", Clinical Cancer Research, vol. 9, Nov. 1, 2003, pp. 5238-5244.
Hooper, Ph.D., "Application of a smaller, brighter, more versatile luciferase", Nanoluc (TM) Luciferase Technology, Fall 2012, 41 pages.
Jorgensen, "Role of human epidermal growth factor receptor 2 in gastric cancer: Biological and pharmacological aspects", World J Gastroenterol 20(16), Apr. 28, 2014, pp. 4526-4535.
Jost, et al., "Structural Basis for Eliciting a Cytotoxic Effect in HER2-Overexpressing Cancer Cells via Binding to the Extracellular Domain of HER2", Structure; 21, Nov. 5, 2013, pp. 1979-1991.
Kerppola, "Visualization of molecular interactions using bimolecular fluorescence complementation analysis: Characteristics of protein fragment complementation", Chem. Soc. Rev., 38, 2009, pp. 2876-2886.
Kurebayashi, "Biological and Clinical Significane of HER2 Overexpression in Breast Cancer", Breast Cancer, vol. 8, No. 1, Jan. 2001, pp. 45-51.
Lewis, et al., "Generation of bispecific IgG antibodies by structure-based design of an orthogonal Fab interface", Nature Biotechnology, vol. 32, No. 2, Feb. 2014, pp. 191-202.
Lorusso, et al., "Trastuzumab Emtansine: A Unique Antibody-Drug Conjugate in Development for Human Epidermal Growth Factor Receptor 2-Positive Cancer", Clinical Cancer Research 17 (20), Oct. 15, 2011, pp. 6437-6447.
Luker, et al., "Kinetics of regulated protein-protein interactions revealed with firefly luciferase complementation imaging in cells and living animals", PNAS, vol. 101, No. 33, Aug. 17, 2004, pp. 12288-12293.
McAlpine, et al., "HER2 overexpression and amplification is present in a subset of ovarian mucinous carcinomas and can be targeted with trastuzumab therapy", BMC Cancer 9:433, Dec. 10, 2009, 12 pages.
Menard, et al., "Role of HER2 Gene Overexpression in Breast Carcinoma", Journal of Cellular Physiology 182, 2000, pp. 150-162.
Miller, et al., "Bimolecular Fluorescence Complementation (BiFC) Analysis: Advances with Recent Applications for Gene-Wide Interaction Studies", J Mol Biol 427, 2015, pp. 2039-2055.
Ohmuro-Matsuyama, et al., "Demonstration of protein-fragment complementation assay using protein firefly luciferase fragments", BMC Biotechnology, 13:31, 2013, 9 pages.
Owen, et al., "Targeting HER2 + breast cancer cells: Lysosomal accumulation of anti-HER2 antibodies is influenced by antibody binding site and conjugation to polymeric nanoparticles", Journal of Controlled Release; 172, 2013, pp. 395-404.
Paulmurugan, et al., "Monitoring Protein—Protein Interactions Using Split Synthetic Renilla Luciferase Protein-Fragment-Assisted Complementation", Analytical Chemistry, vol. 75, No. 7, Apr. 1, 2003, pp. 1584-1589.
Pegram, et al., "Phase II Study of Receptor-Enhanced Chemosensitivity Using Recombinant Humanized Anti-p185HER2/neu Monoclonal Antibody Plus Cisplatin in Patients With HER2/neu-Overexpressing Metastatic Breast Cancer Refractory to Chemotherapy Treatment", Journal of Clinical Oncology, vol. 16, No. 8, Aug. 1998, pp. 2659-2671.
Phillips, et al., "Targeting HER2-Positive Breast Cancer with Trastuzumab-DM1, an Antibody-Cytotoxic Drug Conjugate", Cancer Research 2008; 68: (22), Nov. 15, 2008, 12 pages.
Plosker, et al., "Trastuzumab: A Review of its Use in the Management of HER2-Positive Metastatic and Early-Stage Breast Cancer", Drugs; 66(4), 2006, pp. 449-475.
Ross, et al., "Targeted Therapy in Breast Cancer", Molecular & Cellular Proteomics 3.4, 2004, pp. 379-398.
Ross, et al., "The HER-2/neu Gene and Protein in Breast Cancer 2003: Blomarker and Target of Therapy", The Oncologist; 8, 2003, pp. 307-325.
Santin, et al., "Overexpression of HER-2/Neu in Uterine Serous Papillary Cancer", Clinical Cancer Research, vol. 8, May 2002, pp. 1271-1279.
Stains, et al., "A General Approach for Receptor and Antibody-Targeted Detection of Native Proteins Utilizing Split-Luciferase Resassembly", ACS Chemical Biology, vol. 5, No. 10, 2010, pp. 943-952.
Teplinksky, et al., "Targeting HER2 in ovarian and uterine cancers: Challenges and future directions", Gynecologic Oncology 135, 2014, pp. 364-370.
Tinghe, et al., "ELISA in the multiplex era: Potentials and pitfalls", Proteomics Clin. Appl. 9, 2015, pp. 406-422.
Todeschini, et al., "Her2/neu extracellular domain shedding in uterine serous carcinoma: implications for immunotherapy with trastuzumab", British Journal of Cancer; 105, 2011, pp. 1176-1182.
Tse, et al., "HEr2 shedding and serum HER2 extracellular domain: Biology and clinical utility in breast cancer", Cancer Treatment Reviews; 38, 2012, pp. 133-142.
Van Weemen, et al., "Immunoassay Using Antigen—Enzyme Conjugates", FEBS Letters vol. 5, No. 3, Jun. 1971, 5 pages.
Walshe, et al., "A Phase II Trial with Trastuzumab and Pertuzumab in Patients with HEr2-Overexpressed Locally Advanced and Metastatic Breast Cancer", Clinical Breast Cancer, vol. 6, No. 6, 2006, pp. 535-539.
Wesola, et al., "A Comparison of IHC and FISH Cytogenic Methods in the Evaluation of HER2 Status in Breast Cancer", Adv Clin Exp Med; 24, 2015, pp. 899-904.
Witzell, et al., "Monitoring serum HER2 levels during neoadjuvant trastuzumab treatment within the GeparQuattro trial", Breast Cancer Res Treat; 123, 2010, pp. 437-445.
Yu, et al., "Overexpression of ErbB2 in cancern and ErbB2-targeting strategies", Oncogene; 19, 2000, pp. 6115-6121.
Zahnd, et al., "A Desined Ankyrin Repeat Protein Evolved to Picomolar Affinity to Her2", J. Mol. Biol.; 369, 2007, pp. 1015-1028.
Zhou, et al., "Structural Insights into the Down-regulation of Overexpressed p185her2/neu Protein of Transformed Cells by the Antibody chA21", Journal of Biological Chemistry, vol. 286, No. 36, Sep. 9, 2011, pp. 31676-31683.

(56) References Cited

OTHER PUBLICATIONS

International Search Report and Written Opinion for Application No. PCT/US2017/029680 dated Sep. 18, 2017 (17 pages).
Nesbitt et al., "Mechanism of action of certolizumab pegol (CDP870): in vitro comparison with other anti-tumor necrosis factor alpha agents," Inflammatory Bowel Diseases, 2011, 13(11): 1323-1332.
Tsien, "The Green Fluorescent Protein," Annual Review of Biochemistry, 1998, vol. 67, pp. 509-544.
Yan et al., "Indexing TNF-α gene expression using a gene-targeted reporter cell line," BMC Biology, 2009, 7(8): 1-10.

* cited by examiner

SEQUENCE LISTING

<160> NUMBER OF SEQ ID NOS: 96

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 1

Val Ser Gly Trp Arg Leu Phe Lys Lys Ile Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 2

Gly Ser Met Leu Phe Arg Val Thr Ile Asn Ser
1               5                   10

<210> SEQ ID NO 3
<211> LENGTH: 148
<212> TYPE: PRT
<213> ORGANISM: Artificial Sequence
<220> FEATURE:
<223> OTHER INFORMATION: synthetic polypeptide

<400> SEQUENCE: 3

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
                20                  25                  30

Leu Gln Asn Leu Ala Val Ser Val Thr Pro Ile Gln Arg Ile Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp
145

<210> SEQ ID NO 4

```
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 4

Gly Gly Gly Ser Gly His His His His His His His Gly Gly Gly
1               5                   10                  15

Ser Gly

<210> SEQ ID NO 5
<211> LENGTH: 1549
<212> TYPE: DNA
<213> ORGANISM: Artificial Sequence
<220> FEATURE:
<223> OTHER INFORMATION: beta-9-L73J (light chain) nucleotide sequence

<400> SEQUENCE: 5
atgggtagta tgctgtttcg tgttaccatt aacagcggtg gtggtagcgg tcatcatcac      60
caccatcacc atcatggtgg tggcagtggt atggcaagcg atattcagat gacccagagc     120
ccgagcagcc tgagcgcaag cgttggtgat cgtgttacca ttacctgtcg tgcaagccag     180
agcgttagca gcgcggttgc atggtatcag cagaaaccgg gtaaagcacc gaaactgctg     240
atttatagcg caagcagcct gtatagcggt gttccgagcc gttttagcgg tagccgtagc     300
ggcaccgatt ttaccctgac cattagcagc ctgcagccgg aagattttgc aacctattat     360
tgtcagcagg gctattatta cccgtttacc tttggtcagg gcaccaaagt tgaaattaaa     420
cgtaccgttg cagcaccgag cgtttttatc tttccgccta gcgatagcca gctgaaaagc     480
ggtacagcca gcgttgtttg tctgctgaat aactttatc cgcgtgaagc aaaagttcag     540
tggaaagttg ataatgcact gcagagcggt aatagccaag aaagcgttac cgaacaggat     600
agcaaagata gcacctatag cctgagcagc accctgaccc tgagcaaagc agattatgaa     660
aaacacaaag tgtatgcctg cgaagttacc catcagggtc tgagcagtcc ggttaccaaa     720
agctttaatc gtggtgaatg ttaattaact cgaggctgag caaagcagac tactaataac     780
ataaagtcta cgccggacgc atcgtggccc tagtacgcaa gttcacgtaa aagggtaac     840 tagaggttga ggtgatttta tggaaattag cgaagttcag ctggttgaaa gcggtggtgg     900
tctggttcag cctggtggta gcctgcgtct gagctgtgca gcaagcggtt ttaatctgta     960
tagcagctat attcattggg ttcgtcaggc accgggtaaa ggtctggaat gggttgcaag    1020
catttatccg tatagctcat ataccagcta tgccgatagc gttaaaggtc gttttaccat    1080
tagcgcagat accagcaaaa ataccgcata cctgcagatg aatagtctgc gtgcagagga    1140
taccgcagtg tattattgtg cacgttatta tggtttcgcc atggattatt ggggtcaggg    1200
caccctggtt accgttagca gcgcaagcac caaaggtccg agcgtttttc cgctggcacc    1260
gagcagcaaa agcaccagcg gtggcaccgc agcactgggt tgtctggtta agattattt    1320 tccggaaccg gttaccgtga gctggaatag cggtgcactg accagtggtg ttcataccct    1380
tccggcagtt ctgcagagca gcggtctgta tagtctgagc agcgttgtta ccgttccgag    1440
cagtagcctg ggcacccaga cctatatttg taatgttaat cataaaccga gcaacaccaa    1500
agtggataaa aaagttgaac gaaaagctg cgataaaacc catacctaa               1549

<210> SEQ ID NO 6
<211> LENGTH: 247
<212> TYPE: PRT
```

<213> ORGANISM: Artificial Sequence
<220> FEATURE:
<223> OTHER INFORMATION: Beta9-His Tag-light chain

<400> SEQUENCE: 6

```
Met Gly Ser Met Leu Phe Arg Val Thr Ile Asn Ser Gly Gly Ser
1               5                   10                  15

Gly His His His His His His His Gly Gly Gly Ser Gly Met Ala
                20                  25                  30

Ser Asp Ile Gln Met Thr Gln Ser Pro Ser Ser Leu Ser Ala Ser Val
            35                  40                  45

Gly Asp Arg Val Thr Ile Thr Cys Arg Ala Ser Gln Ser Val Ser Ser
    50                  55                  60

Ala Val Ala Trp Tyr Gln Gln Lys Pro Gly Lys Ala Pro Lys Leu Leu
65                  70                  75                  80

Ile Tyr Ser Ala Ser Ser Leu Tyr Ser Gly Val Pro Ser Arg Phe Ser
                85                  90                  95

Gly Ser Arg Ser Gly Thr Asp Phe Thr Leu Thr Ile Ser Ser Leu Gln
            100                 105                 110

Pro Glu Asp Phe Ala Thr Tyr Tyr Cys Gln Gln Gly Tyr Tyr Tyr Pro
        115                 120                 125

Phe Thr Phe Gly Gln Gly Thr Lys Val Glu Ile Lys Arg Thr Val Ala
130                 135                 140

Ala Pro Ser Val Phe Ile Phe Pro Pro Ser Asp Ser Gln Leu Lys Ser
145                 150                 155                 160

Gly Thr Ala Ser Val Val Cys Leu Leu Asn Asn Phe Tyr Pro Arg Glu
                165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
    210                 215                 220

Tyr Ala Cys Glu Val Thr His Gln Gly Leu Ser Ser Pro Val Thr Lys
225                 230                 235                 240

Ser Phe Asn Arg Gly Glu Cys
                245
```

<210> SEQ ID NO 7
<211> LENGTH: 229
<212> TYPE: PRT
<213> ORGANISM: Artificial Sequence
<220> FEATURE:
<223> OTHER INFORMATION: heavy chain

<400> SEQUENCE: 7

```
Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
                20                  25                  30

Leu Tyr Ser Ser Tyr Ile His Trp Val Arg Gln Ala Pro Gly Lys Gly
            35                  40                  45

Leu Glu Trp Val Ala Ser Ile Tyr Pro Tyr Ser Ser Tyr Thr Ser Tyr
    50                  55                  60

Ala Asp Ser Val Lys Gly Arg Phe Thr Ile Ser Ala Asp Thr Ser Lys
65                  70                  75                  80
```

```
Asn Thr Ala Tyr Leu Gln Met Asn Ser Leu Arg Ala Glu Asp Thr Ala
             85                  90                  95

Val Tyr Tyr Cys Ala Arg Tyr Tyr Gly Phe Ala Met Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225
```

<210> SEQ ID NO 8
<211> LENGTH: 1549
<212> TYPE: DNA
<213> ORGANISM: Artificial Sequence
<220> FEATURE:
<223> OTHER INFORMATION: Beta10*-L73J

<400> SEQUENCE: 8

```
atggtgagcg gttggcgtct gttcaaaaaa atcagcggtg gtggtagcgg tcatcatcac    60
caccatcacc atcatggtgg tggcagtggt atggcaagcg atattcagat gacccagagc   120
ccgagcagcc tgagcgcaag cgttggtgat cgtgttacca ttacctgtcg tgcaagccag   180
agcgttagca gcgcggttgc atggtatcag cagaaaccgg gtaaagcacc gaaactgctg   240
atttatagcg caagcagcct gtatagcggt gttccgagcc gttttagcgg tagccgtagc   300
ggcaccgatt ttaccctgac cattagcagc ctgcagccgg aagattttgc aacctattat   360
tgtcagcagg gctattatta cccgtttacc tttggtcagg gcaccaaagt tgaaattaaa   420
cgtaccgttg cagcaccgag cgtttttatc tttccgccta gcgatagcca gctgaaaagc   480
ggtacagcca gcgttgtttg tctgctgaat aacttttatc cgcgtgaagc aaaagttcag   540
tggaaagttg ataatgcact gcagagcggt aatagccaag aaagcgttac cgaacaggat   600
agcaaagata gcacctatag cctgagcagc acccctgaccc tgagcaaagc agattatgaa   660
aaacacaaag tgtatgcctg cgaagttacc catcagggtc tgagcagtcc ggttaccaaa   720
agctttaatc gtggtgaatg ttaattaact cgaggctgag caaagcagac tactaataac   780
ataaagtcta cgccggacgc atcgtggccc tagtacgcaa gttcacgtaa aaagggtaac   840
tagaggttga ggtgatttta tggaaattag cgaagttcag ctggttgaaa gcggtggtgg   900
tctggttcag cctggtggta gcctgcgtct gagctgtgca gcaagcggtt ttaatctgta   960
tagcagctat attcattggg ttcgtcaggc accgggtaaa ggtctggaat gggttgcaag  1020
catttatccg tatagctcat ataccagcta tgccgatagc gttaaaggtc gttttaccat  1080
tagcgcagat accagcaaaa ataccgcata cctgcagatg aatagtctgc gtgcagagga  1140
taccgcagtg tattattgtg cacgttatta tggtttcgcc atggattatt ggggtcaggg  1200
```

```
cacccctggtt accgttagca gcgcaagcac caaaggtccg agcgtttttc cgctggcacc   1260
gagcagcaaa agcaccagcg gtggcaccgc agcactgggt tgtctggtta aagattattt   1320
tccggaaccg gttaccgtga gctggaatag cggtgcactg accagtggtg ttcatacctt   1380
tccggcagtt ctgcagagca gcggtctgta tagtctgagc agcgttgtta ccgttccgag   1440
cagtagcctg gcacccaga cctatatttg taatgttaat cataaaccga gcaacaccaa   1500
agtggataaa aaagttgaac cgaaaagctg cgataaaacc catacctaa              1549
```

<210> SEQ ID NO 9
<211> LENGTH: 247
<212> TYPE: PRT
<213> ORGANISM: Artificial Sequence
<220> FEATURE:
<223> OTHER INFORMATION: Beta10*-His Tag-light chain

<400> SEQUENCE: 9

```
Met Val Ser Gly Trp Arg Leu Phe Lys Lys Ile Ser Gly Gly Gly Ser
1               5                   10                  15

Gly His His His His His His His Gly Gly Gly Ser Gly Met Ala
                20                  25                  30

Ser Asp Ile Gln Met Thr Gln Ser Pro Ser Ser Leu Ser Ala Ser Val
            35                  40                  45

Gly Asp Arg Val Thr Ile Thr Cys Arg Ala Ser Gln Ser Val Ser Ser
        50                  55                  60

Ala Val Ala Trp Tyr Gln Gln Lys Pro Gly Lys Ala Pro Lys Leu Leu
65                  70                  75                  80

Ile Tyr Ser Ala Ser Ser Leu Tyr Ser Gly Val Pro Ser Arg Phe Ser
                85                  90                  95

Gly Ser Arg Ser Gly Thr Asp Phe Thr Leu Thr Ile Ser Ser Leu Gln
            100                 105                 110

Pro Glu Asp Phe Ala Thr Tyr Tyr Cys Gln Gln Gly Tyr Tyr Tyr Pro
        115                 120                 125

Phe Thr Phe Gly Gln Gly Thr Lys Val Glu Ile Lys Arg Thr Val Ala
    130                 135                 140

Ala Pro Ser Val Phe Ile Phe Pro Pro Ser Asp Ser Gln Leu Lys Ser
145                 150                 155                 160

Gly Thr Ala Ser Val Val Cys Leu Leu Asn Asn Phe Tyr Pro Arg Glu
                165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
    210                 215                 220

Tyr Ala Cys Glu Val Thr His Gln Gly Leu Ser Ser Pro Val Thr Lys
225                 230                 235                 240

Ser Phe Asn Arg Gly Glu Cys
                245
```

<210> SEQ ID NO 10
<211> LENGTH: 229
<212> TYPE: PRT
<213> ORGANISM: Artificial Sequence
<220> FEATURE:
<223> OTHER INFORMATION: heavy chain

<400> SEQUENCE: 10

```
Met Glu Ile Ser Glu Val Gln Leu Val Glu Ser Gly Gly Gly Leu Val
1               5                   10                  15
Gln Pro Gly Gly Ser Leu Arg Leu Ser Cys Ala Ala Ser Gly Phe Asn
            20                  25                  30
Leu Tyr Ser Ser Tyr Ile His Trp Val Arg Gln Ala Pro Gly Lys Gly
        35                  40                  45
Leu Glu Trp Val Ala Ser Ile Tyr Pro Tyr Ser Tyr Thr Ser Tyr
    50                  55                  60
Ala Asp Ser Val Lys Gly Arg Phe Thr Ile Ser Ala Asp Thr Ser Lys
65                  70                  75                  80
Asn Thr Ala Tyr Leu Gln Met Asn Ser Leu Arg Ala Glu Asp Thr Ala
                85                  90                  95
Val Tyr Tyr Cys Ala Arg Tyr Tyr Gly Phe Ala Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr
225
```

<210> SEQ ID NO 11
<211> LENGTH: 1546
<212> TYPE: DNA
<213> ORGANISM: Artificial Sequence
<220> FEATURE:
<223> OTHER INFORMATION: 73JH-Beta9

<400> SEQUENCE: 11

```
atggcaagcg atattcagat gacccagagc ccgagcagcc tgagcgcaag cgttggtgat      60
cgtgttacca ttacctgtcg tgcaagccag agcgttagca gcgcggttgc atggtatcag     120
cagaaaccgg gtaaagcacc gaaactgctg atttatagcg caagcagcct gtatagcggt     180
gttccgagcc gttttagcgg tagccgtagc ggcaccgatt ttaccctgac cattagcagc     240
ctgcagccgg aagattttgc aacctattat tgtcagcagg ctattatta cccgtttacc     300
tttggtcagg gcaccaaagt tgaaattaaa cgtaccgttg cagcaccgag cgtttttatc     360
tttccgccta gcgatagcca gctgaaaagc ggtacagcca gcgttgtttg tctgctgaat     420
aactttttatc gcgtgaagc aaaagttcag tggaaagttg ataatgcact gcagagcggt     480
aatagccaag aaagcgttac cgaacaggat agcaaagata gcacctatag cctgagcagc     540
accctgaccc tgagcaaagc agattatgaa aaacacaaag tgtatgcctg cgaagttacc     600
catcagggtc tgagcagtcc ggttaccaaa agctttaatc gtggtgaatg ttaattaact     660
```

```
cgaggctgag caaagcagac tactaataac ataaagtcta cgccggacgc atcgtggccc    720
tagtacgcaa gttcacgtaa aaagggtaac tagaggttga ggtgatttta tggaaattag    780
cgaagttcag ctggttgaaa gcggtggtgg tctggttcag cctggtggta gcctgcgtct    840
gagctgtgca gcaagcggtt ttaatctgta tagcagctat attcattggg ttcgtcaggc    900
accgggtaaa ggtctggaat gggttgcaag catttatccg tatagctcat ataccagcta    960
tgccgatagc gttaaaggtc gttttaccat tagcgcagat accagcaaaa ataccgcata   1020
cctgcagatg aatagtctgc gtgcagagga taccgcagtg tattattgtg cacgttatta   1080
tggtttcgcc atggattatt ggggtcaggg caccctggtt accgttagca gcgcaagcac   1140
caaaggtccg agcgttttc cgctggcacc gagcagcaaa agcaccagcg gtggcaccgc   1200
agcactgggt tgtctggtta aagattattt tccggaaccg gttaccgtga gctggaatag   1260
cggtgcactg accagtggtg ttcatacctt tccggcagtt ctgcagagca gcggtctgta   1320
tagtctgagc agcgttgtta ccgttccgag cagtagcctg gcacccaga cctatatttg   1380 taatgttaat cataaaccga gcaacaccaa agtggataaa aaagttgaac cgaaaagctg   1440
cgataaaacc cataccggtg gtggtagcgg tcatcatcac caccatcacc atcatggtgg   1500
tggcagtggt ggtagtatgc tgtttcgtgt taccattaac agctaa                 1546
```

<210> SEQ ID NO 12
<211> LENGTH: 217
<212> TYPE: PRT
<213> ORGANISM: Artificial Sequence
<220> FEATURE:
<223> OTHER INFORMATION: light chain

<400> SEQUENCE: 12

Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Ser Val
            20                  25                  30

Ser Ser Ala Val Ala Trp Tyr Gln Gln Lys Pro Gly Lys Ala Pro Lys
        35                  40                  45

Leu Leu Ile Tyr Ser Ala Ser Ser Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln Gly Tyr Tyr
                85                  90                  95

Tyr Pro Phe Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

```
Thr Lys Ser Phe Asn Arg Gly Glu Cys
    210                 215
```

<210> SEQ ID NO 13
<211> LENGTH: 258
<212> TYPE: PRT
<213> ORGANISM: Artificial Sequence
<220> FEATURE:
<223> OTHER INFORMATION: heavy chain-His Tag-Beta9

<400> SEQUENCE: 13

```
Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
            20                  25                  30

Leu Tyr Ser Ser Tyr Ile His Trp Val Arg Gln Ala Pro Gly Lys Gly
        35                  40                  45

Leu Glu Trp Val Ala Ser Ile Tyr Pro Tyr Ser Ser Tyr Thr Ser Tyr
    50                  55                  60

Ala Asp Ser Val Lys Gly Arg Phe Thr Ile Ser Ala Asp Thr Ser Lys
65                  70                  75                  80

Asn Thr Ala Tyr Leu Gln Met Asn Ser Leu Arg Ala Glu Asp Thr Ala
                85                  90                  95

Val Tyr Tyr Cys Ala Arg Tyr Tyr Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Gly Gly Gly Ser Gly His His His His His His
225                 230                 235                 240

His His Gly Gly Gly Ser Gly Gly Ser Met Leu Phe Arg Val Thr Ile
                245                 250                 255

Asn Ser
```

<210> SEQ ID NO 14
<211> LENGTH: 1546
<212> TYPE: DNA
<213> ORGANISM: Artificial Sequence
<220> FEATURE:
<223> OTHER INFORMATION: 73JH-Beta10*

<400> SEQUENCE: 14

```
atggcaagcg atattcagat gacccagagc ccgagcagcc tgagcgcaag cgttggtgat      60
cgtgttacca ttacctgtcg tgcaagccag agcgttagca gcgcggttgc atggtatcag     120
cagaaaccgg gtaaagcacc gaaactgctg atttatagcg caagcagcct gtatagcggt     180
```

```
gttccgagcc gttttagcgg tagccgtagc ggcaccgatt ttaccctgac cattagcagc    240
ctgcagccgg aagattttgc aacctattat tgtcagcagg gctattatta cccgtttacc    300
tttggtcagg gcaccaaagt tgaaattaaa cgtaccgttg cagcaccgag cgtttttatc    360
tttccgccta gcgatagcca gctgaaaagc ggtacagcca gcgttgtttg tctgctgaat    420 aactttatc cgcgtgaagc aaaagttcag tggaaagttg ataatgcact gcagagcggt    480
aatagccaag aaagcgttac cgaacaggat agcaaagata gcacctatag cctgagcagc    540
accctgaccc tgagcaaagc agattatgaa aaacacaaag tgtatgcctg cgaagttacc    600
catcagggtc tgagcagtcc ggttaccaaa gctttaatc gtggtgaatg ttaattaact    660
cgaggctgag caaagcagac tactaataac ataaagtcta cgccggacgc atcgtggccc    720
tagtacgcaa gttcacgtaa aaagggtaac tagaggttga ggtgatttta tggaaattag    780
cgaagttcag ctggttgaaa gcggtggtgg tctggttcag cctggtggta gcctgcgtct    840
gagctgtgca gcaagcggtt ttaatctgta tagcagctat attcattggg ttcgtcaggc    900
accgggtaaa ggtctggaat gggttgcaag catttatccg tatagctcat ataccagcta    960
tgccgatagc gttaaaggtc gttttaccat tagcgcagat accagcaaaa ataccgcata   1020
cctgcagatg aatagtctgc gtgcagagga taccgcagtg tattattgtg cacgttatta   1080
tggtttcgcc atggattatt ggggtcaggg caccctggtt accgttagca gcgcaagcac   1140
caaaggtccg agcgtttttc cgctggcacc gagcagcaaa agcaccagcg gtggcaccgc   1200
agcactgggt tgtctggtta agattatttt tccggaaccg gttaccgtga gctggaatag   1260
cggtgcactg accagtggtg ttcataacctt tccggcagtt ctgcagagca gcggtctgta   1320
tagtctgagc agcgttgtta ccgttccgag cagtagcctg ggcacccaga cctatatttg   1380
taatgttaat cataaaccga gcaacaccaa agtggataaa aaagttgaac cgaaaagctg   1440
cgataaaacc cataccggtg gtggtagcgg tcatcatcac caccatcacc atcatggtgg   1500
tggcagtggt gtgagcggtt ggcgtctgtt caaaaaaatc agctaa                  1546
```

<210> SEQ ID NO 15
<211> LENGTH: 217
<212> TYPE: PRT
<213> ORGANISM: Artificial Sequence
<220> FEATURE:
<223> OTHER INFORMATION: light chain

<400> SEQUENCE: 15

Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Ser Val
            20                  25                  30

Ser Ser Ala Val Ala Trp Tyr Gln Gln Lys Pro Gly Lys Ala Pro Lys
        35                  40                  45

Leu Leu Ile Tyr Ser Ala Ser Ser Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln Gly Tyr Tyr
                85                  90                  95

Tyr Pro Phe Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

```
Lys Ser Gly Thr Ala Ser Val Cys Leu Leu Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 16
<211> LENGTH: 258
<212> TYPE: PRT
<213> ORGANISM: Artificial Sequence
<220> FEATURE:
<223> OTHER INFORMATION: heavy chain-HisTag-Beta9

<400> SEQUENCE: 16

Met Glu Ile Ser Glu Val Gln Leu Val Glu Ser Gly Gly Gly Leu Val
1               5                   10                  15
Gln Pro Gly Gly Ser Leu Arg Leu Ser Cys Ala Ala Ser Gly Phe Asn
            20                  25                  30
Leu Tyr Ser Ser Tyr Ile His Trp Val Arg Gln Ala Pro Gly Lys Gly
        35                  40                  45
Leu Glu Trp Val Ala Ser Ile Tyr Pro Tyr Ser Ser Tyr Thr Ser Tyr
    50                  55                  60
Ala Asp Ser Val Lys Gly Arg Phe Thr Ile Ser Ala Asp Thr Ser Lys
65                  70                  75                  80
Asn Thr Ala Tyr Leu Gln Met Asn Ser Leu Arg Ala Glu Asp Thr Ala
                85                  90                  95
Val Tyr Tyr Cys Ala Arg Tyr Tyr Gly Phe Ala Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Gly Gly Ser Gly His His His His His His
225                 230                 235                 240
His His Gly Gly Gly Ser Gly Val Ser Gly Trp Arg Leu Phe Lys Lys
                245                 250                 255
Ile Ser
```

<210> SEQ ID NO 17
<211> LENGTH: 1555
<212> TYPE: DNA
<213> ORGANISM: Artificial Sequence
<220> FEATURE:
<223> OTHER INFORMATION: Beta9-HTras

<400> SEQUENCE: 17

```
atggcaagcg atattcagat gacccagagc ccgagcagcc tgagcgcaag cgttggtgat      60
cgtgttacca ttacctgtcg tgcaagccag gatgttaata ccgcagttgc atggtatcag     120
cagaaaccgg gtaaagcacc gaaactgctg atttatagcg caagctttct gtatagcggt     180
gttccgagcc gttttagcgg tagccgtagc ggcaccgatt ttaccctgac cattagcagc     240
ctgcagccgg aagattttgc aacctattat tgtcagcagc attacaccac ccctccgacc     300
tttggtcagg gcaccaaagt tgaaattaaa cgtaccgttg cagcaccgag cgttttttatc     360
tttccgccta gcgatgagca gctgaaaagc ggtacagcca gcgttgtttg tctgctgaat     420
aactttttatc cgcgtgaagc aaaagttcag tggaaagttg ataatgcact gcagagcggt     480
aatagccaag aaagcgttac cgaacaggat agcaaagata gcacctatag cctgagcagc     540
accctgaccc tgagcaaagc agattatgaa aaacacaaag tgtatgcctg cgaagttacc     600
catcagggtc tgagcagtcc ggttaccaaa agctttaatc gtggtgaatg ttaattaact     660
cgaggctgag caaagcagac tactaataac ataaagtcta cgccggacgc atcgtggccc     720
tagtacgcaa gttcacgtaa aaagggtaac tagaggttga ggtgatttta tgggtagtat     780
gctgtttcgt gttaccatta acagcggtgg tggtagcgtt catcatcacc accatcacca     840
tcatggtggt ggcagtggtg aaattagcga agttcagctg gttgaaagcg gtggtggtct     900
ggttcagcct ggtggtagcc tgcgtctgag ctgtgcagca gcggttttta acattaaaga     960
tacctatatc cactgggttc gtcaggcacc gggtaaaggt ctggaatggg ttgcacgtat    1020
ttatccgacc aatggttata cccgttatgc cgatagcgtt aaaggtcgtt ttaccattag    1080
cgcagatacc agcaaaaata ccgcatacct gcagatgaat agtctgcgtg cagaggatac    1140
cgcagtgtat tattgtagcc gttggggtgg tgatggtttt tatgcaatgg attattgggg    1200
tcagggcacc ctggttaccg ttagcagcgc aagcaccaaa ggtccgagcg ttttttccgct    1260
ggcaccgagc agcaaaagca ccagcggtgg caccgcagca ctgggttgtc tggttaaaga    1320
ttattttccg gaaccggtta ccgtgagctg gaatagcggt gcactgacca gtggtgttca    1380
tacctttccg gcagttctgc agagcagcgg tctgtatagt ctgagcagcg ttgttaccgt    1440
tccgagcagt agcctgggca cccagaccta tatttgtaat gttaatcata aaccgagcaa    1500
caccaaagtg gataaaaaag ttgaaccgaa aagctgcgat aaaacccata cctaa         1555
```

<210> SEQ ID NO 18
<211> LENGTH: 217
<212> TYPE: PRT
<213> ORGANISM: Artificial Sequence
<220> FEATURE:
<223> OTHER INFORMATION: light chain

<400> SEQUENCE: 18

Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys

```
                35                  40                  45
Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
    195                 200                 205

Thr Lys Ser Phe Asn Arg Gly Glu Cys
210                 215

<210> SEQ ID NO 19
<211> LENGTH: 261
<212> TYPE: PRT
<213> ORGANISM: Artificial Sequence
<220> FEATURE:
<223> OTHER INFORMATION: Beta9-His Tag-heavy chain

<400> SEQUENCE: 19

Met Gly Ser Met Leu Phe Arg Val Thr Ile Asn Ser Gly Gly Gly Ser
1               5                   10                  15

Gly His His His His His His His Gly Gly Gly Ser Gly Glu Ile
                20                  25                  30

Ser Glu Val Gln Leu Val Glu Ser Gly Gly Gly Leu Val Gln Pro Gly
            35                  40                  45

Gly Ser Leu Arg Leu Ser Cys Ala Ala Ser Gly Phe Asn Ile Lys Asp
    50                  55                  60

Thr Tyr Ile His Trp Val Arg Gln Ala Pro Gly Lys Gly Leu Glu Trp
65                  70                  75                  80

Val Ala Arg Ile Tyr Pro Thr Asn Gly Tyr Thr Arg Tyr Ala Asp Ser
                85                  90                  95

Val Lys Gly Arg Phe Thr Ile Ser Ala Asp Thr Ser Lys Asn Thr Ala
                100                 105                 110

Tyr Leu Gln Met Asn Ser Leu Arg Ala Glu Asp Thr Ala Val Tyr Tyr
            115                 120                 125

Cys Ser Arg Trp Gly Gly Asp Gly Phe Tyr Ala Met Asp Tyr Trp Gly
    130                 135                 140

Gln Gly Thr Leu Val Thr Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
```

|         |         | 180     |         |         | 185     |         |         | 190     |         |         |
|---------|---------|---------|---------|---------|---------|---------|---------|---------|---------|---------|

Ser Trp Asn Ser Gly Ala Leu Thr Ser Gly Val His Thr Phe Pro Ala
    195                        200                        205

Val Leu Gln Ser Ser Gly Leu Tyr Ser Leu Ser Ser Val Val Thr Val
    210                        215                        220

Pro Ser Ser Ser Leu Gly Thr Gln Thr Tyr Ile Cys Asn Val Asn His
225                      230                        235                        240

Lys Pro Ser Asn Thr Lys Val Asp Lys Lys Val Glu Pro Lys Ser Cys
                245                        250                        255

Asp Lys Thr His Thr
          260

<210> SEQ ID NO 20
<211> LENGTH: 1555
<212> TYPE: DNA
<213> ORGANISM: Artificial Sequence
<220> FEATURE:
<223> OTHER INFORMATION: Beta10*-HTras

<400> SEQUENCE: 20

```
atggcaagcg atattcagat gacccagagc ccgagcagcc tgagcgcaag cgttggtgat      60
cgtgttacca ttacctgtcg tgcaagccag gatgttaata ccgcagttgc atggtatcag     120
cagaaaccgg gtaaagcacc gaaactgctg atttatagcg caagctttct gtatagcggt     180
gttccgagcc gttttagcgg tagccgtagc ggcaccgatt ttaccctgac cattagcagc     240
ctgcagccgg aagattttgc aacctattat tgtcagcagc attaccaccc cctccgacc      300
tttggtcagg gcaccaaagt tgaaattaaa cgtaccgttg cagcaccgag cgtttttatc     360
tttccgccta gcgatgagca gctgaaaagc ggtacagcca gcgttgtttg tctgctgaat     420
aactttatc gcgtgaagc aaaagttcag tggaaagttg ataatgcact gcagagcggt      480
aatagccaag aaagcgttac cgaacaggat agcaaagata gcacctatag cctgagcagc     540
accctgaccc tgagcaaagc agattatgaa aaacacaaag tgtatgcctg cgaagttacc     600
catcagggtc tgagcagtcc ggttaccaaa agctttaatc gtggtgaatg ttaattaact     660
cgaggctgag caaagcagac tactaataac ataaagtcta cgccggacgc atcgtggccc     720
tagtacgcaa gttcacgtaa aaagggtaac tagaggttga ggtgatttta tggtgagcgg     780
ttggcgtctg ttcaaaaaaa tcagcggtgg tggtagcggt catcatcacc accatcacca     840
tcatggtggt ggcagtggtg aaattagcga agttcagctg gttgaaagcg gtggtggtct     900
ggttcagcct ggtggtagcc tgcgtctgag ctgtgcagca gcggttttta acattaaaga     960
tacctatatc cactgggttc gtcaggcacc gggtaaaggt ctggaatggg ttgcacgtat    1020
ttatccgacc aatggttata cccgttatgc cgatagcgtt aaaggtcgtt ttaccattag    1080
cgcagatacc agcaaaaata ccgcatacct gcagatgaat agtctgcgtg cagaggatac    1140
cgcagtgtat tattgtagcc gttggggtgg tgatggtttt tatgcaatgg attattgggg    1200
tcagggcacc ctggttaccg ttagcagcgc aagcaccaaa ggtccgagcg ttttccgct    1260
ggcaccgagc agcaaaagca ccagcggtgg caccgcagca ctgggttgtc tggttaaaga    1320
ttatttccg gaaccggtta ccgtgagctg gaatagcggt gcactgacca gtggtgttca    1380
tacctttccg gcagttctgc agagcagcgg tctgtatagt ctgagcagcg ttgttaccgt    1440
tccgagcagt agcctgggca cccagaccta tatttgtaat gttaatcata aaccgagcaa    1500
caccaaagtg gataaaaaag ttgaaccgaa aagctgcgat aaaacccata cctaa         1555
```

<210> SEQ ID NO 21
<211> LENGTH: 217
<212> TYPE: PRT
<213> ORGANISM: Artificial Sequence
<220> FEATURE:
<223> OTHER INFORMATION: light chain

<400> SEQUENCE: 21

```
Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
                20                  25                  30

Asn Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 22
<211> LENGTH: 261
<212> TYPE: PRT
<213> ORGANISM: Artificial Sequence
<220> FEATURE:
<223> OTHER INFORMATION: Beta10*-His Tag-heavy chain

<400> SEQUENCE: 22

```
Met Val Ser Gly Trp Arg Leu Phe Lys Lys Ile Ser Gly Gly Gly Ser
1               5                   10                  15

Gly His His His His His His His Gly Gly Gly Ser Gly Glu Ile
                20                  25                  30

Ser Glu Val Gln Leu Val Glu Ser Gly Gly Gly Leu Val Gln Pro Gly
            35                  40                  45

Gly Ser Leu Arg Leu Ser Cys Ala Ala Ser Gly Phe Asn Ile Lys Asp
    50                  55                  60

Thr Tyr Ile His Trp Val Arg Gln Ala Pro Gly Lys Gly Leu Glu Trp
65                  70                  75                  80

Val Ala Arg Ile Tyr Pro Thr Asn Gly Tyr Thr Arg Tyr Ala Asp Ser
                85                  90                  95
```

Val Lys Gly Arg Phe Thr Ile Ser Ala Asp Thr Ser Lys Asn Thr Ala
            100                 105                 110

Tyr Leu Gln Met Asn Ser Leu Arg Ala Glu Asp Thr Ala Val Tyr Tyr
            115                 120                 125

Cys Ser Arg Trp Gly Asp Gly Phe Tyr Ala Met Asp Tyr Trp Gly
            130                 135                 140

Gln Gly Thr Leu Val Thr Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
            195                 200                 205

Val Leu Gln Ser Ser Gly Leu Tyr Ser Leu Ser Ser Val Val Thr Val
            210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Asp Lys Thr His Thr
            260

<210> SEQ ID NO 23
<211> LENGTH: 1555
<212> TYPE: DNA
<213> ORGANISM: Artificial Sequence
<220> FEATURE:
<223> OTHER INFORMATION: TrasH-Beta9

<400> SEQUENCE: 23
atggcaagcg atattcagat gacccagagc ccgagcagcc tgagcgcaag cgttggtgat      60
cgtgttacca ttacctgtcg tgcaagccag gatgttaata ccgcagttgc atggtatcag     120
cagaaaccgg gtaaagcacc gaaactgctg atttatagcg caagcttct gtatagcggt     180
gttccgagcc gttttagcgg tagccgtagc ggcaccgatt ttaccctgac cattagcagc     240
ctgcagccgg aagattttgc aacctattat tgtcagcagc attaccaccc cctccgacc     300
tttggtcagg gcaccaaagt tgaaattaaa cgtaccgttg cagcaccgag cgttttttatc     360
tttccgccta gcgatgagca gctgaaaagc ggtacagcca gcgttgtttg tctgctgaat     420
aactttatc gcgtgaagc aaaagttcag tggaaagttg ataatgcact gcagagcggt     480
aatagccaag aaagcgttac cgaacaggat agcaaagata gcacctatag cctgagcagc     540
accctgaccc tgagcaaagc agattatgaa aaacacaaag tgtatgcctg cgaagttacc     600
catcagggtc tgagcagtcc ggttaccaaa agctttaatc gtggtgaatg ttaattaact     660
cgaggctgag caaagcagac tactaataac ataaagtcta cgccggacgc atcgtggccc     720
tagtacgcaa gttcacgtaa aaagggtaac tagaggttga ggtgatttta tggaaattag     780
cgaagttcag ctggttgaaa gcggtggtgg tctggttcag cctggtggta gcctgcgtct     840
gagctgtgca gcaagcggtt ttaacattaa agataccat atccactggg ttcgtcaggc     900
accgggtaaa ggtctggaat gggttgcacg tatttatccg accaatggtt atacccgtta     960
tgccgatagc gttaaaggtc gttttaccat tagcgcagat accagcaaaa ataccgcata    1020
cctgcagatg aatagtctgc gtgcagagga taccgcagtg tattattgta gccgttgggg    1080

-continued

```
tggtgatggt ttttatgcaa tggattattg gggtcagggc accctggtta ccgttagcag    1140
cgcaagcacc aaaggtccga gcgttttttcc gctggcaccg agcagcaaaa gcaccagcgg    1200
tggcaccgca gcactgggtt gtctggttaa agattatttt ccggaaccgg ttaccgtgag    1260
ctggaatagc ggtgcactga ccagtggtgt tcatacctttc ccggcagttc tgcagagcag    1320
cggtctgtat agtctgagca gcgttgttac cgttccgagc agtagcctgg gcacccagac    1380
ctatatttgt aatgttaatc ataaaccgag caacaccaaa gtggataaaa aagttgaacc    1440
gaaaagctgc gataaaaccc ataccggtgg tggtagcggt catcatcacc accatcacca    1500
tcatggtggt ggcagtggtg gtagtatgct gtttcgtgtt accattaaca gctaa          1555
```

<210> SEQ ID NO 24
<211> LENGTH: 217
<212> TYPE: PRT
<213> ORGANISM: Artificial Sequence
<220> FEATURE:
<223> OTHER INFORMATION: light chain

<400> SEQUENCE: 24

```
Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 25
<211> LENGTH: 261
<212> TYPE: PRT
<213> ORGANISM: Artificial Sequence
<220> FEATURE:
<223> OTHER INFORMATION: heavy chain-His Tag-Beta9

<400> SEQUENCE: 25

```
Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
            20                  25                  30

Ile Lys Asp Thr Tyr Ile His Trp Val Arg Gln Ala Pro Gly Lys Gly
        35                  40                  45

Leu Glu Trp Val Ala Arg Ile Tyr Pro Thr Asn Gly Tyr Thr Arg Tyr
    50                  55                  60

Ala Asp Ser Val Lys Gly Arg Phe Thr Ile Ser Ala Asp Thr Ser Lys
65                  70                  75                  80

Asn Thr Ala Tyr Leu Gln Met Asn Ser Leu Arg Ala Glu Asp Thr Ala
                85                  90                  95

Val Tyr Tyr Cys Ser Arg Trp Gly Gly Asp Gly Phe Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Gly Gly Ser Gly His His His
225                 230                 235                 240

His His His His Gly Gly Gly Ser Gly Gly Ser Met Leu Phe Arg
                245                 250                 255

Val Thr Ile Asn Ser
            260

<210> SEQ ID NO 26
<211> LENGTH: 1555
<212> TYPE: DNA
<213> ORGANISM: Artificial Sequence
<220> FEATURE:
<223> OTHER INFORMATION: TrasH-Beta10*

<400> SEQUENCE: 26
atggcaagcg atattcagat gacccagagc ccgagcagcc tgagcgcaag cgttggtgat      60
cgtgttacca ttacctgtcg tgcaagccag gatgttaata ccgcagttgc atggtatcag     120
cagaaaccgg gtaaagcacc gaaactgctg atttatagcg caagcttcct gtatagcggt     180
gttccgagcc gttttagcgg tagccgtagc ggcaccgatt ttaccctgac cattagcagc     240
ctgcagccgg aagattttgc aacctattat tgtcagcagc attacaccac ccctccgacc     300
tttggtcagg gcaccaaagt tgaaattaaa cgtaccgttg cagcaccgag cgttttcatc     360
tttccgccta gcgatgagca gctgaaaagc ggtacagcca gcgttgtttg tctgctgaat     420 aactttttatc gcgtgaagc aaaagttcag tggaaagttg ataatgcact gcagagcggt     480
aatagccaag aaagcgttac cgaacaggat agcaaagata gcacctatag cctgagcagc     540
```

```
acccctgaccc tgagcaaagc agattatgaa aaacacaaag tgtatgcctg cgaagttacc    600
catcagggtc tgagcagtcc ggttaccaaa agctttaatc gtggtgaatg ttaattaact    660
cgaggctgag caaagcagac tactaataac ataaagtcta cgccggacgc atcgtggccc    720
tagtacgcaa gttcacgtaa aaagggtaac tagaggttga ggtgatttta tggaaattag    780
cgaagttcag ctggttgaaa gcggtggtgg tctggttcag cctggtggta gcctgcgtct    840
gagctgtgca gcaagcggtt ttaacattaa agatacctat atccactggg ttcgtcaggc    900
accgggtaaa ggtctggaat gggttgcacg tatttatccg accaatggtt atcccgtta    960 tgccgatagc gttaaaggtc gttttaccat tagcgcagat accagcaaaa ataccgcata   1020
cctgcagatg aatagtctgc gtgcagagga taccgcagtg tattattgta gccgttgggg   1080
tggtgatggt tttatgcaa tggattattg gggtcagggc accctggtta ccgttagcag   1140
cgcaagcacc aaaggtccga cgttttttcc gctggcaccg agcagcaaaa gcaccagcgg   1200
tggcaccgca gcactgggtt gtctggttaa agattatttt ccggaaccgg ttaccgtgag   1260
ctggaatagc ggtgcactga ccagtggtgt tcatacctt ccggcagttc tgcagagcag   1320
cggtctgtat agtctgagca gcgttgttac cgttccgagc agtagcctgg gcacccagac   1380
ctatatttgt aatgttaatc ataaaccgag caacaccaaa gtggataaaa aagttgaacc   1440
gaaaagctgc gataaaaccc ataccggtgg tggtagcggt catcatcacc accatcacca   1500
tcatggtggt ggcagtggtg tgagcggttg gcgtctgttc aaaaaaatca gctaa         1555
```

<210> SEQ ID NO 27
<211> LENGTH: 217
<212> TYPE: PRT
<213> ORGANISM: Artificial Sequence
<220> FEATURE:
<223> OTHER INFORMATION: light chain

<400> SEQUENCE: 27

Met Ala Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
                20                  25                  30

Asn Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser Arg
        50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 28
<211> LENGTH: 261
<212> TYPE: PRT
<213> ORGANISM: Artificial Sequence
<220> FEATURE:
<223> OTHER INFORMATION: heavy chain-His Tag-Beta10*)

<400> SEQUENCE: 28

Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
            20                  25                  30

Ile Lys Asp Thr Tyr Ile His Trp Val Arg Gln Ala Pro Gly Lys Gly
        35                  40                  45

Leu Glu Trp Val Ala Arg Ile Tyr Pro Thr Asn Gly Tyr Thr Arg Tyr
    50                  55                  60

Ala Asp Ser Val Lys Gly Arg Phe Thr Ile Ser Ala Asp Thr Ser Lys
65                  70                  75                  80

Asn Thr Ala Tyr Leu Gln Met Asn Ser Leu Arg Ala Glu Asp Thr Ala
                85                  90                  95

Val Tyr Tyr Cys Ser Arg Trp Gly Gly Asp Gly Phe Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Gly Gly Ser Gly His His His
225                 230                 235                 240

His His His His His Gly Gly Ser Gly Val Ser Gly Trp Arg Leu
                245                 250                 255

Phe Lys Lys Ile Ser
            260

<210> SEQ ID NO 29
<211> LENGTH: 1555
<212> TYPE: DNA
<213> ORGANISM: Artificial Sequence
<220> FEATURE:
<223> OTHER INFORMATION: Beta9-LPert

<400> SEQUENCE: 29
atgggtagta tgctgtttcg tgttaccatt aacagcggtg gtggtagcgg tcatcatcac    60

```
caccatcacc atcatggtgg tggcagtggt atggcaagcg atattcgat gacccagagc      120 ccgagcagcc tgagcgcaag cgttggtgat cgtgttacca ttcctgtaa ggcaagccag      180 gatgttagca ttggtgttgc atggtatcag cagaaaccgg gtaaagcacc gaaactgctg      240
atttatagcg caagctatcg ttataccggt gttccgagcc gttttagcgg tagcggcagc      300
ggcaccgatt ttaccctgac cattagcagc ctgcagccgg aagattttgc aacctattat      360
tgtcagcagt actacatcta tccgtacacc tttggtcagg gcaccaaagt tgaaattaaa      420
cgtaccgttg cagcaccgag cgttttatc ttcccgccta gcgatgagca gctgaaaagc      480
ggtacagcca gcgttgtttg tctgctgaat aactttatc cgcgtgaggc aaaagttcag      540
tggaaagttg ataatgcact gcagagcggt aatagccaag aaagcgttac cgaacaggat      600
agcaaagata gcacctatag cctgagcagc accctgaccc tgagcaaagc agattatgaa      660
aaacacaaag tgtatgcctg cgaagttacc catcagggtc tgagcagtcc ggttaccaaa      720
agctttaatc gtggtgaatg ttaattaact cgaggctgag caaagcagac tactaataac      780
ataaagtcta cgccggacgc atcgtggccc tagtacgcaa gttcacgtaa aagggtaac      840 tagaggttga ggtgatttta tggaaattag cgaagttcag ctggttgaaa gcggtggtgg      900
tctggttcag cctggtggta gcctgcgtct gagctgtgca gcaagcggtt ttacctttac      960
cgattacacc atggattggg ttcgtcaggc accgggtaaa ggtctggaat gggttgcaga     1020
tgttaatccg aatagcggtg gtagcattta taccagcgt tttaaaggtc gttttaccct     1080
gagcgttgat cgtagcaaaa ataccctgta tctgcaaatg aatagctgc gtgcagagga     1140 taccgcagtg tattattgtg cacgtaatct gggtccgagc ttctattttg attattgggg     1200
tcagggcacc ctggttaccg ttagcagcgc aagcaccaaa ggtccgagcg tttttccgct     1260
ggcaccgagc agcaaaagca ccagcggtgg caccgcagca ctgggttgtc tggttaaaga     1320
ttatttcccg gaaccggtta ccgtgagctg gaatagcgt gcactgacca gtggtgttca     1380
tacctttccg gcagttctgc agagcagcgg tctgtatagt ctgagcagcg ttgttaccgt     1440
tccgagcagt agcctgggca cccagaccta tatttgtaat gttaatcata aaccgagcaa     1500
caccaaagtg gataaaaaag ttgaaccgaa agctgcgat aaaacccata cctaa          1555
```

<210> SEQ ID NO 30
<211> LENGTH: 247
<212> TYPE: PRT
<213> ORGANISM: Artificial Sequence
<220> FEATURE:
<223> OTHER INFORMATION: Beta9-His Tag-light chain

<400> SEQUENCE: 30

```
Met Gly Ser Met Leu Phe Arg Val Thr Ile Asn Ser Gly Gly Ser
1               5                   10                  15

Gly His His His His His His His Gly Gly Gly Ser Gly Met Ala
                20                  25                  30

Ser Asp Ile Gln Met Thr Gln Ser Pro Ser Ser Leu Ser Ala Ser Val
                35                  40                  45

Gly Asp Arg Val Thr Ile Thr Cys Lys Ala Ser Gln Asp Val Ser Ile
            50                  55                  60

Gly Val Ala Trp Tyr Gln Gln Lys Pro Gly Lys Ala Pro Lys Leu Leu
65              70                  75                  80

Ile Tyr Ser Ala Ser Tyr Arg Tyr Thr Gly Val Pro Ser Arg Phe Ser
                85                  90                  95
```

Gly Ser Gly Ser Gly Thr Asp Phe Thr Leu Thr Ile Ser Ser Leu Gln
                100                 105                 110

Pro Glu Asp Phe Ala Thr Tyr Tyr Cys Gln Gln Tyr Tyr Ile Tyr Pro
            115                 120                 125

Tyr Thr Phe Gly Gln Gly Thr Lys Val Glu Ile Lys Arg Thr Val Ala
        130                 135                 140

Ala Pro Ser Val Phe Ile Phe Pro Pro Ser Asp Glu Gln Leu Lys Ser
145                 150                 155                 160

Gly Thr Ala Ser Val Cys Leu Leu Asn Asn Phe Tyr Pro Arg Glu
                165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
    210                 215                 220

Tyr Ala Cys Glu Val Thr His Gln Gly Leu Ser Ser Pro Val Thr Lys
225                 230                 235                 240

Ser Phe Asn Arg Gly Glu Cys
                245

<210> SEQ ID NO 31
<211> LENGTH: 231
<212> TYPE: PRT
<213> ORGANISM: Artificial Sequence
<220> FEATURE:
<223> OTHER INFORMATION: heavy chain

<400> SEQUENCE: 31

Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Thr Asp Tyr Thr Met Asp Trp Val Arg Gln Ala Pro Gly Lys Gly
        35                  40                  45

Leu Glu Trp Val Ala Asp Val Asn Pro Asn Ser Gly Gly Ser Ile Tyr
    50                  55                  60

Asn Gln Arg Phe Lys Gly Arg Phe Thr Leu Ser Val Asp Arg Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg Asn Leu Gly Pro Ser Phe Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

-continued

Asn His Lys Pro Ser Asn Thr Lys Val Asp Lys Lys Val Glu Pro Lys
    210                 215                 220

Ser Cys Asp Lys Thr His Thr
225                 230

<210> SEQ ID NO 32
<211> LENGTH: 1555
<212> TYPE: DNA
<213> ORGANISM: Artificial Sequence
<220> FEATURE:
<223> OTHER INFORMATION: Beta10*-LPert

<400> SEQUENCE: 32

| | |
|---|---|
| atggtgagcg gttggcgtct gttcaaaaaa atcagcggtg gtggtagcgg tcatcatcac | 60 |
| caccatcacc atcatggtgg tggcagtggt atggcaagcg atattcagat gacccagagc | 120 |
| ccgagcagcc tgagcgcaag cgttggtgat cgtgttacca ttacctgtaa ggcaagccag | 180 |
| gatgttagca ttggtgttgc atggtatcag cagaaaccgg gtaaagcacc gaaactgctg | 240 |
| atttatagcg caagctatcg ttataccggt gttccgagcc gttttagcgg tagcggcagc | 300 |
| ggcaccgatt ttaccctgac cattagcagc ctgcagccgg aagattttgc aacctattat | 360 |
| tgtcagcagt actacatcta tccgtacacc tttggtcagg gcaccaaagt tgaaattaaa | 420 |
| cgtaccgttg cagcaccgag cgttttttatc tttccgccta gcgatgagca gctgaaaagc | 480 |
| ggtacagcca gcgttgtttg tctgctgaat aactttatc cgcgtgaagc aaaagttcag | 540 |
| tggaaagttg ataatgcact gcagagcggt aatagccaag aaagcgttac cgaacaggat | 600 |
| agcaaagata gcacctatag cctgagcagc accctgaccc tgagcaaagc agattatgaa | 660 |
| aaacacaaag tgtatgcctg cgaagttacc catcagggtc tgagcagtcc ggttaccaaa | 720 |
| agctttaatc gtggtgaatg ttaattaact cgaggctgag caaagcagac tactaataac | 780 |
| ataaagtcta cgccggacgc atcgtggccc tagtacgcaa gttcacgtaa aagggtaac | 840 |
| tagaggttga ggtgatttta tggaaattag cgaagttcag ctggttgaaa gcggtggtgg | 900 |
| tctggttcag cctggtggta gcctgcgtct gagctgtgca gcaagcggtt ttacctttac | 960 |
| cgattacacc atggattggg ttcgtcaggc accgggtaaa ggtctggaat gggttgcaga | 1020 |
| tgttaatccg aatagcggtg gtagcattta taaccagcgt tttaaaggtc gttttaccct | 1080 |
| gagcgttgat cgtagcaaaa ataccctgta tctgcaaatg aatagtctgc gtgcagagga | 1140 |
| taccgcagtg tattattgtg cacgtaatct gggtccgagc ttctattttg attattgggg | 1200 |
| tcagggcacc ctggttaccg ttagcagcgc aagcaccaaa ggtccgagcg ttttccgct | 1260 |
| ggcaccgagc agcaaaagca ccagcggtgg caccgcagca ctgggttgtc tggttaaaga | 1320 |
| ttattttccg gaaccggtta ccgtgagctg gaatagcggt gcactgacca gtggtgttca | 1380 |
| tacctttccg gcagttctgc agagcagcgg tctgtatagt ctgagcagcg ttgttaccgt | 1440 |
| tccgagcagt agcctgggca cccagaccta tatttgtaat gttaatcata aaccgagcaa | 1500 |
| caccaaagtg gataaaaaag ttgaaccgaa aagctgcgat aaaacccata cctaa | 1555 |

<210> SEQ ID NO 33
<211> LENGTH: 247
<212> TYPE: PRT
<213> ORGANISM: Artificial Sequence
<220> FEATURE:
<223> OTHER INFORMATION: Beta10*-His Tag-light chain

<400> SEQUENCE: 33

Met Val Ser Gly Trp Arg Leu Phe Lys Lys Ile Ser Gly Gly Gly Ser

```
1               5                   10                  15
Gly His His His His His His His Gly Gly Gly Ser Gly Met Ala
            20                  25                  30
Ser Asp Ile Gln Met Thr Gln Ser Pro Ser Ser Leu Ser Ala Ser Val
            35                  40                  45
Gly Asp Arg Val Thr Ile Thr Cys Lys Ala Ser Gln Asp Val Ser Ile
        50                  55                  60
Gly Val Ala Trp Tyr Gln Gln Lys Pro Gly Lys Ala Pro Lys Leu Leu
65                  70                  75                  80
Ile Tyr Ser Ala Ser Tyr Arg Tyr Thr Gly Val Pro Ser Arg Phe Ser
                85                  90                  95
Gly Ser Gly Ser Gly Thr Asp Phe Thr Leu Thr Ile Ser Ser Leu Gln
                100                 105                 110
Pro Glu Asp Phe Ala Thr Tyr Tyr Cys Gln Gln Tyr Tyr Ile Tyr Pro
            115                 120                 125
Tyr Thr Phe Gly Gln Gly Thr Lys Val Glu Ile Lys Arg Thr Val Ala
        130                 135                 140
Ala Pro Ser Val Phe Ile Phe Pro Pro Ser Asp Glu Gln Leu Lys Ser
145                 150                 155                 160
Gly Thr Ala Ser Val Val Cys Leu Leu Asn Asn Phe Tyr Pro Arg Glu
                165                 170                 175
Ala Lys Val Gln Trp Lys Val Asp Asn Ala Leu Gln Ser Gly Asn Ser
                180                 185                 190
Gln Glu Ser Val Thr Glu Gln Asp Ser Lys Asp Ser Thr Tyr Ser Leu
            195                 200                 205
Ser Ser Thr Leu Thr Leu Ser Lys Ala Asp Tyr Glu Lys His Lys Val
        210                 215                 220
Tyr Ala Cys Glu Val Thr His Gln Gly Leu Ser Ser Pro Val Thr Lys
225                 230                 235                 240
Ser Phe Asn Arg Gly Glu Cys
                245

<210> SEQ ID NO 34
<211> LENGTH: 231
<212> TYPE: PRT
<213> ORGANISM: Artificial Sequence
<220> FEATURE:
<223> OTHER INFORMATION: heavy chain

<400> SEQUENCE: 34

Met Glu Ile Ser Glu Val Gln Leu Val Glu Ser Gly Gly Gly Leu Val
1               5                   10                  15
Gln Pro Gly Gly Ser Leu Arg Leu Ser Cys Ala Ala Ser Gly Phe Thr
            20                  25                  30
Phe Thr Asp Tyr Thr Met Asp Trp Val Arg Gln Ala Pro Gly Lys Gly
        35                  40                  45
Leu Glu Trp Val Ala Asp Val Asn Pro Asn Ser Gly Gly Ser Ile Tyr
    50                  55                  60
Asn Gln Arg Phe Lys Gly Arg Phe Thr Leu Ser Val Asp Arg Ser Lys
65                  70                  75                  80
Asn Thr Leu Tyr Leu Gln Met Asn Ser Leu Arg Ala Glu Asp Thr Ala
                85                  90                  95
Val Tyr Tyr Cys Ala Arg Asn Leu Gly Pro Ser Phe Tyr Phe Asp Tyr
                100                 105                 110
Trp Gly Gln Gly Thr Leu Val Thr Val Ser Ser Ala Ser Thr Lys Gly
```

```
              115                 120                 125
Pro Ser Val Phe Pro Leu Ala Pro Ser Ser Lys Ser Thr Ser Gly Gly
        130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr
225                 230

<210> SEQ ID NO 35
<211> LENGTH: 1552
<212> TYPE: DNA
<213> ORGANISM: Artificial Sequence
<220> FEATURE:
<223> OTHER INFORMATION: PertH-Beta9

<400> SEQUENCE: 35
```

| | | | |
|---|---|---|---|
| atggcaagcg atattcagat gacccagagc ccgagcagcc tgagcgcaag cgttggtgat | 60 |
| cgtgttacca ttacctgtaa ggcaagccag gatgttagca ttggtgttgc atggtatcag | 120 |
| cagaaaccgg gtaaagcacc gaaactgctg atttatagcg caagctatcg ttataccggt | 180 |
| gttccgagcc gttttagcgg tagcggcagc ggcaccgatt ttaccctgac cattagcagc | 240 |
| ctgcagccgg aagattttgc aacctattat tgtcagcagt actacatcta tccgtacacc | 300 |
| tttggtcagg gcaccaaagt tgaaattaaa cgtaccgttg cagcaccgag cgttttatc | 360 |
| tttccgccta gcgatgagca gctgaaaagc ggtacagcca gcgttgtttg tctgctgaat | 420 |
| aacttttatc cgcgtgaagc aaaagttcag tggaaagttg ataatgcact gcagagcggt | 480 |
| aatagccaag aaagcgttac cgaacaggat agcaaagata gcacctatag cctgagcagc | 540 |
| accctgaccc tgagcaaagc agattatgaa aaacacaaag tgtatgcctg cgaagttacc | 600 |
| catcagggtc tgagcagtcc ggttaccaaa agctttaatc gtggtgaatg ttaattaact | 660 |
| cgaggctgag caaagcagac tactaataac ataaagtcta cgccggacgc atcgtggccc | 720 |
| tagtacgcaa gttcacgtaa aagggtaac tagaggttga ggtgatttta tggaaattag | 780 |
| cgaagttcag ctggttgaaa gcggtggtgg tctggttcag cctggtggta gcctgcgtct | 840 |
| gagctgtgca gcaagcggtt ttacctttac cgattacacc atggattggg ttcgtcaggc | 900 |
| accgggtaaa ggtctggaat gggttgcaga tgttaatccg aatagcggtg gtagcattta | 960 |
| taaccagcgt tttaaaggtc gttttaccct gagcgttgat cgtagcaaaa ataccctgta | 1020 |
| tctgcaaatg aatagtctgc gtgcagagga taccgcagtg tattattgtg cacgtaatct | 1080 |
| gggtccgagc ttctattttg attattgggg tcagggcacc ctggttaccg ttagcagcgc | 1140 |
| aagcaccaaa ggtccgagcg tttttccgct ggcaccgagc agcaaaagca ccagcggtgg | 1200 |
| caccgcagca ctgggttgtc tggttaaaga ttattttccg gaaccggtta ccgtgagctg | 1260 |
| gaatagcggt gcactgacca gtggtgttca tacctttccg gcagttctgc agagcagcgg | 1320 |
| tctgtatagt ctgagcagcg ttgttaccgt tccgagcagt agcctgggca cccagaccta | 1380 |

-continued

```
tatttgtaat gttaatcata aaccgagcaa caccaaagtg gataaaaaag ttgaaccgaa      1440
aagctgcgat aaaacccata ccggtggtgg tagcggtcat catcaccacc atcaccatca      1500
tggtggtggc agtggtggta gtatgctgtt tcgtgttacc attaacagct aa             1552
```

<210> SEQ ID NO 36
<211> LENGTH: 217
<212> TYPE: PRT
<213> ORGANISM: Artificial Sequence
<220> FEATURE:
<223> OTHER INFORMATION: light chain

<400> SEQUENCE: 36

```
Met Ala Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 37
<211> LENGTH: 260
<212> TYPE: PRT
<213> ORGANISM: Artificial Sequence
<220> FEATURE:
<223> OTHER INFORMATION: heavy chain- His Tag-Beta9

<400> SEQUENCE: 37

```
Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Thr Asp Tyr Thr Met Asp Trp Val Arg Gln Ala Pro Gly Lys Gly
        35                  40                  45

Leu Glu Trp Val Ala Asp Val Asn Pro Asn Ser Gly Gly Ser Ile Tyr
    50                  55                  60
```

Asn Gln Arg Phe Lys Gly Arg Phe Thr Leu Ser Val Asp Arg Ser Lys
65                  70                  75                  80

Asn Thr Leu Tyr Leu Gln Met Asn Ser Leu Arg Ala Glu Asp Thr Ala
            85                  90                  95

Val Tyr Tyr Cys Ala Arg Asn Leu Gly Pro Ser Phe Tyr Phe Asp Tyr
        100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Gly Gly Gly Ser Gly His His His His
225                 230                 235                 240

His His His His Gly Gly Gly Ser Gly Gly Ser Met Leu Phe Arg Val
                245                 250                 255

Thr Ile Asn Ser
        260

<210> SEQ ID NO 38
<211> LENGTH: 1552
<212> TYPE: DNA
<213> ORGANISM: Artificial Sequence
<220> FEATURE:
<223> OTHER INFORMATION: PertH-Beta10*

<400> SEQUENCE: 38
atggcaagcg atattcagat gacccagagc ccgagcagcc tgagcgcaag cgttggtgat      60
cgtgttacca ttcctgtaa ggcaagccag gatgttagca ttggtgttgc atggtatcag     120
cagaaaccgg gtaaagcacc gaaactgctg atttatagcg caagctatcg ttataccggt    180
gttccgagcc gttttagcgg tagcggcagc ggcaccgatt ttaccctgac cattagcagc    240
ctgcagccgg aagattttgc aacctattat tgtcagcagt actacatcta tccgtacacc    300
tttggtcagg gcaccaaagt tgaaattaaa cgtaccgttg cagcaccgag cgtttttatc    360
tttccgccta gcgatgagca gctgaaaagc ggtacagcca gcgttgtttg tctgctgaat    420 aactttatc gcgtgaagc aaaagttcag tggaaagttg ataatgcact gcagagcggt    480
aatagccaag aaagcgttac cgaacaggat agcaaagata gcacctatag cctgagcagc    540
accctgaccc tgagcaaagc agattatgaa aaacacaaag tgtatgcctg cgaagttacc    600
catcagggtc tgagcagtcc ggttaccaaa agctttaatc gtggtgaatg ttaattaact    660
cgaggctgag caaagcagac tactaataac ataaagtcta cgccggacgc atcgtggccc    720
tagtacgcaa gttcacgtaa aagggtaac tagaggttga ggtgatttta tggaaattag    780
cgaagttcag ctggttgaaa gcggtggtgg tctggttcag cctggtggta gcctgcgtct    840
gagctgtgca gcaagcggtt ttacctttac cgattacacc atggattggg ttcgtcaggc    900

```
accgggtaaa ggtctggaat gggttgcaga tgttaatccg aatagcggtg gtagcattta    960
taaccagcgt tttaaaggtc gttttaccct gagcgttgat cgtagcaaaa atacccgta    1020 tctgcaaatg aatagtctgc gtgcagagga taccgcagtg tattattgtg cacgtaatct   1080
gggtccgagc ttctattttg attattgggg tcagggcacc ctggttaccg ttagcagcgc   1140
aagcaccaaa ggtccgagcg tttttccgct ggcaccgagc agcaaaagca ccagcggtgg   1200
caccgcagca ctgggttgtc tggttaaaga ttatttccg gaaccggtta ccgtgagctg   1260
gaatagcggt gcactgacca gtggtgttca tacctttccg gcagttctgc agagcagcgg   1320
tctgtatagt ctgagcagcg ttgttaccgt tccgagcagt agcctgggca cccagaccta   1380
tatttgtaat gttaatcata aaccgagcaa caccaaagtg gataaaaaag ttgaaccgaa   1440
aagctgcgat aaaacccata ccggtggtgg tagcggtcat catcaccacc atcaccatca   1500
tggtggtggc agtggtgtga gcggttggcg tctgttcaaa aaaatcagct aa           1552
```

<210> SEQ ID NO 39
<211> LENGTH: 217
<212> TYPE: PRT
<213> ORGANISM: Artificial Sequence
<220> FEATURE:
<223> OTHER INFORMATION: light chain

<400> SEQUENCE: 39

```
Met Ala Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 40
<211> LENGTH: 260
<212> TYPE: PRT

<213> ORGANISM: Artificial Sequence
<220> FEATURE:
<223> OTHER INFORMATION: heavy chain-His Tag-Beta10*

<400> SEQUENCE: 40

Met Glu Ile Ser Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Thr Asp Tyr Thr Met Asp Trp Val Arg Gln Ala Pro Gly Lys Gly
        35                  40                  45

Leu Glu Trp Val Ala Asp Val Asn Pro Asn Ser Gly Gly Ser Ile Tyr
    50                  55                  60

Asn Gln Arg Phe Lys Gly Arg Phe Thr Leu Ser Val Asp Arg Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg Asn Leu Gly Pro Ser Phe Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Ser Gly His His His His
225                 230                 235                 240

His His His His Gly Gly Gly Ser Gly Val Ser Gly Trp Arg Leu Phe
                245                 250                 255

Lys Lys Ile Ser
            260

<210> SEQ ID NO 41
<211> LENGTH: 465
<212> TYPE: DNA
<213> ORGANISM: Artificial Sequence
<220> FEATURE:
<223> OTHER INFORMATION: Beta9-G3

<400> SEQUENCE: 41
atgggtagta tgctgtttcg tgttaccatt aacagcggtg gtggtagcgg tcatcatcac      60
caccatcacc atcatggtgg tggcagtggt gatctgggta aaaaactgct ggaagcagca     120
cgtgcaggtc aggatgatga agttcgtatt ctgatggcaa atggtgcaga tgttaatgcc     180
aaagatgaat atggtctgac accgctgtat ctggcaaccg cacatggtca tctggaaatt     240
gttgaagttc tgctgaaaaa cggtgccgat gtgaatgcag ttgatgcaat tggtttttact    300 cctctgcatc tggcagcatt tattggccac ctggaaatcg ccgaggtgct gctgaaacat     360

```
ggtgcggacg ttaacgcaca ggataaattt ggtaaaaccg cctttgatat tagcattggc    420
aatggcaatg aagatctggc agaaatcctg cagaaactga actaa                   465
```

<210> SEQ ID NO 42
<211> LENGTH: 154
<212> TYPE: PRT
<213> ORGANISM: Artificial Sequence
<220> FEATURE:
<223> OTHER INFORMATION: Beta9-His Tag-G3

<400> SEQUENCE: 42

```
Met Gly Ser Met Leu Phe Arg Val Thr Ile Asn Ser Gly Gly Gly Ser
1               5                   10                  15
Gly His His His His His His His Gly Gly Gly Ser Gly Asp Leu
            20                  25                  30
Gly Lys Lys Leu Leu Glu Ala Ala Arg Ala Gly Gln Asp Asp Glu Val
        35                  40                  45
Arg Ile Leu Met Ala Asn Gly Ala Asp Val Asn Ala Lys Asp Glu Tyr
    50                  55                  60
Gly Leu Thr Pro Leu Tyr Leu Ala Thr Ala His Gly His Leu Glu Ile
65                  70                  75                  80
Val Glu Val Leu Leu Lys Asn Gly Ala Asp Val Asn Ala Val Asp Ala
                85                  90                  95
Ile Gly Phe Thr Pro Leu His Leu Ala Ala Phe Ile Gly His Leu Glu
            100                 105                 110
Ile Ala Glu Val Leu Leu Lys His Gly Ala Asp Val Asn Ala Gln Asp
        115                 120                 125
Lys Phe Gly Lys Thr Ala Phe Asp Ile Ser Ile Gly Asn Gly Asn Glu
    130                 135                 140
Asp Leu Ala Glu Ile Leu Gln Lys Leu Asn
145                 150
```

<210> SEQ ID NO 43
<211> LENGTH: 465
<212> TYPE: DNA
<213> ORGANISM: Artificial Sequence
<220> FEATURE:
<223> OTHER INFORMATION: Beta10*-G3

<400> SEQUENCE: 43

```
atggtgagcg gttggcgtct gttcaaaaaa atcagcggtg gtggtagcgg tcatcatcac    60
caccatcacc atcatggtgg tgcagtggt gatctgggta aaaaactgct ggaagcagca    120
cgtgcaggtc aggatgatga agttcgtatt ctgatggcaa atggtgcaga tgttaatgcc    180
aaagatgaat atggtctgac accgctgtat ctggcaaccg cacatggtca tctggaaatt    240
gttgaagttc tgctgaaaaa cggtgccgat gtgaatgcag ttgatgcaat ggtttttact    300
cctctgcatc tggcagcatt tattggccac ctggaaatcg ccgaggtgct gctgaaacat    360
ggtgcggacg ttaacgcaca ggataaattt ggtaaaaccg cctttgatat tagcattggc    420
aatggcaatg aagatctggc agaaatcctg cagaaactga actaa                   465
```

<210> SEQ ID NO 44
<211> LENGTH: 154
<212> TYPE: PRT
<213> ORGANISM: Artificial Sequence
<220> FEATURE:
<223> OTHER INFORMATION: Beta10*-His Tag-G3

<400> SEQUENCE: 44

```
Met Val Ser Gly Trp Arg Leu Phe Lys Lys Ile Ser Gly Gly Gly Ser
1               5                   10                  15

Gly His His His His His His Gly Gly Gly Ser Gly Asp Leu
            20                  25                  30

Gly Lys Lys Leu Leu Glu Ala Ala Arg Ala Gly Gln Asp Asp Glu Val
            35                  40                  45

Arg Ile Leu Met Ala Asn Gly Ala Asp Val Asn Ala Lys Asp Glu Tyr
        50                  55                  60

Gly Leu Thr Pro Leu Tyr Leu Ala Thr Ala His Gly His Leu Glu Ile
65                  70                  75                  80

Val Glu Val Leu Leu Lys Asn Gly Ala Asp Val Asn Ala Val Asp Ala
                85                  90                  95

Ile Gly Phe Thr Pro Leu His Leu Ala Ala Phe Ile Gly His Leu Glu
            100                 105                 110

Ile Ala Glu Val Leu Leu Lys His Gly Ala Asp Val Asn Ala Gln Asp
        115                 120                 125

Lys Phe Gly Lys Thr Ala Phe Asp Ile Ser Ile Gly Asn Gly Asn Glu
    130                 135                 140

Asp Leu Ala Glu Ile Leu Gln Lys Leu Asn
145                 150
```

<210> SEQ ID NO 45
<211> LENGTH: 489
<212> TYPE: DNA
<213> ORGANISM: Artificial Sequence
<220> FEATURE:
<223> OTHER INFORMATION: G3-Beta9

<400> SEQUENCE: 45

```
atgcgtggta gccatcatca tcaccatcat ggtagcgatc tgggtaaaaa actgctggaa      60
gcagcacgtg caggtcagga tgatgaagtt cgtattctga tggcaaatgg tgcagatgtt     120
aatgccaaag atgaatatgg tctgacaccg ctgtatctgg caaccgcaca tggtcatctg     180
gaaattgttg aagttctgct gaaaaacggt gccgatgtga atgcagttga tgcaattggt     240
tttactcctc tgcatctggc agcatttatt ggccacctgg aaatcgccga ggtgctgctg     300
aaacatggtg cggacgttaa cgcacaggat aaatttggta aaaccgcctt tgatattagc     360
attggcaatg gcaatgaaga tctggcagaa atcctgcaga actgaacgg tggtggtagc      420
ggtggtggtg gctcaggtgg cggtggttct ggtggtagta tgctgtttcg tgttaccatt     480
aacagctaa                                                             489
```

<210> SEQ ID NO 46
<211> LENGTH: 162
<212> TYPE: PRT
<213> ORGANISM: Artificial Sequence
<220> FEATURE:
<223> OTHER INFORMATION: His Tag-G3-Beta9

<400> SEQUENCE: 46

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Glu Tyr Gly Leu
        35                  40                  45

Thr Pro Leu Tyr Leu Ala Thr Ala His Gly His Leu Glu Ile Val Glu
```

```
                    50                  55                  60

Val Leu Leu Lys Asn Gly Ala Asp Val Asn Ala Val Asp Ala Ile Gly
 65                  70                  75                  80

Phe Thr Pro Leu His Leu Ala Ala Phe Ile Gly His Leu Glu Ile Ala
                     85                  90                  95

Glu Val Leu Leu Lys His Gly Ala Asp Val Asn Ala Gln Asp Lys Phe
                100                 105                 110

Gly Lys Thr Ala Phe Asp Ile Ser Ile Gly Asn Gly Asn Glu Asp Leu
            115                 120                 125

Ala Glu Ile Leu Gln Lys Leu Asn Gly Gly Ser Gly Gly Gly Gly
        130                 135                 140

Ser Gly Gly Gly Gly Ser Gly Gly Ser Met Leu Phe Arg Val Thr Ile
145                 150                 155                 160

Asn Ser

<210> SEQ ID NO 47
<211> LENGTH: 489
<212> TYPE: DNA
<213> ORGANISM: Artificial Sequence
<220> FEATURE:
<223> OTHER INFORMATION: G3-Beta10*

<400> SEQUENCE: 47
atgcgtggta gccatcatca tcaccatcat ggtagcgatc tgggtaaaaa actgctggaa      60
gcagcacgtg caggtcagga tgatgaagtt cgtattctga tggcaaatgg tgcagatgtt     120
aatgccaaag atgaatatgg tctgacaccg ctgtatctgg caaccgcaca tggtcatctg     180
gaaattgttg aagttctgct gaaaaacggt gccgatgtga atgcagttga tgcaattggt     240
tttactcctc tgcatctggc agcatttatt ggccacctgg aaatcgccga ggtgctgctg     300
aaacatggtg cggacgttaa cgcacaggat aaatttggta aaccgccttt tgatattagc     360
attggcaatg gcaatgaaga tctggcagaa atcctgcaga actgaacgg tggtggtagc     420 ggtggtggtg gctcaggtgg cggtggttct ggtgtgagcg gttggcgtct gttcaaaaaa     480
atcagctaa                                                             489

<210> SEQ ID NO 48
<211> LENGTH: 162
<212> TYPE: PRT
<213> ORGANISM: Artificial Sequence
<220> FEATURE:
<223> OTHER INFORMATION: His Tag-G3-Beta10*

<400> SEQUENCE: 48

Met Arg Gly Ser His His His His His His Gly Ser Asp Leu Gly Lys
  1               5                  10                  15

Lys Leu Leu Glu Ala Ala Arg Ala Gly Gln Asp Asp Glu Val Arg Ile
                 20                  25                  30

Leu Met Ala Asn Gly Ala Asp Val Asn Ala Lys Asp Glu Tyr Gly Leu
             35                  40                  45

Thr Pro Leu Tyr Leu Ala Thr Ala His Gly His Leu Glu Ile Val Glu
         50                  55                  60

Val Leu Leu Lys Asn Gly Ala Asp Val Asn Val Asp Ala Ile Gly
 65                  70                  75                  80

Phe Thr Pro Leu His Leu Ala Ala Phe Ile Gly His Leu Glu Ile Ala
                     85                  90                  95

Glu Val Leu Leu Lys His Gly Ala Asp Val Asn Ala Gln Asp Lys Phe
```

```
            100                 105                 110
Gly Lys Thr Ala Phe Asp Ile Ser Ile Gly Asn Gly Asn Glu Asp Leu
            115                 120                 125

Ala Glu Ile Leu Gln Lys Leu Asn Gly Gly Ser Gly Gly Gly Gly
            130                 135                 140

Ser Gly Gly Gly Gly Ser Gly Val Ser Gly Trp Arg Leu Phe Lys Lys
145                 150                 155                 160

Ile Ser
```

<210> SEQ ID NO 49
<211> LENGTH: 567
<212> TYPE: DNA
<213> ORGANISM: Artificial Sequence
<220> FEATURE:
<223> OTHER INFORMATION: Beta9-9.29

<400> SEQUENCE: 49

```
atgggtagta tgctgtttcg tgttaccatt aacagcggtg gtggtagcgg tcatcatcac    60
caccatcacc atcatggtgg tggcagtggt ggtagcgatc tgggtaaaaa actgctggaa   120
gcagcacgtg caggtcagga tgatgaagtt cgtattctga tggcaaatgg tgcagatgtt   180
aatgcccatg attttatgg tattacaccg ctgcatctgg cagcaaattt tggtcatctg   240
gaaattgttg aagtgctgct gaaacatggt gccgatgtga acgcatttga ttatgataat   300
acccctctgc acctggctgc agatgctggc cacctggaaa tcgtagaggt tctgctgaaa   360
tacggtgcgg acgttaatgc aagcgatcgt gatggtcata ccccactgca tctggcagcc   420
cgtgaaggcc atctggaaat cgtggaagta ctgctgaaaa atggcgcaga cgtgaatgca   480
caggataaat ttggtaaaac cccgtttgat ctggccattg ataatggcaa tgaagatatt   540
gccgaggtgc tgcagaaagc agcataa                                      567
```

<210> SEQ ID NO 50
<211> LENGTH: 188
<212> TYPE: PRT
<213> ORGANISM: Artificial Sequence
<220> FEATURE:
<223> OTHER INFORMATION: Beta9-His Tag-9.29

<400> SEQUENCE: 50

```
Met Gly Ser Met Leu Phe Arg Val Thr Ile Asn Ser Gly Gly Gly Ser
1               5                   10                  15

Gly His His His His His His His Gly Gly Gly Ser Gly Gly Ser
            20                  25                  30

Asp Leu Gly Lys Lys Leu Leu Glu Ala Ala Arg Ala Gly Gln Asp Asp
        35                  40                  45

Glu Val Arg Ile Leu Met Ala Asn Gly Ala Asp Val Asn Ala His Asp
    50                  55                  60

Phe Tyr Gly Ile Thr Pro Leu His Leu Ala Ala Asn Phe Gly His Leu
65                  70                  75                  80

Glu Ile Val Glu Val Leu Leu Lys His Gly Ala Asp Val Asn Ala Phe
            85                  90                  95

Asp Tyr Asp Asn Thr Pro Leu His Leu Ala Ala Asp Ala Gly His Leu
            100                 105                 110

Glu Ile Val Glu Val Leu Leu Lys Tyr Gly Ala Asp Val Asn Ala Ser
        115                 120                 125

Asp Arg Asp Gly His Thr Pro Leu His Leu Ala Ala Arg Glu Gly His
    130                 135                 140
```

```
Leu Glu Ile Val Glu Val Leu Leu Lys Asn Gly Ala Asp Val Asn Ala
145                 150                 155                 160

Gln Asp Lys Phe Gly Lys Thr Pro Phe Asp Leu Ala Ile Asp Asn Gly
            165                 170                 175

Asn Glu Asp Ile Ala Glu Val Leu Gln Lys Ala Ala
        180                 185
```

<210> SEQ ID NO 51
<211> LENGTH: 567
<212> TYPE: DNA
<213> ORGANISM: Artificial Sequence
<220> FEATURE:
<223> OTHER INFORMATION: Beta10*-9.29

<400> SEQUENCE: 51

```
atggtgagcg gttggcgtct gttcaaaaaa atcagcggtg gtggtagcgg tcatcatcac    60
caccatcacc atcatggtgg tggcagtggt ggtagcgatc tgggtaaaaa actgctggaa   120
gcagcacgtg caggtcagga tgatgaagtt cgtattctga tggcaaatgg tgcagatgtt   180
aatgcccatg attttatgg tattacaccg ctgcatctgg cagcaaattt tggtcatctg    240
gaaattgttg aagtgctgct gaaacatggt gccgatgtga acgcatttga ttatgataat    300
accccctctgc acctggctgc agatgctggc cacctggaaa tcgtagaggt tctgctgaaa    360
tacggtgcgg acgttaatgc aagcgatcgt gatggtcata ccccactgca tctggcagcc    420
cgtgaaggcc atctggaaat cgtggaagta ctgctgaaaa atggcgcaga cgtgaatgca    480
caggataaat ttggtaaaac cccgtttgat ctggccattg ataatggcaa tgaagatatt    540
gccgaggtgc tgcagaaagc agcataa                                       567
```

<210> SEQ ID NO 52
<211> LENGTH: 188
<212> TYPE: PRT
<213> ORGANISM: Artificial Sequence
<220> FEATURE:
<223> OTHER INFORMATION: Beta10*-His Tag-9.29

<400> SEQUENCE: 52

```
Met Val Ser Gly Trp Arg Leu Phe Lys Lys Ile Ser Gly Gly Gly Ser
1               5                   10                  15

Gly His His His His His His His Gly Gly Gly Ser Gly Gly Ser
            20                  25                  30

Asp Leu Gly Lys Lys Leu Leu Glu Ala Ala Arg Ala Gly Gln Asp Asp
        35                  40                  45

Glu Val Arg Ile Leu Met Ala Asn Gly Ala Asp Val Asn Ala His Asp
    50                  55                  60

Phe Tyr Gly Ile Thr Pro Leu His Leu Ala Ala Asn Phe Gly His Leu
65                  70                  75                  80

Glu Ile Val Glu Val Leu Leu Lys His Gly Ala Asp Val Asn Ala Phe
                85                  90                  95

Asp Tyr Asp Asn Thr Pro Leu His Leu Ala Ala Asp Ala Gly His Leu
            100                 105                 110

Glu Ile Val Glu Val Leu Leu Lys Tyr Gly Ala Asp Val Asn Ala Ser
        115                 120                 125

Asp Arg Asp Gly His Thr Pro Leu His Leu Ala Ala Arg Glu Gly His
    130                 135                 140

Leu Glu Ile Val Glu Val Leu Leu Lys Asn Gly Ala Asp Val Asn Ala
145                 150                 155                 160
```

Gln Asp Lys Phe Gly Lys Thr Pro Phe Asp Leu Ala Ile Asp Asn Gly
                165                 170                 175

Asn Glu Asp Ile Ala Glu Val Leu Gln Lys Ala Ala
            180                 185

<210> SEQ ID NO 53
<211> LENGTH: 567
<212> TYPE: DNA
<213> ORGANISM: Artificial Sequence
<220> FEATURE:
<223> OTHER INFORMATION: 9.29-Beta9

<400> SEQUENCE: 53

| | | | | | | |
|---|---|---|---|---|---|---|
| atgggtagcg | atctgggtaa | aaaactgctg | gaagcagcac | gtgcaggtca | ggatgatgaa | 60 |
| gttcgtattc | tgatggcaaa | tggtgcagat | gttaatgccc | atgattttta | tggtattaca | 120 |
| ccgctgcatc | tggcagcaaa | ttttggtcat | ctggaaattg | ttgaagtgct | gctgaaacat | 180 |
| ggtgccgatg | tgaacgcatt | tgattatgat | aatacccctc | tgcacctggc | tgcagatgct | 240 |
| ggccacctgg | aaatcgtaga | ggttctgctg | aaatacggtg | cggacgttaa | tgcaagcgat | 300 |
| cgtgatggtc | ataccccact | gcatctggca | gcccgtgaag | ccatctgga | atcgtggaa | 360 |
| gtactgctga | aaaatggcgc | agacgtgaat | gcacaggata | aatttggtaa | aaccccgttt | 420 |
| gatctggcca | ttgataatgg | caatgaagat | attgccgagg | tgctgcagaa | agcagcaggt | 480 |
| ggtggtagcg | gtcatcatca | ccaccatcac | catcatggtg | gtggcagtgg | tggtagtatg | 540 |
| ctgtttcgtg | ttaccattaa | cagctaa | | | | 567 |

<210> SEQ ID NO 54
<211> LENGTH: 188
<212> TYPE: PRT
<213> ORGANISM: Artificial Sequence
<220> FEATURE:
<223> OTHER INFORMATION: 9.29-His Tag-Beta9

<400> SEQUENCE: 54

Met Gly Ser Asp Leu Gly Lys Lys Leu Leu Glu Ala Ala Arg Ala Gly
1               5                   10                  15

Gln Asp Asp Glu Val Arg Ile Leu Met Ala Asn Gly Ala Asp Val Asn
            20                  25                  30

Ala His Asp Phe Tyr Gly Ile Thr Pro Leu His Leu Ala Ala Asn Phe
        35                  40                  45

Gly His Leu Glu Ile Val Glu Val Leu Leu Lys His Gly Ala Asp Val
    50                  55                  60

Asn Ala Phe Asp Tyr Asp Asn Thr Pro Leu His Leu Ala Ala Asp Ala
65                  70                  75                  80

Gly His Leu Glu Ile Val Glu Val Leu Leu Lys Tyr Gly Ala Asp Val
                85                  90                  95

Asn Ala Ser Asp Arg Asp Gly His Thr Pro Leu His Leu Ala Ala Arg
            100                 105                 110

Glu Gly His Leu Glu Ile Val Glu Val Leu Leu Lys Asn Gly Ala Asp
        115                 120                 125

Val Asn Ala Gln Asp Lys Phe Gly Lys Thr Pro Phe Asp Leu Ala Ile
    130                 135                 140

Asp Asn Gly Asn Glu Asp Ile Ala Glu Val Leu Gln Lys Ala Ala Gly
145                 150                 155                 160

Gly Gly Ser Gly His His His His His His Gly Gly Gly Ser
                165                 170                 175

```
Gly Gly Ser Met Leu Phe Arg Val Thr Ile Asn Ser
            180                 185
```

<210> SEQ ID NO 55
<211> LENGTH: 567
<212> TYPE: DNA
<213> ORGANISM: Artificial Sequence
<220> FEATURE:
<223> OTHER INFORMATION: 9.29-Beta10*

<400> SEQUENCE: 55

```
atgggtagcg atctgggtaa aaaactgctg gaagcagcac gtgcaggtca ggatgatgaa    60
gttcgtattc tgatggcaaa tggtgcagat gttaatgccc atgatttta tggtattaca   120
ccgctgcatc tggcagcaaa ttttggtcat ctggaaattg ttgaagtgct gctgaaacat   180
ggtgccgatg tgaacgcatt tgattatgat aatacccctc tgcacctggc tgcagatgct   240
ggccacctgg aaatcgtaga ggttctgctg aaatacggtg cggacgttaa tgcaagcgat   300
cgtgatggtc ataccccact gcatctggca gcccgtgaag ccatctggaa atcgtggaa   360
gtactgctga aaaatggcgc agacgtgaat gcacaggata aatttggtaa aaccccgttt   420
gatctggcca ttgataatgg caatgaagat attgccgagg tgctgcagaa agcagcaggt   480
ggtggtagcg gtcatcatca ccaccatcac catcatggtg gtggcagtgg tgtgagcggt   540
tggcgtctgt tcaaaaaaat cagctaa                                      567
```

<210> SEQ ID NO 56
<211> LENGTH: 188
<212> TYPE: PRT
<213> ORGANISM: Artificial Sequence
<220> FEATURE:
<223> OTHER INFORMATION: 9.29-His Tag-Beta10*

<400> SEQUENCE: 56

```
Met Gly Ser Asp Leu Gly Lys Lys Leu Leu Glu Ala Ala Arg Ala Gly
1               5                   10                  15
Gln Asp Asp Glu Val Arg Ile Leu Met Ala Asn Gly Ala Asp Val Asn
            20                  25                  30
Ala His Asp Phe Tyr Gly Ile Thr Pro Leu His Leu Ala Ala Asn Phe
        35                  40                  45
Gly His Leu Glu Ile Val Glu Val Leu Leu Lys His Gly Ala Asp Val
    50                  55                  60
Asn Ala Phe Asp Tyr Asp Asn Thr Pro Leu His Leu Ala Ala Asp Ala
65                  70                  75                  80
Gly His Leu Glu Ile Val Glu Val Leu Leu Lys Tyr Gly Ala Asp Val
                85                  90                  95
Asn Ala Ser Asp Arg Asp Gly His Thr Pro Leu His Leu Ala Ala Arg
            100                 105                 110
Glu Gly His Leu Glu Ile Val Glu Val Leu Leu Lys Asn Gly Ala Asp
        115                 120                 125
Val Asn Ala Gln Asp Lys Phe Gly Lys Thr Pro Phe Asp Leu Ala Ile
    130                 135                 140
Asp Asn Gly Asn Glu Asp Ile Ala Glu Val Leu Gln Lys Ala Ala Gly
145                 150                 155                 160
Gly Gly Ser Gly His His His His His His Gly Gly Gly Ser
                165                 170                 175
Gly Val Ser Gly Trp Arg Leu Phe Lys Lys Ile Ser
            180                 185
```

<210> SEQ ID NO 57
<211> LENGTH: 1479
<212> TYPE: DNA
<213> ORGANISM: Artificial Sequence
<220> FEATURE:
<223> OTHER INFORMATION: HT-Beta9-TNF

<400> SEQUENCE: 57

```
atgaaacatc atcaccatca ccacgcagaa atcggtactg gctttccatt cgaccccat      60
tatgtggaag tcctgggcga gcgcatgcac tacgtcgatg ttggtccgcg cgatggcacc    120
cctgtgctgt tcctgcacgg taacccgacc tcctcctacg tgtggcgcaa catcatcccg    180
catgttgcac cgacccatcg ctgcattgct ccagacctga tcggtatggg caaatccgac    240
aaaccagacc tggttatttt cttcgacgac acgtccgct tcatggatgc cttcatcgaa     300
gccctgggtc tggaagaggt cgtcctggtc attcacgact ggggctccgc tctgggtttc    360
cactgggcca gcgcaatcc agagcgcgta aaaggtattg catttatgga gttcatccgc     420
cctatcccga cctgggacga atggccagaa tttgcccgcg agaccttcca ggccttccgc    480
accaccgacg tcgccgcaa gctgatcatc gatcagaacg ttttatcga gggtacgctg      540
ccgatgggtg tcgtccgccc gctgactgaa gtcgagatgg accattaccg cgagccgttc    600
ctgaatcctg ttgaccgcga gccactgtgg cgcttcccaa cgagctgcc aatcgccggt     660
gagccagcga acatcgtcgc gctggtcgaa gaatacatgg actggctgca ccagtcccct    720
gtcccgaagc tgctgttctg gggcacccca ggcgttctga tcccaccggc cgaagccgct    780
cgcctggcca aaagcctgcc taactgcaag gctgtggaca tcggcccggg tctgaatctg    840
ctgcaagaag acaaccccga cctgatcggc agcgagatcg cgcgctggct gtcgacgctc    900
gagatttccg gcgagccaac cactgaggat ctgtactttc agggtagtat gctgtttcgt    960
gttaccatta cagcggtgg tggtagcggt ggtggtggca gtggtgttcg tagcagcagt   1020
cgtaccccga gcgataaacc ggttgcacat gttgttgcaa atccgcaggc cgaaggtcag   1080
ctgcagtggc tgaatcgtcg tgcaaatgca ctgctggcaa atggtgttga actgcgtgat   1140
aatcagctgg ttgttccgag cgaaggtctg tatctgattt atagccaggt tctgtttaaa   1200
ggtcagggtt gtccgagcac acatgttctg ctgacccata ccattagccg tattgcagtt   1260
agctatcaga ccaaagttaa tctgctgagc gcaattaaaa gcccgtgtca gcgtgaaaca   1320
ccggaaggtg ccgaagcaaa accgtggtat gaaccgattt atcttggtgg tgttttcag   1380
ctggaaaagg gtgatcgtct gagcgcagaa attaatcgtc cggattatct ggattttgca   1440
gaaagcggtc aggtgtattt tggcattatt gcattataa                           1479
```

<210> SEQ ID NO 58
<211> LENGTH: 492
<212> TYPE: PRT
<213> ORGANISM: Artificial Sequence
<220> FEATURE:
<223> OTHER INFORMATION: HT-Beta9-TNF

<400> SEQUENCE: 58

```
Met Lys His His His His His His Ala Glu Ile Gly Thr Gly Phe Pro
 1               5                  10                  15

Phe Asp Pro His Tyr Val Glu Val Leu Gly Glu Arg Met His Tyr Val
                20                  25                  30

Asp Val Gly Pro Arg Asp Gly Thr Pro Val Leu Phe Leu His Gly Asn
            35                  40                  45
```

```
Pro Thr Ser Ser Tyr Val Trp Arg Asn Ile Ile Pro His Val Ala Pro
    50                  55                  60

Thr His Arg Cys Ile Ala Pro Asp Leu Ile Gly Met Gly Lys Ser Asp
65                  70                  75                  80

Lys Pro Asp Leu Gly Tyr Phe Phe Asp His Val Arg Phe Met Asp
                85                  90                  95

Ala Phe Ile Glu Ala Leu Gly Leu Glu Val Val Leu Val Ile His
                100                 105                 110

Asp Trp Gly Ser Ala Leu Gly Phe His Trp Ala Lys Arg Asn Pro Glu
            115                 120                 125

Arg Val Lys Gly Ile Ala Phe Met Glu Phe Ile Arg Pro Ile Pro Thr
    130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
                165                 170                 175

Glu Gly Thr Leu Pro Met Gly Val Val Arg Pro Leu Thr Glu Val Glu
                180                 185                 190

Met Asp His Tyr Arg Glu Pro Phe Leu Asn Pro Val Asp Arg Glu Pro
            195                 200                 205

Leu Trp Arg Phe Pro Asn Glu Leu Pro Ile Ala Gly Glu Pro Ala Asn
    210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
                245                 250                 255

Ala Glu Ala Ala Arg Leu Ala Lys Ser Leu Pro Asn Cys Lys Ala Val
                260                 265                 270

Asp Ile Gly Pro Gly Leu Asn Leu Leu Gln Glu Asp Asn Pro Asp Leu
            275                 280                 285

Ile Gly Ser Glu Ile Ala Arg Trp Leu Ser Thr Leu Glu Ile Ser Gly
    290                 295                 300

Glu Pro Thr Thr Glu Asp Leu Tyr Phe Gln Gly Ser Met Leu Phe Arg
305                 310                 315                 320

Val Thr Ile Asn Ser Gly Gly Ser Gly Gly Gly Ser Gly Val
                325                 330                 335

Arg Ser Ser Ser Arg Thr Pro Ser Asp Lys Pro Val Ala His Val Val
            340                 345                 350

Ala Asn Pro Gln Ala Glu Gly Gln Leu Gln Trp Leu Asn Arg Arg Ala
    355                 360                 365

Asn Ala Leu Leu Ala Asn Gly Val Glu Leu Arg Asp Asn Gln Leu Val
    370                 375                 380

Val Pro Ser Glu Gly Leu Tyr Leu Ile Tyr Ser Gln Val Leu Phe Lys
385                 390                 395                 400

Gly Gln Gly Cys Pro Ser Thr His Val Leu Leu Thr His Thr Ile Ser
                405                 410                 415

Arg Ile Ala Val Ser Tyr Gln Thr Lys Val Asn Leu Leu Ser Ala Ile
            420                 425                 430

Lys Ser Pro Cys Gln Arg Glu Thr Pro Glu Gly Ala Glu Ala Lys Pro
        435                 440                 445

Trp Tyr Glu Pro Ile Tyr Leu Gly Gly Val Phe Gln Leu Glu Lys Gly
    450                 455                 460
```

Asp Arg Leu Ser Ala Glu Ile Asn Arg Pro Asp Tyr Leu Asp Phe Ala
465                 470                 475                 480

Glu Ser Gly Gln Val Tyr Phe Gly Ile Ile Ala Leu
                485                 490

<210> SEQ ID NO 59
<211> LENGTH: 1482
<212> TYPE: DNA
<213> ORGANISM: Artificial Sequence
<220> FEATURE:
<223> OTHER INFORMATION: HT-TNF-Beta9

<400> SEQUENCE: 59

| | | | | | |
|---|---|---|---|---|---|
| atgaaacatc | atcaccatca | ccacgcagaa | atcggtactg | gctttccatt | cgaccccat | 60 |
| tatgtggaag | tcctgggcga | gcgcatgcac | tacgtcgatg | ttggtccgcg | cgatggcacc | 120 |
| cctgtgctgt | tcctgcacgg | taacccgacc | tcctcctacg | tgtggcgcaa | catcatcccg | 180 |
| catgttgcac | cgacccatcg | ctgcattgct | ccagacctga | tcggtatggg | caaatccgac | 240 |
| aaaccagacc | tgggttattt | cttcgacgac | cacgtccgct | tcatggatgc | cttcatcgaa | 300 |
| gccctgggtc | tggaagaggt | cgtcctggtc | attcacgact | ggggctccgc | tctgggtttc | 360 |
| cactgggcca | agcgcaatcc | agagcgcgtc | aaaggtattg | catttatgga | gttcatccgc | 420 |
| cctatcccga | cctgggacga | atggccagaa | tttgcccgcg | agaccttcca | ggccttccgc | 480 |
| accaccgacg | tcggccgcaa | gctgatcatc | gatcagaacg | tttttatcga | gggtacgctg | 540 |
| ccgatgggtg | tcgtccgccc | gctgactgaa | gtcgagatgg | accattaccg | cgagccgttc | 600 |
| ctgaatcctg | ttgaccgcga | gccactgtgg | cgcttcccaa | cgagctgcc | aatcgccggt | 660 |
| gagccagcga | catcgtcgc | gctggtcgaa | gaatacatgg | actggctgca | ccagtcccct | 720 |
| gtcccgaagc | tgctgttctg | gggcacccca | ggcgttctga | tcccaccggc | cgaagccgct | 780 |
| cgcctggcca | aaagcctgcc | taactgcaag | gctgtggaca | tcggcccggg | tctgaatctg | 840 |
| ctgcaagaag | acaaccccga | cctgatcggc | agcgagatcg | cgcgctggct | gtcgacgctc | 900 |
| gagatttccg | gcgagccaac | cactgaggat | ctgtactttc | agggtgttcg | tagcagcagt | 960 |
| cgtaccccga | gcgataaacc | ggttgcacat | gttgttgcaa | atccgcaggc | cgaaggtcag | 1020 |
| ctgcagtggc | tgaatcgtcg | tgcaaatgca | ctgctggcaa | atggtgttga | actgcgtgat | 1080 |
| aatcagctgg | ttgttccgag | cgaaggtctg | tatctgattt | atagccaggt | tctgtttaaa | 1140 |
| ggtcagggtt | gtccgagcac | acatgttctg | ctgacccata | ccattagccg | tattgcagtt | 1200 |
| agctatcaga | ccaaagttaa | tctgctgagc | gcaattaaaa | gcccgtgtca | gcgtgaaaca | 1260 |
| ccggaaggtg | ccgaagcaaa | accgtggtat | gaaccgattt | atcttggtgg | tgtttttcag | 1320 |
| ctggaaaagg | gtgatcgtct | gagcgcagaa | attaatcgtc | cggattatct | ggattttgca | 1380 |
| gaaagcggtc | aggtgtattt | tggcattatt | gcattaggcg | gtggttcagg | tggtggcggt | 1440 |
| tctggtggta | gtatgctgtt | tcgtgttacc | attaacagct | aa | | 1482 |

<210> SEQ ID NO 60
<211> LENGTH: 493
<212> TYPE: PRT
<213> ORGANISM: Artificial Sequence
<220> FEATURE:
<223> OTHER INFORMATION: HT-TNF-Beta9

<400> SEQUENCE: 60

Met Lys His His His His His His Ala Glu Ile Gly Thr Gly Phe Pro
1               5                   10                  15

-continued

Phe Asp Pro His Tyr Val Glu Val Leu Gly Glu Arg Met His Tyr Val
         20                  25                  30

Asp Val Gly Pro Arg Asp Gly Thr Pro Val Leu Phe Leu His Gly Asn
             35                  40                  45

Pro Thr Ser Ser Tyr Val Trp Arg Asn Ile Ile Pro His Val Ala Pro
 50                  55                  60

Thr His Arg Cys Ile Ala Pro Asp Leu Ile Gly Met Gly Lys Ser Asp
 65                  70                  75                  80

Lys Pro Asp Leu Gly Tyr Phe Phe Asp Asp His Val Arg Phe Met Asp
                 85                  90                  95

Ala Phe Ile Glu Ala Leu Gly Leu Glu Glu Val Val Leu Val Ile His
             100                 105                 110

Asp Trp Gly Ser Ala Leu Gly Phe His Trp Ala Lys Arg Asn Pro Glu
             115                 120                 125

Arg Val Lys Gly Ile Ala Phe Met Glu Phe Ile Arg Pro Ile Pro Thr
         130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
                 165                 170                 175

Glu Gly Thr Leu Pro Met Gly Val Val Arg Pro Leu Thr Glu Val Glu
             180                 185                 190

Met Asp His Tyr Arg Glu Pro Phe Leu Asn Pro Val Asp Arg Glu Pro
             195                 200                 205

Leu Trp Arg Phe Pro Asn Glu Leu Pro Ile Ala Gly Glu Pro Ala Asn
         210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
                 245                 250                 255

Ala Glu Ala Ala Arg Leu Ala Lys Ser Leu Pro Asn Cys Lys Ala Val
             260                 265                 270

Asp Ile Gly Pro Gly Leu Asn Leu Leu Gln Glu Asp Asn Pro Asp Leu
         275                 280                 285

Ile Gly Ser Glu Ile Ala Arg Trp Leu Ser Thr Leu Glu Ile Ser Gly
         290                 295                 300

Glu Pro Thr Thr Glu Asp Leu Tyr Phe Gln Gly Val Arg Ser Ser Ser
305                 310                 315                 320

Arg Thr Pro Ser Asp Lys Pro Val Ala His Val Val Ala Asn Pro Gln
             325                 330                 335

Ala Glu Gly Gln Leu Gln Trp Leu Asn Arg Arg Ala Asn Ala Leu Leu
             340                 345                 350

Ala Asn Gly Val Glu Leu Arg Asp Asn Gln Leu Val Val Pro Ser Glu
         355                 360                 365

Gly Leu Tyr Leu Ile Tyr Ser Gln Val Leu Phe Lys Gly Gln Gly Cys
         370                 375                 380

Pro Ser Thr His Val Leu Leu Thr His Thr Ile Ser Arg Ile Ala Val
385                 390                 395                 400

Ser Tyr Gln Thr Lys Val Asn Leu Leu Ser Ala Ile Lys Ser Pro Cys
                 405                 410                 415

Gln Arg Glu Thr Pro Glu Gly Ala Glu Ala Lys Pro Trp Tyr Glu Pro
             420                 425                 430

Ile Tyr Leu Gly Gly Val Phe Gln Leu Glu Lys Gly Asp Arg Leu Ser

```
                435              440              445
Ala Glu Ile Asn Arg Pro Asp Tyr Leu Asp Phe Ala Glu Ser Gly Gln
    450              455              460

Val Tyr Phe Gly Ile Ile Ala Leu Gly Gly Gly Ser Gly Gly Gly Gly
465              470              475              480

Ser Gly Gly Ser Met Leu Phe Arg Val Thr Ile Asn Ser
                485              490
```

<210> SEQ ID NO 61
<211> LENGTH: 1482
<212> TYPE: DNA
<213> ORGANISM: Artificial Sequence
<220> FEATURE:
<223> OTHER INFORMATION: HT-Beta10*-TNF

<400> SEQUENCE: 61

```
atgaaacatc atcaccatca ccacgcagaa atcggtactg gctttccatt cgaccccat      60
tatgtggaag tcctgggcga gcgcatgcac tacgtcgatg ttggtccgcg cgatggcacc     120
cctgtgctgt tcctgcacgg taacccgacc tcctcctacg tgtggcgcaa catcatcccg     180
catgttgcac cgacccatcg ctgcattgct ccagacctga tcggtatggg caaatccgac     240
aaaccagacc tgggttattt cttcgacgac cacgtccgct tcatggatgc cttcatcgaa     300
gccctgggtc tggaagaggt cgtcctggtc attcacgact ggggctccgc tctgggtttc     360
cactgggcca agcgcaatcc agagcgcgtc aaaggtattg catttatgga gttcatccgc     420
cctatcccga cctgggacga atggccagaa tttgcccgcg agaccttcca ggccttccgc     480
accaccgacg tcggccgcaa gctgatcatc gatcagaacg tttttatcga gggtacgctg     540
ccgatgggtg tcgtccgccc gctgactgaa gtcgagatgg accattaccg cgagccgttc     600
ctgaatcctg ttgaccgcga gccactgtgg cgcttcccaa acgagctgcc aatcgccggt     660
gagccagcga acatcgtcgc gctggtcgaa gaatacatgg actggctgca ccagtcccct     720
gtcccgaagc tgctgttctg gggcaccccca ggcgttctga tcccaccggc cgaagccgct     780
cgcctggcca aaagcctgcc taactgcaag gctgtggaca tcggcccggg tctgaatctg     840
ctgcaagaag acaacccgga cctgatcggc agcgagatcg cgcgctggct gtcgacgctc     900
gagatttccg cgagccaac cactgaggat ctgtactttc agggtgtgag cggttggcgt     960
ctgttcaaaa aaatcagcgg tggtggtagc ggtggtggtg gcagtggtgt tcgtagcagc    1020
agtcgtaccc cgagcgataa accggttgca catgttgttg caaatccgca ggccgaaggt    1080
cagctgcagt ggctgaatcg tcgtgcaaat gcactgctgg caaatggtgt tgaactgcgt    1140
gataatcagc tggttgttcc gagcgaaggt ctgtatctga tttatagcca ggttctgttt    1200
aaaggtcagg gttgtccgag cacacatgtt ctgctgaccc ataccattag ccgtattgca    1260
gttagctatc agaccaaagt taatctgctg agcgcaatta aagcccgtgt tcagcgtgaa    1320
acaccggaag gtgccgaagc aaaaccgtgg tatgaaccga tttatcttgg tggtgttttt    1380
cagctggaaa agggtgatcg tctgagcgca gaaattaatc gtccggatta tctggatttt    1440
gcagaaagcg gtcaggtgta ttttggcatt attgcattat aa                       1482
```

<210> SEQ ID NO 62
<211> LENGTH: 493
<212> TYPE: PRT
<213> ORGANISM: Artificial Sequence
<220> FEATURE:
<223> OTHER INFORMATION: HT-Beta10*-TNF

<400> SEQUENCE: 62

```
Met Lys His His His His His Ala Glu Ile Gly Thr Gly Phe Pro
1               5                   10                  15

Phe Asp Pro His Tyr Val Glu Val Leu Gly Glu Arg Met His Tyr Val
            20                  25                  30

Asp Val Gly Pro Arg Asp Gly Thr Pro Val Leu Phe Leu His Gly Asn
        35                  40                  45

Pro Thr Ser Ser Tyr Val Trp Arg Asn Ile Ile Pro His Val Ala Pro
    50                  55                  60

Thr His Arg Cys Ile Ala Pro Asp Leu Ile Gly Met Gly Lys Ser Asp
65                  70                  75                  80

Lys Pro Asp Leu Gly Tyr Phe Phe Asp Asp His Val Arg Phe Met Asp
                85                  90                  95

Ala Phe Ile Glu Ala Leu Gly Leu Glu Glu Val Val Leu Val Ile His
            100                 105                 110

Asp Trp Gly Ser Ala Leu Gly Phe His Trp Ala Lys Arg Asn Pro Glu
        115                 120                 125

Arg Val Lys Gly Ile Ala Phe Met Glu Phe Ile Arg Pro Ile Pro Thr
    130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
                165                 170                 175

Glu Gly Thr Leu Pro Met Gly Val Val Arg Pro Leu Thr Glu Val Glu
            180                 185                 190

Met Asp His Tyr Arg Glu Pro Phe Leu Asn Pro Val Asp Arg Glu Pro
        195                 200                 205

Leu Trp Arg Phe Pro Asn Glu Leu Pro Ile Ala Gly Glu Pro Ala Asn
    210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
                245                 250                 255

Ala Glu Ala Ala Arg Leu Ala Lys Ser Leu Pro Asn Cys Lys Ala Val
            260                 265                 270

Asp Ile Gly Pro Gly Leu Asn Leu Leu Gln Glu Asp Asn Pro Asp Leu
        275                 280                 285

Ile Gly Ser Glu Ile Ala Arg Trp Leu Ser Thr Leu Glu Ile Ser Gly
    290                 295                 300

Glu Pro Thr Thr Glu Asp Leu Tyr Phe Gln Gly Val Ser Gly Trp Arg
305                 310                 315                 320

Leu Phe Lys Lys Ile Ser Gly Gly Ser Gly Gly Gly Ser Gly
                325                 330                 335

Val Arg Ser Ser Ser Arg Thr Pro Ser Asp Lys Pro Val Ala His Val
            340                 345                 350

Val Ala Asn Pro Gln Ala Glu Gly Gln Leu Gln Trp Leu Asn Arg Arg
        355                 360                 365

Ala Asn Ala Leu Leu Ala Asn Gly Val Glu Leu Arg Asp Asn Gln Leu
    370                 375                 380

Val Val Pro Ser Glu Gly Leu Tyr Leu Ile Tyr Ser Gln Val Leu Phe
385                 390                 395                 400

Lys Gly Gln Gly Cys Pro Ser Thr His Val Leu Leu Thr His Thr Ile
                405                 410                 415
```

```
Ser Arg Ile Ala Val Ser Tyr Gln Thr Lys Val Asn Leu Leu Ser Ala
            420                 425                 430

Ile Lys Ser Pro Cys Gln Arg Glu Thr Pro Glu Gly Ala Glu Ala Lys
            435                 440                 445

Pro Trp Tyr Glu Pro Ile Tyr Leu Gly Gly Val Phe Gln Leu Glu Lys
450                 455                 460

Gly Asp Arg Leu Ser Ala Glu Ile Asn Arg Pro Asp Tyr Leu Asp Phe
465                 470                 475                 480

Ala Glu Ser Gly Gln Val Tyr Phe Gly Ile Ile Ala Leu
                485                 490

<210> SEQ ID NO 63
<211> LENGTH: 1482
<212> TYPE: DNA
<213> ORGANISM: Artificial Sequence
<220> FEATURE:
<223> OTHER INFORMATION: HT-TNF-Beta10*

<400> SEQUENCE: 63
atgaaacatc atcaccatca ccacgcagaa atcggtactg gctttccatt cgaccccat        60 tatgtggaag tcctgggcga gcgcatgcac tacgtcgatg ttggtccgcg cgatggcacc       120
cctgtgctgt tcctgcacgg taacccgacc tcctcctacg tgtggcgcaa catcatcccg       180
catgttgcac cgaccatcg ctgcattgct ccagacctga tcggtatggg caaatccgac        240
aaaccagacc tgggttattt cttcgacgac cacgtccgct tcatggatgc cttcatcgaa       300
gccctgggtc tggaagaggt cgtcctggtc attcacgact ggggctccgc tctgggtttc       360
cactgggcca agcgcaatcc agagcgcgtc aaaggtattg catttatgga gttcatccgc       420
cctatcccga cctgggacga atggccagaa tttgcccgcg agaccttcca ggccttccgc       480
accaccgacg tcggccgcaa gctgatcatc gatcagaacg tttttatcga gggtacgctg       540
ccgatgggtg tcgtccgccc gctgactgaa gtcgagatgg accattaccg cgagccgttc       600
ctgaatcctg ttgaccgcga gccactgtgg cgcttcccaa cgagctgcc aatcgccggt        660 gagccagcga acatcgtcgc gctggtcgaa gaatacatgg actggctgca ccagtcccct       720
gtcccgaagc tgctgttctg gggcacccca ggcgttctga tcccaccggc cgaagccgct       780
cgcctggcca aaagcctgcc taactgcaag gctgtggaca tcggcccggg tctgaatctg       840
ctgcaagaag acaacccgga cctgatcggc agcgagatcg cgcgctggct gtcgacgctc       900
gagatttccg gcgagccaac cactgaggat ctgtactttc agggtgttcg tagcagcagt       960
cgtaccccga gcgataaacc ggttgcacat gttgttgcaa atccgcaggc cgaaggtcag      1020
ctgcagtggc tgaatcgtcg tgcaaatgca ctgctggcaa tggtgttga actgcgtgat      1080 aatcagctgg ttgttccgag cgaaggtctg tatctgattt atagccaggt tctgtttaaa      1140
ggtcagggtt gtccgagcac acatgttctg ctgacccata ccattagccg tattgcagtt      1200
agctatcaga ccaaagttaa tctgctgagc gcaattaaaa gcccgtgtca gcgtgaaaca      1260
ccggaaggtg ccgaagcaaa accgtggtat gaaccgattt atcttggtgg tgttttcag        1320 ctggaaaagg gtgatcgtct gagcgcagaa attaatcgtc cggattatct ggattttgca      1380
gaaagcggtc aggtgtattt tggcattatt gcattaggcg tggttcagg tggtggcggt       1440 tctggtgtta gcggttggcg tctgtttaaa aagattagct aa                         1482

<210> SEQ ID NO 64
<211> LENGTH: 493
```

<212> TYPE: PRT
<213> ORGANISM: Artificial Sequence
<220> FEATURE:
<223> OTHER INFORMATION: HT-TNF-Beta10*

<400> SEQUENCE: 64

```
Met Lys His His His His His His Ala Glu Ile Gly Thr Gly Phe Pro
1               5                   10                  15

Phe Asp Pro His Tyr Val Glu Val Leu Gly Glu Arg Met His Tyr Val
                20                  25                  30

Asp Val Gly Pro Arg Asp Gly Thr Pro Val Leu Phe Leu His Gly Asn
            35                  40                  45

Pro Thr Ser Ser Tyr Val Trp Arg Asn Ile Ile Pro His Val Ala Pro
    50                  55                  60

Thr His Arg Cys Ile Ala Pro Asp Leu Ile Gly Met Gly Lys Ser Asp
65                  70                  75                  80

Lys Pro Asp Leu Gly Tyr Phe Phe Asp Asp His Val Arg Phe Met Asp
                85                  90                  95

Ala Phe Ile Glu Ala Leu Gly Leu Glu Glu Val Val Leu Val Ile His
                100                 105                 110

Asp Trp Gly Ser Ala Leu Gly Phe His Trp Ala Lys Arg Asn Pro Glu
            115                 120                 125

Arg Val Lys Gly Ile Ala Phe Met Glu Phe Ile Arg Pro Ile Pro Thr
        130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
                165                 170                 175

Glu Gly Thr Leu Pro Met Gly Val Val Arg Pro Leu Thr Glu Val Glu
                180                 185                 190

Met Asp His Tyr Arg Glu Pro Phe Leu Asn Pro Val Asp Arg Glu Pro
            195                 200                 205

Leu Trp Arg Phe Pro Asn Glu Leu Pro Ile Ala Gly Glu Pro Ala Asn
        210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
                245                 250                 255

Ala Glu Ala Ala Arg Leu Ala Lys Ser Leu Pro Asn Cys Lys Ala Val
                260                 265                 270

Asp Ile Gly Pro Gly Leu Asn Leu Leu Gln Glu Asp Asn Pro Asp Leu
            275                 280                 285

Ile Gly Ser Glu Ile Ala Arg Trp Leu Ser Thr Leu Glu Ile Ser Gly
        290                 295                 300

Glu Pro Thr Thr Glu Asp Leu Tyr Phe Gln Gly Val Arg Ser Ser Ser
305                 310                 315                 320

Arg Thr Pro Ser Asp Lys Pro Val Ala His Val Val Ala Asn Pro Gln
                325                 330                 335

Ala Glu Gly Gln Leu Gln Trp Leu Asn Arg Arg Ala Asn Ala Leu Leu
            340                 345                 350

Ala Asn Gly Val Glu Leu Arg Asp Asn Gln Leu Val Val Pro Ser Glu
        355                 360                 365

Gly Leu Tyr Leu Ile Tyr Ser Gln Val Leu Phe Lys Gly Gln Gly Cys
370                 375                 380
```

```
Pro Ser Thr His Val Leu Leu Thr His Thr Ile Ser Arg Ile Ala Val
385                 390                 395                 400

Ser Tyr Gln Thr Lys Val Asn Leu Leu Ser Ala Ile Lys Ser Pro Cys
            405                 410                 415

Gln Arg Glu Thr Pro Glu Gly Ala Glu Ala Lys Pro Trp Tyr Glu Pro
            420                 425                 430

Ile Tyr Leu Gly Gly Val Phe Gln Leu Glu Lys Gly Asp Arg Leu Ser
            435                 440                 445

Ala Glu Ile Asn Arg Pro Asp Tyr Leu Asp Phe Ala Glu Ser Gly Gln
    450                 455                 460

Val Tyr Phe Gly Ile Ile Ala Leu Gly Gly Ser Gly Gly Gly
465                 470                 475                 480

Ser Gly Val Ser Gly Trp Arg Leu Phe Lys Lys Ile Ser
            485                 490
```

```
<210> SEQ ID NO 65
<211> LENGTH: 564
<212> TYPE: DNA
<213> ORGANISM: Artificial Sequence
<220> FEATURE:
<223> OTHER INFORMATION: Beta9-TNF

<400> SEQUENCE: 65
atgggtagta tgctgtttcg tgttaccatt aacagcggtg gtggtagcgg tcatcatcac      60
caccatcacc atcatggtgg tggcagtggt gttcgtagca gcagtcgtac cccgagcgat     120
aaaccggttg cacatgttgt tgcaaatccg caggccgaag gtcagctgca gtggctgaat     180
cgtcgtgcaa atgcactgct ggcaaatggt gttgaactgc gtgataatca gctggttgtt     240
ccgagcgaag gtctgtatct gatttatagc caggttctgt ttaaaggtca gggttgtccg     300
agcacacatg ttctgctgac ccataccatt agccgtattg cagttagcta tcagaccaaa     360
gttaatctgc tgagcgcaat taaaagcccg tgtcagcgtg aaaccggaag gtgccgaa      420 gcaaaaccgt ggtatgaacc gatttatctt ggtggtgttt ttcagctgga aaagggtgat     480
cgtctgagcg cagaaattaa tcgtccggat tatctggatt ttgcagaaag cggtcaggtg     540
tattttggca ttattgcatt ataa                                             564
```

```
<210> SEQ ID NO 66
<211> LENGTH: 187
<212> TYPE: PRT
<213> ORGANISM: Artificial Sequence
<220> FEATURE:
<223> OTHER INFORMATION: Beta9-TNF

<400> SEQUENCE: 66

Met Gly Ser Met Leu Phe Arg Val Thr Ile Asn Ser Gly Gly Gly Ser
1               5                   10                  15

Gly His His His His His His His Gly Gly Gly Ser Gly Val Arg
            20                  25                  30

Ser Ser Ser Arg Thr Pro Ser Asp Lys Pro Val Ala His Val Val Ala
            35                  40                  45

Asn Pro Gln Ala Glu Gly Gln Leu Gln Trp Leu Asn Arg Arg Ala Asn
    50                  55                  60

Ala Leu Leu Ala Asn Gly Val Glu Leu Arg Asp Asn Gln Leu Val Val
65                  70                  75                  80

Pro Ser Glu Gly Leu Tyr Leu Ile Tyr Ser Gln Val Leu Phe Lys Gly
                85                  90                  95
```

Gln Gly Cys Pro Ser Thr His Val Leu Leu Thr His Thr Ile Ser Arg
                100                 105                 110

Ile Ala Val Ser Tyr Gln Thr Lys Val Asn Leu Leu Ser Ala Ile Lys
            115                 120                 125

Ser Pro Cys Gln Arg Glu Thr Pro Glu Gly Ala Glu Ala Lys Pro Trp
        130                 135                 140

Tyr Glu Pro Ile Tyr Leu Gly Gly Val Phe Gln Leu Glu Lys Gly Asp
145                 150                 155                 160

Arg Leu Ser Ala Glu Ile Asn Arg Pro Asp Tyr Leu Asp Phe Ala Glu
                165                 170                 175

Ser Gly Gln Val Tyr Phe Gly Ile Ile Ala Leu
            180                 185

<210> SEQ ID NO 67
<211> LENGTH: 564
<212> TYPE: DNA
<213> ORGANISM: Artificial Sequence
<220> FEATURE:
<223> OTHER INFORMATION: TNF-Beta9

<400> SEQUENCE: 67
atggttcgta gcagcagtcg taccccgagc gataaaccgg ttgcacatgt tgttgcaaat      60
ccgcaggccg aaggtcagct gcagtggctg aatcgtcgtg caaatgcact gctggcaaat     120
ggtgttgaac tgcgtgataa tcagctggtt gttccgagcg aaggtctgta tctgatttat     180
agccaggttc tgtttaaagg tcagggttgt ccgagcacac atgttctgct gacccatacc     240
attagccgta ttgcagttag ctatcagacc aaagttaatc tgctgagcgc aattaaaagc     300
ccgtgtcagc gtgaaacacc ggaaggtgcc gaagcaaaac cgtggtatga accgatttat     360
cttggtggtg ttttttcagct ggaaaagggt gatcgtctga gcgcagaaat taatcgtccg     420
gattatctgg attttgcaga aagcggtcag gtgtattttg gcattattgc attaggtggt     480
ggtagcggtc atcatcacca ccatcaccat catggtggtg gcagtggtgg tagtatgctg     540
tttcgtgtta ccattaacag ctaa                                            564

<210> SEQ ID NO 68
<211> LENGTH: 187
<212> TYPE: PRT
<213> ORGANISM: Artificial Sequence
<220> FEATURE:
<223> OTHER INFORMATION: TNF-Beta9

<400> SEQUENCE: 68

Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

-continued

```
Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu Gly Gly
145                 150                 155                 160

Gly Ser Gly His His His His His His Gly Gly Gly Ser Gly
                165                 170                 175

Gly Ser Met Leu Phe Arg Val Thr Ile Asn Ser
        180                 185
```

<210> SEQ ID NO 69
<211> LENGTH: 564
<212> TYPE: DNA
<213> ORGANISM: Artificial Sequence
<220> FEATURE:
<223> OTHER INFORMATION: Beta10*-TNF

<400> SEQUENCE: 69

```
atggtgagcg gttggcgtct gttcaaaaaa atcagcggtg gtggtagcgg tcatcatcac      60
caccatcacc atcatggtgg tggcagtggt gttcgtagca gcagtcgtac cccgagcgat     120
aaaccggttg cacatgttgt tgcaaatccg caggccgaag gtcagctgca gtggctgaat     180
cgtcgtgcaa atgcactgct ggcaaatggt gttgaactgc gtgataatca gctggttgtt     240
ccgagcgaag gtctgtatct gatttatagc caggttctgt ttaaaggtca gggttgtccg     300
agcacacatg ttctgctgac ccataccatt agccgtattg cagttagcta tcagaccaaa     360
gttaatctgc tgagcgcaat taaaagcccg tgtcagcgtg aaacaccgga aggtgccgaa     420
gcaaaaccgt ggtatgaacc gatttatctt ggtggtgttt ttcagctgga aaagggtgat     480
cgtctgagcg cagaaattaa tcgtccggat tatctggatt ttgcagaaag cggtcaggtg     540
tattttggca ttattgcatt ataa                                            564
```

<210> SEQ ID NO 70
<211> LENGTH: 187
<212> TYPE: PRT
<213> ORGANISM: Artificial Sequence
<220> FEATURE:
<223> OTHER INFORMATION: Beta10*-TNF

<400> SEQUENCE: 70

```
Met Val Ser Gly Trp Arg Leu Phe Lys Lys Ile Ser Gly Gly Gly Ser
1               5                   10                  15

Gly His His His His His His Gly Gly Gly Ser Gly Val Arg
            20                  25                  30

Ser Ser Ser Arg Thr Pro Ser Asp Lys Pro Val Ala His Val Val Ala
            35                  40                  45

Asn Pro Gln Ala Glu Gly Gln Leu Gln Trp Leu Asn Arg Arg Ala Asn
    50                  55                  60

Ala Leu Leu Ala Asn Gly Val Glu Leu Arg Asp Asn Gln Leu Val Val
65                  70                  75                  80

Pro Ser Glu Gly Leu Tyr Leu Ile Tyr Ser Gln Val Leu Phe Lys Gly
                85                  90                  95

Gln Gly Cys Pro Ser Thr His Val Leu Leu Thr His Thr Ile Ser Arg
            100                 105                 110

Ile Ala Val Ser Tyr Gln Thr Lys Val Asn Leu Leu Ser Ala Ile Lys
            115                 120                 125
```

Ser Pro Cys Gln Arg Glu Thr Pro Glu Gly Ala Glu Ala Lys Pro Trp
        130                 135                 140

Tyr Glu Pro Ile Tyr Leu Gly Gly Val Phe Gln Leu Glu Lys Gly Asp
145                 150                 155                 160

Arg Leu Ser Ala Glu Ile Asn Arg Pro Asp Tyr Leu Asp Phe Ala Glu
                165                 170                 175

Ser Gly Gln Val Tyr Phe Gly Ile Ile Ala Leu
            180                 185

<210> SEQ ID NO 71
<211> LENGTH: 564
<212> TYPE: DNA
<213> ORGANISM: Artificial Sequence
<220> FEATURE:
<223> OTHER INFORMATION: TNF-Beta10*

<400> SEQUENCE: 71
atggttcgta gcagcagtcg taccccgagc gataaaccgg ttgcacatgt tgttgcaaat      60
ccgcaggccg aaggtcagct gcagtggctg aatcgtcgtg caaatgcact gctggcaaat     120
ggtgttgaac tgcgtgataa tcagctggtt gttccgagcg aaggtctgta tctgatttat     180
agccaggttc tgtttaaagg tcagggttgt ccgagcacac atgttctgct gacccatacc     240
attagccgta ttgcagttag ctatcagacc aaagttaatc tgctgagcgc aattaaaagc     300
ccgtgtcagc gtgaaacacc ggaaggtgcc gaagcaaaac cgtggtatga accgatttat     360
cttggtggtg ttttcagct ggaaaagggt gatcgtctga gcgcagaaat taatcgtccg     420
gattatctgg attttgcaga aagcggtcag gtgtattttg cattattgc attaggtggt     480 ggtagcggtc atcatcacca ccatcaccat catggtggtg cagtggtgt gagcggttgg     540 cgtctgttca aaaaaatcag ctaa                                            564

<210> SEQ ID NO 72
<211> LENGTH: 187
<212> TYPE: PRT
<213> ORGANISM: Artificial Sequence
<220> FEATURE:
<223> OTHER INFORMATION: TNF-Beta10*

<400> SEQUENCE: 72

Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

-continued

```
Phe Ala Glu Ser Gly Gln Val Tyr Phe Gly Ile Ile Ala Leu Gly Gly
145                 150                 155                 160

Gly Ser Gly His His His His His His Gly Gly Gly Ser Gly
                165                 170                 175

Val Ser Gly Trp Arg Leu Phe Lys Lys Ile Ser
            180                 185
```

<210> SEQ ID NO 73
<211> LENGTH: 282
<212> TYPE: DNA
<213> ORGANISM: Artificial Sequence
<220> FEATURE:
<223> OTHER INFORMATION: Beta9-PpL

<400> SEQUENCE: 73

```
atgggtagta tgctgtttcg tgttaccatt aacagcggtg gtggtagcgg tcatcatcac      60
caccatcacc atcatggtgg tggcagtggt agcgaagtga ccattaaagt gaacctgatt     120
tttgcggatg gcaaaattca gaccgcagaa tttaaaggca cctttgaaga agcaacagcc     180
gaagcatatc gttatgcagc actgctggca aaagttaatg gtgaatatac cgcagatctg     240
gaagatggtg gtaatcacat gaatatcaaa ttcgcaggct aa                        282
```

<210> SEQ ID NO 74
<211> LENGTH: 93
<212> TYPE: PRT
<213> ORGANISM: Artificial Sequence
<220> FEATURE:
<223> OTHER INFORMATION: Beta9-PpL

<400> SEQUENCE: 74

```
Met Gly Ser Met Leu Phe Arg Val Thr Ile Asn Ser Gly Gly Gly Ser
1               5                   10                  15

Gly His His His His His His His Gly Gly Gly Ser Gly Ser Glu
                20                  25                  30

Val Thr Ile Lys Val Asn Leu Ile Phe Ala Asp Gly Lys Ile Gln Thr
                35                  40                  45

Ala Glu Phe Lys Gly Thr Phe Glu Glu Ala Thr Ala Glu Ala Tyr Arg
50                  55                  60

Tyr Ala Ala Leu Leu Ala Lys Val Asn Gly Glu Tyr Thr Ala Asp Leu
65                  70                  75                  80

Glu Asp Gly Gly Asn His Met Asn Ile Lys Phe Ala Gly
                85                  90
```

<210> SEQ ID NO 75
<211> LENGTH: 282
<212> TYPE: DNA
<213> ORGANISM: Artificial Sequence
<220> FEATURE:
<223> OTHER INFORMATION: PpL-Beta9

<400> SEQUENCE: 75

```
atgagcgaag tgaccattaa agtgaacctg attttttgcgg atggcaaaat tcagaccgca      60
gaatttaaag gcacctttga agaagcaaca gccgaagcat atcgttatgc agcactgctg     120
gcaaaagtta atggtgaata taccgcagat ctggaagatg gtggtaatca catgaatatc     180
aaattcgcag gcggtggtgg tagcggtcat catcaccacc atcaccatca tggtggtggc     240
agtggtggta gtatgctgtt tcgtgttacc attaacagct aa                        282
```

<210> SEQ ID NO 76

-continued

<211> LENGTH: 93
<212> TYPE: PRT
<213> ORGANISM: Artificial Sequence
<220> FEATURE:
<223> OTHER INFORMATION: PpL-Beta9

<400> SEQUENCE: 76

Met Ser Glu Val Thr Ile Lys Val Asn Leu Ile Phe Ala Asp Gly Lys
1               5                   10                  15

Ile Gln Thr Ala Glu Phe Lys Gly Thr Phe Glu Glu Ala Thr Ala Glu
            20                  25                  30

Ala Tyr Arg Tyr Ala Ala Leu Leu Ala Lys Val Asn Gly Glu Tyr Thr
        35                  40                  45

Ala Asp Leu Glu Asp Gly Gly Asn His Met Asn Ile Lys Phe Ala Gly
    50                  55                  60

Gly Gly Gly Ser Gly His His His His His His Gly Gly
65                  70                  75                  80

Ser Gly Gly Ser Met Leu Phe Arg Val Thr Ile Asn Ser
                85                  90

<210> SEQ ID NO 77
<211> LENGTH: 282
<212> TYPE: DNA
<213> ORGANISM: Artificial Sequence
<220> FEATURE:
<223> OTHER INFORMATION: Beta10-PpL

<400> SEQUENCE: 77
atggtgagcg gttggcgtct gttcaaaaaa atcagcggtg gtggtagcgg tcatcatcac      60
caccatcacc atcatggtgg tggcagtggt agcgaagtga ccattaaagt gaacctgatt     120
tttgcggatg gcaaaattca gaccgcagaa tttaaaggca cctttgaaga agcaacagcc     180
gaagcatatc gttatgcagc actgctggca aaagttaatg gtgaatatac cgcagatctg     240
gaagatggtg gtaatcacat gaatatcaaa ttcgcaggct aa                        282

<210> SEQ ID NO 78
<211> LENGTH: 93
<212> TYPE: PRT
<213> ORGANISM: Artificial Sequence
<220> FEATURE:
<223> OTHER INFORMATION: Beta10-PpL

<400> SEQUENCE: 78

Met Val Ser Gly Trp Arg Leu Phe Lys Lys Ile Ser Gly Gly Gly Ser
1               5                   10                  15

Gly His His His His His His His Gly Gly Gly Ser Gly Ser Glu
            20                  25                  30

Val Thr Ile Lys Val Asn Leu Ile Phe Ala Asp Gly Lys Ile Gln Thr
        35                  40                  45

Ala Glu Phe Lys Gly Thr Phe Glu Glu Ala Thr Ala Glu Ala Tyr Arg
    50                  55                  60

Tyr Ala Ala Leu Leu Ala Lys Val Asn Gly Glu Tyr Thr Ala Asp Leu
65                  70                  75                  80

Glu Asp Gly Gly Asn His Met Asn Ile Lys Phe Ala Gly
                85                  90

<210> SEQ ID NO 79
<211> LENGTH: 282
<212> TYPE: DNA
<213> ORGANISM: Artificial Sequence
<220> FEATURE:
<223> OTHER INFORMATION: PpL-Beta10*

<400> SEQUENCE: 79

```
atgagcgaag tgaccattaa agtgaacctg attttttgcgg atggcaaaat tcagaccgca    60
gaatttaaag gcacctttga agaagcaaca gccgaagcat atcgttatgc agcactgctg   120
gcaaaagtta atggtgaata taccgcagat ctggaagatg gtggtaatca catgaatatc   180
aaattcgcag gcggtggtgg tagcggtcat catcaccacc atcaccatca tggtggtggc   240
agtggtgtga gcggttggcg tctgttcaaa aaaatcagct aa                      282
```

<210> SEQ ID NO 80
<211> LENGTH: 93
<212> TYPE: PRT
<213> ORGANISM: Artificial Sequence
<220> FEATURE:
<223> OTHER INFORMATION: PpL-Beta10*

<400> SEQUENCE: 80

```
Met Ser Glu Val Thr Ile Lys Val Asn Leu Ile Phe Ala Asp Gly Lys
1               5                   10                  15

Ile Gln Thr Ala Glu Phe Lys Gly Thr Phe Glu Glu Ala Thr Ala Glu
            20                  25                  30

Ala Tyr Arg Tyr Ala Ala Leu Leu Ala Lys Val Asn Gly Glu Tyr Thr
        35                  40                  45

Ala Asp Leu Glu Asp Gly Gly Asn His Met Asn Ile Lys Phe Ala Gly
    50                  55                  60

Gly Gly Gly Ser Gly His His His His His His Gly Gly Gly
65                  70                  75                  80

Ser Gly Val Ser Gly Trp Arg Leu Phe Lys Lys Ile Ser
                85                  90
```

<210> SEQ ID NO 81
<211> LENGTH: 258
<212> TYPE: DNA
<213> ORGANISM: Artificial Sequence
<220> FEATURE:
<223> OTHER INFORMATION: Beta9-SpA

<400> SEQUENCE: 81

```
atgggtagta tgctgtttcg tgttaccatt aacagcggtg gtggtagcgg tcatcatcac    60
caccatcacc atcatggtgg tggcagtggt agctacaaca aagatcagca gagcgccttt   120
tatgaaattc tgaatatgcc gaatctgaat gaagcacagc gcaatggttt tattcagagc   180
ctgaaagatg atccgagcca gagcaccaat gttctgggtg aagcaaaaaa actgaatgaa   240
agccaggcac cgaaataa                                                 258
```

<210> SEQ ID NO 82
<211> LENGTH: 85
<212> TYPE: PRT
<213> ORGANISM: Artificial Sequence
<220> FEATURE:
<223> OTHER INFORMATION: Beta9-SpA

<400> SEQUENCE: 82

```
Met Gly Ser Met Leu Phe Arg Val Thr Ile Asn Ser Gly Gly Gly Ser
1               5                   10                  15

Gly His His His His His His His Gly Gly Gly Ser Gly Ser Tyr
            20                  25                  30
```

```
Asn Lys Asp Gln Gln Ser Ala Phe Tyr Glu Ile Leu Asn Met Pro Asn
        35                  40                  45

Leu Asn Glu Ala Gln Arg Asn Gly Phe Ile Gln Ser Leu Lys Asp Asp
 50                  55                  60

Pro Ser Gln Ser Thr Asn Val Leu Gly Glu Ala Lys Lys Leu Asn Glu
 65                  70                  75                  80

Ser Gln Ala Pro Lys
             85

<210> SEQ ID NO 83
<211> LENGTH: 258
<212> TYPE: DNA
<213> ORGANISM: Artificial Sequence
<220> FEATURE:
<223> OTHER INFORMATION: SpA-Beta9

<400> SEQUENCE: 83
atgagctaca acaaagatca gcagagcgcc ttttatgaaa ttctgaatat gccgaatctg      60
aatgaagcac agcgcaatgg ttttattcag agcctgaaag atgatccgag ccagagcacc     120
aatgttctgg gtgaagcaaa aaaactgaat gaaagccagg caccgaaagg tggtggtagc     180
ggtcatcatc accaccatca ccatcatggt ggtggcagtg gtggtagtat gctgtttcgt     240
gttaccatta acagctaa                                                   258

<210> SEQ ID NO 84
<211> LENGTH: 85
<212> TYPE: PRT
<213> ORGANISM: Artificial Sequence
<220> FEATURE:
<223> OTHER INFORMATION: SpA-Beta9

<400> SEQUENCE: 84

Met Ser Tyr Asn Lys Asp Gln Gln Ser Ala Phe Tyr Glu Ile Leu Asn
 1               5                  10                  15

Met Pro Asn Leu Asn Glu Ala Gln Arg Asn Gly Phe Ile Gln Ser Leu
             20                  25                  30

Lys Asp Asp Pro Ser Gln Ser Thr Asn Val Leu Gly Glu Ala Lys Lys
         35                  40                  45

Leu Asn Glu Ser Gln Ala Pro Lys Gly Gly Gly Ser Gly His His His
 50                  55                  60

His His His His Gly Gly Gly Ser Gly Gly Ser Met Leu Phe Arg
 65                  70                  75                  80

Val Thr Ile Asn Ser
             85

<210> SEQ ID NO 85
<211> LENGTH: 258
<212> TYPE: DNA
<213> ORGANISM: Artificial Sequence
<220> FEATURE:
<223> OTHER INFORMATION: Beta10*-SpA

<400> SEQUENCE: 85
atggtgagcg ttggcgtct gttcaaaaaa atcagcggtg gtggtagcgg tcatcatcac      60
caccatcacc atcatggtgg tggcagtggt agctacaaca aagatcagca gagcgccttt    120
tatgaaattc tgaatatgcc gaatctgaat gaagcacagc gcaatggttt tattcagagc    180
ctgaaagatg atccgagcca gagcaccaat gttctgggtg aagcaaaaaa actgaatgaa    240
agccaggcac cgaaataa                                                   258
```

<210> SEQ ID NO 86
<211> LENGTH: 85
<212> TYPE: PRT
<213> ORGANISM: Artificial Sequence
<220> FEATURE:
<223> OTHER INFORMATION: Beta10*-SpA

<400> SEQUENCE: 86

Met Val Ser Gly Trp Arg Leu Phe Lys Lys Ile Ser Gly Gly Gly Ser
1               5                   10                  15

Gly His His His His His His His Gly Gly Gly Ser Gly Ser Tyr
            20                  25                  30

Asn Lys Asp Gln Gln Ser Ala Phe Tyr Glu Ile Leu Asn Met Pro Asn
        35                  40                  45

Leu Asn Glu Ala Gln Arg Asn Gly Phe Ile Gln Ser Leu Lys Asp Asp
    50                  55                  60

Pro Ser Gln Ser Thr Asn Val Leu Gly Glu Ala Lys Lys Leu Asn Glu
65                  70                  75                  80

Ser Gln Ala Pro Lys
            85

<210> SEQ ID NO 87
<211> LENGTH: 258
<212> TYPE: DNA
<213> ORGANISM: Artificial Sequence
<220> FEATURE:
<223> OTHER INFORMATION: SpA-Beta10*

<400> SEQUENCE: 87
atgagctaca acaaagatca gcagagcgcc ttttatgaaa ttctgaatat gccgaatctg        60
aatgaagcac agcgcaatgg tttttattcag agcctgaaag atgatccgag ccagagcacc      120
aatgttctgg gtgaagcaaa aaaactgaat gaaagccagg caccgaaagg tggtggtagc      180
ggtcatcatc accaccatca ccatcatggt ggtggcagtg gtgtgagcgg ttggcgtctg      240
ttcaaaaaaa tcagctaa                                                     258

<210> SEQ ID NO 88
<211> LENGTH: 85
<212> TYPE: PRT
<213> ORGANISM: Artificial Sequence
<220> FEATURE:
<223> OTHER INFORMATION: SpA-Beta10*

<400> SEQUENCE: 88

Met Ser Tyr Asn Lys Asp Gln Gln Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Asp Asp Pro Ser Gln Ser Thr Asn Val Leu Gly Glu Ala Lys Lys
        35                  40                  45

Leu Asn Glu Ser Gln Ala Pro Lys Gly Gly Gly Ser Gly His His His
    50                  55                  60

His His His His Gly Gly Gly Ser Gly Val Ser Gly Trp Arg Leu
65                  70                  75                  80

Phe Lys Lys Ile Ser
            85

<210> SEQ ID NO 89

```
<211> LENGTH: 267
<212> TYPE: DNA
<213> ORGANISM: Artificial Sequence
<220> FEATURE:
<223> OTHER INFORMATION: Beta9-SpGA1

<400> SEQUENCE: 89
atgggtagta tgctgtttcg tgttaccatt aacagcggtg gtggtagcgg tcatcatcac      60
caccatcacc atcatggtgg tggcagtggt gcagtgacca cctataaact ggttattaat     120
ggtcgtaccc tgagcggtta taccaccacc accgcagttg atgcagaaac cgcagaaaaa     180
gcatttaaac agtatgccta tgtgcatgaa gttgatggtg tttggaccta tgatgatgca     240
accaaaacct ttaccgttac cgaataa                                          267

<210> SEQ ID NO 90
<211> LENGTH: 88
<212> TYPE: PRT
<213> ORGANISM: Artificial Sequence
<220> FEATURE:
<223> OTHER INFORMATION: Beta9-SpGA1

<400> SEQUENCE: 90

Met Gly Ser Met Leu Phe Arg Val Thr Ile Asn Ser Gly Gly Gly Ser
1               5                   10                  15

Gly His His His His His His His Gly Gly Gly Ser Gly Ala Val
            20                  25                  30

Thr Thr Tyr Lys Leu Val Ile Asn Gly Arg Thr Leu Ser Gly Tyr Thr
        35                  40                  45

Thr Thr Thr Ala Val Asp Ala Glu Thr Ala Glu Lys Ala Phe Lys Gln
    50                  55                  60

Tyr Ala Tyr Val His Glu Val Asp Gly Val Trp Thr Tyr Asp Asp Ala
65                  70                  75                  80

Thr Lys Thr Phe Thr Val Thr Glu
                85

<210> SEQ ID NO 91
<211> LENGTH: 267
<212> TYPE: DNA
<213> ORGANISM: Artificial Sequence
<220> FEATURE:
<223> OTHER INFORMATION: SpGA1-Beta9

<400> SEQUENCE: 91
atggcagtga ccacctataa actggttatt aatggtcgta ccctgagcgg ttataccacc      60
accaccgcag ttgatgcaga aaccgcagaa aaagcattta acagtatgcc tatgtgcat     120 gaagttgatg gtgtttggac ctatgatgat gcaaccaaaa cctttaccgt taccgaaggt     180
ggtggtagcg gtcatcatca ccaccatcac catcatggtg gtggcagtgg tggtagtatg     240
ctgtttcgtg ttaccattaa cagctaa                                          267

<210> SEQ ID NO 92
<211> LENGTH: 88
<212> TYPE: PRT
<213> ORGANISM: Artificial Sequence
<220> FEATURE:
<223> OTHER INFORMATION: SpGA1-Beta9

<400> SEQUENCE: 92

Met Ala Val Thr Thr Tyr Lys Leu Val Ile Asn Gly Arg Thr Leu Ser
1               5                   10                  15
```

```
Gly Tyr Thr Thr Thr Thr Ala Val Asp Ala Glu Thr Ala Glu Lys Ala
                20                  25                  30

Phe Lys Gln Tyr Ala Tyr Val His Glu Val Asp Gly Val Trp Thr Tyr
            35                  40                  45

Asp Asp Ala Thr Lys Thr Phe Thr Val Thr Glu Gly Gly Ser Gly
        50                  55                  60

His His His His His His His Gly Gly Gly Ser Gly Gly Ser Met
65                  70                  75                  80

Leu Phe Arg Val Thr Ile Asn Ser
                85
```

<210> SEQ ID NO 93
<211> LENGTH: 267
<212> TYPE: DNA
<213> ORGANISM: Artificial Sequence
<220> FEATURE:
<223> OTHER INFORMATION: Beta10*-SpGA1

<400> SEQUENCE: 93

```
atggtgagcg gttggcgtct gttcaaaaaa atcagcggtg gtggtagcgg tcatcatcac    60
caccatcacc atcatggtgg tggcagtggt gcagtgacca cctataaact ggttattaat   120
ggtcgtaccc tgagcggtta taccaccacc accgcagttg atgcagaaac cgcagaaaaa   180
gcatttaaac agtatgccta tgtgcatgaa gttgatggtg tttggaccta tgatgatgca   240 accaaaaacct ttaccgttac cgaataa                                        267
```

<210> SEQ ID NO 94
<211> LENGTH: 88
<212> TYPE: PRT
<213> ORGANISM: Artificial Sequence
<220> FEATURE:
<223> OTHER INFORMATION: Beta10*-SpGA1

<400> SEQUENCE: 94

```
Met Val Ser Gly Trp Arg Leu Phe Lys Lys Ile Ser Gly Gly Gly Ser
1               5                   10                  15

Gly His His His His His His His Gly Gly Gly Ser Gly Ala Val
                20                  25                  30

Thr Thr Tyr Lys Leu Val Ile Asn Gly Arg Thr Leu Ser Gly Tyr Thr
            35                  40                  45

Thr Thr Thr Ala Val Asp Ala Glu Thr Ala Glu Lys Ala Phe Lys Gln
        50                  55                  60

Tyr Ala Tyr Val His Glu Val Asp Gly Val Trp Thr Tyr Asp Asp Ala
65                  70                  75                  80

Thr Lys Thr Phe Thr Val Thr Glu
                85
```

<210> SEQ ID NO 95
<211> LENGTH: 267
<212> TYPE: DNA
<213> ORGANISM: Artificial Sequence
<220> FEATURE:
<223> OTHER INFORMATION: SpGA1-Beta10

<400> SEQUENCE: 95

```
atggcagtga ccacctataa actggttatt aatggtcgta ccctgagcgg ttataccacc    60
accaccgcag ttgatgcaga aaccgcagaa aaagcattta acagtatgcc tatgtgcat   120 gaagttgatg gtgtttggac ctatgatgat gcaaccaaaa cctttaccgt taccgaaggt   180
```

```
ggtggtagcg gtcatcatca ccaccatcac catcatggtg gtggcagtgg tgtgagcggt    240
tggcgtctgt tcaaaaaaat cagctaa                                         267

<210> SEQ ID NO 96
<211> LENGTH: 88
<212> TYPE: PRT
<213> ORGANISM: Artificial Sequence
<220> FEATURE:
<223> OTHER INFORMATION: SpGA1-Beta10*

<400> SEQUENCE: 96

Met Ala Val Thr Thr Tyr Lys Leu Val Ile Asn Gly Arg Thr Leu Ser
1               5                   10                  15

Gly Tyr Thr Thr Thr Thr Ala Val Asp Ala Glu Thr Ala Glu Lys Ala
            20                  25                  30

Phe Lys Gln Tyr Ala Tyr Val His Glu Val Asp Gly Val Trp Thr Tyr
        35                  40                  45

Asp Asp Ala Thr Lys Thr Phe Thr Val Thr Glu Gly Gly Gly Ser Gly
    50                  55                  60

His His His His His His His Gly Gly Gly Ser Gly Val Ser Gly
65                  70                  75                  80

Trp Arg Leu Phe Lys Lys Ile Ser
                85
```

TARGET-BINDING ACTIVATED SPLIT REPORTER SYSTEMS FOR ANALYTE DETECTION AND RELATED COMPONENTS AND METHODS

RELATED APPLICATIONS

This application claims the benefit of U.S. Provisional Application No. 62/327,920, filed on Apr. 26, 2016 and titled "TARGET-BINDING ACTIVATED SPLIT REPORTER SYSTEMS FOR ANALYTE DETECTION AND RELATED COMPONENTS AND METHODS," which is hereby incorporated by reference in its entirety.

TECHNICAL FIELD

The present disclosure relates generally to the fields of biotechnology and analyte detection. More particularly, the present disclosure relates to split reporters, such as split reporter proteins that are configured to bind to and facilitate detection of an analyte or analytes in a mixture.

BACKGROUND

Modern research and medicine involve qualitatively assessing and/or quantitatively measuring one or more analytes in a mixture. For example, in research settings, the identification and quantification of biomolecules, such as proteins, nucleic acids, sugars, lipids, etc., is important to understanding the mechanistic underpinnings of cellular processes. In clinical settings, the detection of biomarkers can enable the diagnosis of a disease, facilitate a more accurate prognosis for the patient, and/or provide a mechanism for monitoring therapeutic outcomes. As such, the ability to accurately and reliably detect analytes (e.g., biomolecules) in a timely manner is highly important.

For decades, researchers have relied on various immunoassays, such as ELISAs, western blots, immunocytochemistry, and/or immunohistochemistry for biomolecule (e.g., protein) detection. Such immunoassays may be time-consuming (e.g., >6 hours) and labor-intensive. One factor contributing to the labor and time required for some immunoassays is the need to remove excess (i.e., unbound) antibodies. For example, some immunoassays require numerous wash steps before and after addition of a primary antibody and a secondary antibody. Some immunoassays additionally or alternatively require one or more blocking steps and/or immobilization of the analyte. Some immunoassays cannot be carried out in a homogeneous solution.

Split proteins have been used for the detection and/or quantification of protein interactions. Various names have been given to the processes used for such detection and/or quantification, such as protein-fragment complementation assays (Michnick et al., *Nat Rev Drug Discov* 6, 569-82 (2007); Remy & Michnick, *Methods Mol Biol* 1278, 467-81 (2015)), split protein complementation (Shekhawat & Ghosh, *Curr Opin Chem Biol* 15, 789-97 (2011)), or bimolecular fluorescence complementation (Miller et al., *J Mol Biol* 427, 2039-55 (2015); Kerppola, T. K., *Chem Soc Rev* 38, 2876-2886 (2009)). In these split protein systems, each fragment of the split protein is individually inactive. However, when the fragments of a split protein are combined at high concentrations, the fragments can form an active protein complex. This ability to turn on the activity of the split protein can be exploited to monitor protein interactions by fusing each peptide fragment of the split protein to different proteins that have affinity for one another. The interaction between these different proteins creates a high local concentration of the two peptide fragments, thereby causing the separate fragments of the split protein to bind to one another to form an active protein complex.

Several split proteins have been used in complementation assays, including β-lactamase, β-galactosidase, dihydrofolate reductase, green fluorescent protein, ubiquitin, and TEV protease (Morrell et al., *FEBS Lett* 583, 1684-91 (2009). One split protein that has been used to detect and quantify protein interactions is NanoBiT® (Promega®). NanoBiT® is a split and modified form of NanoLuc® (Promega®), an engineered luciferase derived from a deep sea luminous shrimp (Dixon et al., *ACS Chem Biol* 11, 400-08 (2016)). The split NanoBiT® enzyme includes a relatively short peptide fragment (11 amino acids) and a relatively long peptide fragment (an 18 kDa polypeptide).

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
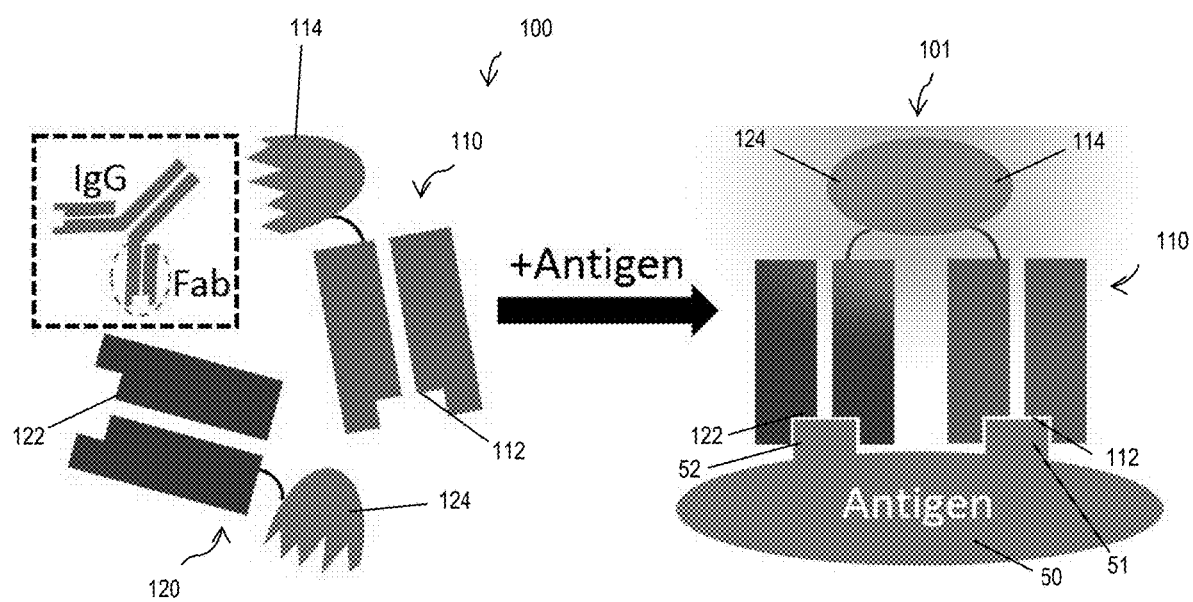
FIG. 1 is a schematic representation of components of a target-binding activated split reporter system.

The following detailed description of various embodiments is not intended to limit the scope of the disclosure, but is merely representative of various embodiments. The present disclosure relates generally to split reporter systems, including split reporter systems for use in detecting and/or measuring an analyte.

"Enzymatic activity" includes the catalytic activity of a complex formed by fragment complementation. A "homomultimeric protein complex" includes homodimers, homotrimers, homotetramers, etc. A "heteromultimeric protein complex" includes heterodimers, heterotrimers, heterotetramers, etc. The term "domain" is not limited to protein domains. The term "peptide" or "peptide fragment" can refer to any chain of amino acids, regardless of length.

Immunoassays can be used to detect and/or quantify an analyte, such as a biomolecule. Many immunoassays require labor-intensive, time-consuming, multi-step protocols in order to remove unbound or non-specific targeting domains, thereby enabling specific detection due to binding of the analyte. Certain embodiments disclosed herein may provide advantages over known immunoassays, such as by decreasing the amount of labor (and thereby reducing the potential for human error), decreasing the time involved, decreasing the number of steps required to obtain a specific and/or measurable signal, and/or enabling detection/quantification under conditions that are not feasible with known immunoassays. Some embodiments can be used to monitor the presence, level, location, change in level, or change in location of an analyte.

Some embodiments disclosed herein involve the use of a split reporter protein, which may also be referred to as a split reporter or a split reporter protein complex. In some embodiments, the split reporter is a binary (i.e., two-part) reporter. In other embodiments, the split reporter is a ternary (i.e., three-part or tripartite) reporter. The individual fragments of the split reporter may be individually inactive. However, when combined with complementary peptide fragment(s) of the split reporter, the peptide fragments may bind to one another to form an active protein complex. Examples of split reporter proteins include split green fluorescent protein (Cabantous et al., Sci Rep 3, 2854 (2013)), NanoBiT®, and split β-lactamase. In some embodiments, the split reporter protein does not include a cysteine residue.

In some embodiments, the split reporter protein is a beta-barrel protein, such as a 10-stranded beta-barrel protein. In some embodiments, the split reporter protein is a split fluorescent protein, such as a split green fluorescent protein (e.g., a binary split fluorescent protein or a ternary split fluorescent protein). In other embodiments, the split reporter protein is a split enzyme. The split enzyme may catalyze the conversion of a substrate to a product. The activity of the split enzyme on the substrate may result in the emission of a detectable (e.g., luminescent) signal. For example, in some embodiments, the split enzyme is a split luciferase. In some embodiments, the substrate for the split enzyme is luciferin, furimazine, or some other luminogenic substrate or molecule. In some embodiments, the split enzyme catalyzes the conversion of furimazine to furimamide. In some embodiments, the enzymatic activity of the split enzyme is not natively found in mammals. In some embodiments, the split enzyme has no eukaryotic ortholog.

In some embodiments, the split reporter protein is a three-part (i.e., tripartite or ternary) complex that includes a first agent, a second agent, and a third agent. The first agent may include a first targeting domain and a first peptide fragment of a split reporter protein. The second agent may include a second targeting domain and a second peptide fragment of the split reporter protein. The third agent may include a third fragment of the split reporter protein.

The targeting domains of the first agent and the second agent may be any suitable targeting domain. For example, in some embodiments, the targeting domains of one or both of the first agent and the second agent comprise or consist of an antibody, an antigen, a designed ankyrin repeat protein (DARPin), an affibody, ubiquitin, a known interaction partner, a ligand, an aptamer, adnectin (monobody or Fibronectin type II domain), or a portion thereof. For example, in some embodiments, the targeting domains of one or both of the first agent and the second agent may be a fragment antigen binding fragment (Fab), a single-chain variable fragment, IgG, etc. In some embodiments, one or more targeting domains are monoclonal antibodies or portions thereof. In some embodiments, one or both targeting domains are polyclonal antibodies, or portions thereof. In some embodiments, one or more targeting domains are immunoglobulin-binding proteins, such as protein A, protein G, protein A/G, or protein L.

The first targeting domain may be configured to selectively bind to a first target region of an analyte, and the second targeting domain may be configured to selectively bind to a second target region of the analyte. For example, a first targeting domain may be configured to selectively bind to a first epitope of an analyte, while the second targeting domain is configured to selectively bind to a second epitope of the analyte. In some embodiments, the first target region and the second target region are different in structure (e.g., different epitopes). In other embodiments, the first target region and the second target region are identical or substantially identical in structure (e.g., identical or substantially identical epitopes), but are located at separate sites on the analyte (e.g., the protein). In some embodiments, the first target region and the second target region are separated by less than 300 (e.g., less than 150) angstroms. For example, in some embodiments, the first target region is separated from the second target region by 2-300 angstroms, 2-200 angstroms, 2-175 angstroms, 2-150 angstroms, 2-125 angstroms, 2-100 angstroms, 2-75 angstroms, 2-50 angstroms, 2-25 angstroms; 25-300 angstroms, 50-300 angstroms, 75-300 angstroms, 100-300 angstroms, 125-300 angstroms, 150-300 angstroms, 10-150 angstroms; 25-145 angstroms; 35-145 angstroms, 40-145 angstroms, 50-125 angstroms, or 60-100 angstroms. In some embodiments, the first and second target regions (e.g., epitopes) do not overlap.

The first peptide fragment and the second peptide fragment may be relatively short peptide fragments. Stated differently, one or both of the first peptide fragment and the second peptide fragment may have a mass of less than about 3 kDa. In some embodiments, the first peptide fragment is less than or equal to 15, 14, 13, 12, and/or 11 amino acids in length. In some embodiments, the second peptide fragment is less than or equal to 15, 14, 13, 12, and/or 11 amino acids in length. For example, in some embodiments, both the first peptide fragment and the second peptide fragment are each 11 amino acids in length. The relatively short length of the peptide fragments may facilitate expression, reduce aggregation, improve solubility, and/or improve the stability of agents that are produced as fusion proteins. Such small peptide fragments may also be less likely to interfere with binding of the targeting domain to the analyte.

In some embodiments, the first peptide fragment has at least 80%, 90%, or 100% sequence identity to the sequence of SEQ ID NO 1 (i.e., VSGWRLFKKIS). In some embodiments, the second peptide fragment has at least 80%, 90%, or 100% sequence identity to the sequence of SEQ ID NO 2 (i.e., GSMLFRVTINS).

In some embodiments, the first peptide fragment corresponds with a C-terminal beta sheet (β10) of a 10-stranded beta-barrel protein. In some embodiments, the second peptide fragment corresponds with the ninth beta sheet of a 10-stranded beta-barrel protein. In some embodiments, the first targeting domain of the first agent is positioned on the N-terminal side of a β10 fragment. In other embodiments, the first targeting domain of the first agent is positioned on the C-terminal side of a β10 fragment. In some embodiments, the second targeting domain of the second agent is positioned on the N-terminal side of a fragment corresponding to the ninth beta sheet. In other embodiments, the second targeting domain of the second agent is positioned on the C-terminal side of a fragment corresponding to the ninth beta sheet. In some embodiments, the peptide fragment and the targeting domain are connected via a linker. In some embodiments, the linker is a peptide. In other embodiments, the linker is not a peptide.

In some embodiments, one or both of the first agent and the second agent are recombinant fusion proteins. In some embodiments, the fusion proteins include a solubilizing protein or domain (e.g., HaloTag®, (Promega)). In other embodiments, one or both of the first agent and the second agent are formed by synthetically conjugating or enzymatically ligating a peptide fragment to a targeting domain. Such conjugation may facilitate the use of polyclonal antibodies or antibodies from hybridomas where the sequence of the targeting domain is not known. In some embodiments, a peptide fragment is conjugated to a targeting domain via an exposed sulfide (e.g., a cysteine residue) or an exposed amine (e.g., a lysine residue) on the targeting domain. In some embodiments, the targeting domain is modified to include a sulfhydryl group. For example, in some embodiments, 2-iminothiolane is used to modify a primary amine of a targeting domain to form an exposed sulfhydryl group. In some embodiments, a maleimide may be used to attach a peptide fragment to an exposed sulfhydryl group on a targeting domain (e.g., an antibody).

In some embodiments that include a third peptide fragment, the third peptide fragment has a mass of between 16 kDa and 17 kDa. In some embodiments, the third peptide fragment has at least 70%, 80%, 90%, 95% or 100% sequence identity to the sequence of SEQ ID NO 3. In some embodiments, the third peptide fragment has between 140 and 150 amino acids. For example, in some embodiments, the third peptide has between 145 and 150 amino acids (e.g., 148 amino acids).

The analyte to be detected and/or measured may be any suitable analyte. In some embodiments, the analyte is a biomolecule, such as a protein, nucleic acid, carbohydrate, or lipid. In some embodiments, the analyte has a monomeric quaternary structure (i.e., the analyte is not a dimer, trimer, etc.). In other embodiments, the analyte has a higher quaternary structure. For example, the analyte may be a dimer, a trimer, a tetramer, or any other multimeric complex. In some embodiments, the analyte is a modified protein, such as a phosphorylated protein, a glycosylated protein, or an antibody-drug conjugate (e.g., trastuzumab emtansine (Kadcyla®) or brentuximab vedotin (Adcetris®)). In some embodiments, the analyte is an antibody, such as a natural, synthetic, or recombinant antibody (or a portion thereof). In some embodiments, the analyte is an antibody formed in response to an allergen, a bacterial infection, or a viral infection.

As noted above, in some embodiments, the analyte is a monomeric protein. In some embodiments, the monomeric protein may have a first target region and a second target region that are different structures (e.g., epitopes) on the monomeric protein. In other words, the first target region and the second target region of the monomeric protein may be significantly different in structure. In other embodiments, the monomeric protein may have a first target region and a second target region that are substantially identical epitopes located at separate sites on the monomeric protein.

In some embodiments, the analyte is a multimeric protein complex. The multimeric protein complex may be a homomultimeric protein complex or a heteromultimeric protein complex. In some embodiments in which the analyte is a multimeric protein complex, the first targeting domain and the second targeting domain bind to adjacent proteins of the multimeric protein complex. Because the split reporter produces a signal only when the peptide fragments are in proximity to one another, the split reporter may be used to assess complex formation. Stated differently, split reporter systems that include both (1) a first peptide fragment that is attached to a first targeting domain that binds a first protein of a protein complex and (2) a second peptide fragment that is attached to a second targeting domain that binds to a second protein of a protein complex may be used to identify and/or quantify complex formation.

In some embodiments, the analyte is a soluble protein or biomolecule. For example, in some embodiments the analyte is a naturally occurring, endogenous, or xenobiotic protein or biomolecule. In some embodiments, the analyte is a growth factor, cytokine, hormone, a growth factor receptor, a cytokine receptor, or a hormone receptor. For example, the analyte may be selected from any of the following: adrenomedullin (AM), angiopoietin (Ang), autocrine motility factor, bone morphogenetic proteins (BMPs), ciliary neurotrophic factor family, ciliary neurotrophic factor (CNTF), leukemia inhibitory factor (LIF), interleukin-6 (IL-6), colony-stimulating factors, macrophage colony-stimulating factor (m-CSF), granulocyte colony-stimulating factor (G-CSF), granulocyte macrophage colony-stimulating factor (GM-CSF), epidermal growth factor (EGF), ephrins, ephrin A1, ephrin A2, ephrin A3, ephrin A4, ephrin A5, ephrin B1, ephrin B2, ephrin B3, erythropoietin (EPO), fibroblast growth factor (FGF) foetal bovine somatotrophin (FBS), a ligand from the GDNF family, glial cell line-derived neurotrophic factor (GDNF), neurturin, persephin, artemin, growth differentiation factor-9 (GDF9), hepatocyte growth factor (HGF), hepatoma-derived growth factor (HDGF), insulin, insulin-like growth factors, insulin-like growth factor-1 (IGF-1), insulin-like growth factor-2 (IGF-2), interleukins, IL-1, IL-2, IL-3, IL-4, IL-5, IL-6, IL-7, keratinocyte growth factor (KGF), migration-stimulating factor (MSF), macrophage-stimulating protein (also known as hepatocyte growth factor-like protein (HGFLP)), myostatin (GDF-8), neuregulins, neuregulin 1 (NRG1), neuregulin 2 (NRG2), neuregulin 3 (NRG3), neuregulin 4 (NRG4), neurotrophins, brain-derived neurotrophic factor (BDNF), nerve growth factor (NGF), neurotrophin-3 (NT-3), neurotrophin-4 (NT-4), placental growth factor (PGF), platelet-derived growth factor (PDGF), renalase (RNLS), T-cell growth factor (TCGF), thrombopoietin (TPO), transforming growth factors, transforming growth factor alpha (TGF-α), transforming growth factor beta (TGF-β), tumor necrosis factor (also known as tumor necrosis factor alpha (TNF-α)), vascular endothelial growth factor (VEGF), amylin (or islet amyloid polypeptide), anti-Müllerian hormone (or Müllerian-inhibiting factor or hormone), adiponectin, adrenocorticotropic hormone (or corticotropin), angiotensinogen, angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, osteocalcin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, and calcitriol (1,25-dihydroxyvitamin D3).

In some embodiments, the analyte is a natural, synthetic, or recombinant immunoglobulin antibody (including a natural, synthetic, or recombinant antibody, or a portion thereof), an antibody fragment, or a derivative thereof. In some embodiments, the analyte is selected from any of the following: IgA, IgD, IgE, IgG, IgM, IgY, IgW, Vh, Vhh, a DARPin, a single-chain variable fragment (scFv), a monobody, a diabody, or a portion thereof.

In some embodiments, the analyte includes or consists of DNA or RNA, such as a polynucleotide formed from DNA, RNA, or a combination of DNA and RNA.

In some embodiments, the analyte is a biological product or biosimilar. In some embodiments, the analyte is selected from any of the following: abatacept, abciximab, abobotulinumtoxinA, adalimumab, adalimumab-atto, ado-trastuzumab emtansine, aflibercept, agalsidase beta, albiglutide, aldesleukin, alemtuzumab, alglucosidase alfa, alglucosidase alfa, alirocumab, alteplase, cathflo activase, anakinra, asfotase alfa, asparaginase, asparaginase erwinia chrysanthemi, atezolizumab, basiliximab, becaplerm in, belatacept, belimumab, bevacizumab, bezlotoxumab, blinatumomab, brentuximab vedotin, canakinumab, capromab pendetide, certolizumab pegol, cetuximab, collagenase, collagenase *clostridium histolyticum*, daclizumab, daclizumab, daratumumab, darbepoetin alfa, denileukin diftitox, denosumab, dinutuximab, dornase alfa, dulaglutide, ecallantide, eculizumab, elosulfase alfa, elotuzumab, Empliciti, epoetin alfa, etanercept, etanercept-szzs, evolocumab, filgrastim, filgrastim-sndz, galsulfase, glucarpidase, golimumab, ibritumomab tiuxetan, idarucizumab, idursulfase, incobotulinumtoxinA, infliximab, infliximab-dyyb, interferon alfa-2b, interferon alfa-n3, interferon beta-1a, interferon beta-1b, interferon beta-1, interferon gamma-1b, ipilimumab, ixekizumab, laronidase, mepolizumab, methoxy polyethylene glycol-epoetin beta, metreleptin, natalizumab, necitumumab, nivolumab, obiltoxaximab, obinutuzumab, ocriplasmin, ofatumumab, olaratumab, omalizumab, onabotulinumtoxinA, oprelvekin, palifermin, palivizumab, panitumumab, parathyroid hormone, pegaspargase, pegfilgrastim, peginterferon alfa-2a, peginterferon alfa-2b, peginterferon beta-1a, pegloticase, pembrolizumab, pertuzumab, ramucirumab, ranibizumab, rasburicase, raxibacumab, reslizumab, reteplase, rilonacept, rimabotulinumtoxinB, rituximab, romiplostim, sargramostim, sebelipase alfa, secukinumab, siltuximab, tbo-filgrastim, tenecteplase, tocilizumab, tocilizumab, trastuzumab, ustekinumab, vedolizumab, or ziv-aflibercept.

In some embodiments, the analyte is a therapeutic monoclonal antibody. For example, in some embodiments, the analyte is selected from any of the following monoclonal antibodies: abciximab (e.g., ReoPro), a chimeric antibody that targets and inhibits glycoprotein IIb/IIIa, and is used for the treatment of cardiovascular disease; adalimumab (e.g., Humira), a human antibody that inhibits tumor necrosis factor alpha (TNF-α) signaling, and is used for the treatment of rheumatoid arthritis, psoriatic arthritis, ankylosing spondylitis, Crohn's disease, ulcerative colitis, chronic psoriasis, hidradenitis suppurativa, and juvenile idiopathic arthritis; alemtuzumab (e.g., Campath), a humanized antibody that targets CD52, and is used for the treatment of chronic lymphocytic leukemia; basiliximab (e.g., Simulect), a chimeric antibody that targets the interleukin-2 receptor alpha chain (CD25), and is used for the treatment of transplant rejection; belimumab (e.g., Benlysta), a human antibody that targets and inhibits B-cell activating factor, and is used for the treatment of systemic lupus erythematosus; bevacizumab (e.g., Avastin), a humanized antibody that targets vascular endothelial growth factor (VEGF), and is used for the treatment of colorectal cancer, certain lung cancers, renal cancers, ovarian cancers, glioblastoma multiforme of the brain, and age related macular degeneration (off-label); brentuximab vedotin (e.g., Adcetris), a chimeric antibody that targets CD30, and is used for the treatment of anaplastic large cell lymphoma (ALCL) and Hodgkin lymphoma; canakinumab (e.g., Ilaris), a human antibody that targets interleukin 1β (IL-1β), and is used for the treatment of cryopyrin-associated periodic syndrome (CAPS); cetuximab (e.g., Erbitux), a chimeric antibody that targets epidermal growth factor receptor (EGFR), and is used for the treatment of colorectal cancer and head and neck cancer; certolizumab pegol (e.g., Cimzia), a humanized antibody that targets and inhibits TNF-α signaling, and is used for the treatment of Crohn's disease; daclizumab (e.g., Zenapax), a humanized antibody that targets interleukin-2 receptor alpha chain (CD25), and is used for the treatment of transplant rejection; daratumumab (e.g., Darzalex), a human antibody that targets CD38, and is used for the treatment of multiple myeloma; denosumab (e.g., Prolia and Xgeva), a human antibody that targets RANK ligand inhibitor, and is used for the treatment of postmenopausal osteoporosis and solid tumor bony metasteses; eculizumab (e.g., Soliris), a humanized antibody that targets complement system protein C5, and is used for the treatment of paroxysmal nocturnal hemoglobinuria; efalizumab (e.g., Raptiva), a humanized antibody that targets CD11a, and is used for the treatment of psoriasis; golimumab (e.g., Simponi), a human antibody that targets TNF-α inhibitor, and is used for the treatment of rheumatoid arthritis, psoriatic arthritis and ankylosing spondylitis; ibritumomab tiuxetan (e.g., Zevalin), a murine antibody that targets CD20, and is used for the treatment of non-Hodgkin lymphoma (in combination with yttrium-90 or indium-111); infliximab (e.g., Remicade), a chimeric antibody that targets and inhibits TNF-α signaling, and is used for the treatment of Crohn's disease, ulcerative colitis, psoriasis, psoriatic arthritis, ankylosing spondylitis and rheumatoid arthritis; ipilimumab (MDX-101) (e.g., Yervoy), a human antibody that targets and blocks CTLA-4, and is used for the treatment of melanoma; muromonab-CD3 (e.g., Orthoclone OKT3), a murine antibody that targets T cell CD3 receptor, and is used for the treatment of transplant rejection; natalizumab (e.g., Tysabri), a humanized antibody that targets alpha-4 integrin, and is used for the treatment of multiple sclerosis and Crohn's disease; nivolumab (e.g., Opdivo), a human antibody that targets and blocks programmed cell death protein 1 (PD-1), and is used for the treatment of melanoma and squamous-cell carcinoma of the lung; ofatumumab (e.g., Arzerra), a human antibody that targets CD20, and is used for the treatment of chronic lymphocytic leukemia; omalizumab (e.g., Xolair), a humanized antibody that targets immunoglobulin E (IgE), and is used for the treatment of mainly allergy-related asthma; palivizumab (e.g., Synagis), a humanized antibody that targets an epitope of the RSV F-protein, and is used for the treatment of respiratory syncytial virus; panitumumab (e.g., Vectibix), a human antibody that targets epidermal growth factor receptor (EGFR), and is used for the treatment of colorectal cancer; pembrolizumab (e.g., Keytruda), a humanized antibody that targets the programmed cell death 1 (PD-1) receptor, and is used for the treatment of melanoma and non-small cell lung cancer; ranibizumab (e.g., Lucentis), a humanized antibody that targets vascular endothelial growth factor A (VEGF-A), and is used for the treatment of macular degeneration; rituximab (e.g., Rituxan and Mabthera), a chimeric antibody that targets CD20, and is used for the treatment of non-Hodgkin lymphoma; tocilizumab or atlizumab (e.g., Actemra or RoActemra), a humanized antibody that targets interleukin 6 receptor (IL-6R), and is used for the treatment of rheumatoid arthritis and systemic juvenile idiopathic arthritis; tositumomab (e.g., Bexxar), a murine antibody that targets CD20, and is used for the treatment of non-Hodgkin lymphoma; trastuzumab (e.g., Herceptin), a humanized antibody that targets receptor tyrosine-protein kinase erbB-2 (ErbB2) or CD340, and is used for the treatment of breast cancer; ustekinumab (e.g., Stelara), a human antibody that targets interleukin 12 (IL-12) and interleukin 23 (IL-23), and is used for the treatment of psoriatic arthritis and plaque psoriasis; and vedolizumab (e.g., Entyvio), a humanized antibody that targets integrin α4β7, and is used for the treatment of Crohn's disease and ulcerative colitis.

In some embodiments, the analyte may be a cell surface protein or biomolecule, or be bound to a membrane of a cell. For example, in some embodiments, the analyte is a cell-surface marker and/or a cell-surface receptor. In some embodiments, the analyte is selected from any of the following: adrenergic receptor, olfactory receptors, receptor tyrosine kinases, epidermal growth factor receptor, insulin receptor, fibroblast growth factor receptors, high affinity neurotrophin receptors, ephrin receptors, integrins, low affinity nerve growth factor receptor, NMDA receptor, or immune receptors. In some embodiments, the analyte is HER2, a portion of HER2, or a multimeric protein complex that includes HER2. In some embodiments, the detected HER2 is obtained from serum.

In some embodiments, the analyte is a viral or bacterial protein, DNA, or RNA. Stated differently, in some embodiments, the analyte is DNA, RNA, or a protein from a virus or a bacterium, such as a pathogenic virus or bacterium. Exemplary viruses and bacteria for the analyte can be selected from any of the following: astrovirus, chickenpox, dengue virus, Ebola, foot-and-mouth disease virus, hepatitis A, hepatitis B, hepatitis C, herpes, human immunodeficiency virus, human papillomavirus, influenza, Japanese encephalitis, measles, mumps, Naples virus, parvovirus, rabies, rubella, shingles, smallpox, Toscana virus, Varicella Zoster virus, West Nile virus, yellow fever, Zika virus, *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica*, and *Yersinia pseudotuberculosis*.

In some embodiments, the analyte is a complex formed from protein interaction partners. Any suitable set of protein interaction partners may be used as an analyte. In some embodiments, an analyte may be a cell surface or membrane-bound complex, such as the EGFR-HER2 complex, the HER2-HER2 homodimer, or the HER2-HER3 heterodimer. In other embodiments, the analyte is a soluble complex, such as the P53-MDM2 complex, VEGF dimer, BAk-BclxL complex, or the XIAP-Smac complex.

As noted above, in some embodiments, the analyte is a modified protein. The modification to the protein may be any suitable modification (e.g., a post-translation modification). In some embodiments, the modification is a naturally occurring modification. In some embodiments, the modification is indicative of a normal state or a disease state. In some embodiments, the modification is a synthetic modification, such as a protein that has been modified to improve pharmacokinetics, improve efficacy, and/or to reduce toxicity. Exemplary post-translational modifications include phosphorylation, glycosylation, lipidation, or acylation. In some embodiments, the modified protein is a pegylated protein, such as, for example, pegadamase, pegaspargase, peginterferon-2b, peginterferon-2a, pegfilgrastim, pegvisomant, pegaptanib, mPEG-epoetin, certolizumab, PEG-uricase. In some embodiments, the protein is modified after removal from a cellular environment. Such modification can improve pharmacokinetics, enhance efficacy, and/or decrease toxicity of the modified protein. In some embodiments, the analyte is an antibody-drug conjugate. In some embodiments, the analyte is an antibody-enzyme conjugate. In some embodiments, the analyte is a fusion protein.

In some embodiments, the analyte is an autoantibody. In such embodiments, the analyte may be an autoantibody that recognizes and binds a self-antigen. In some embodiments, the analyte is selected from any of the following: antinuclear antibodies including anti-SSA/Ro autoantibodies, anti-La/SS-B autoantibodies, anti-centromere antibodies, anti-double-stranded DNA (dsDNA) antibodies, anti-Jo1 antibodies or anti-histidine-tRNA ligase antibodies, anti-ribonucleoprotein (RNP) antibodies, anti-snRNP core proteins antibodies or anti-Smith antibodies, anti-topoisomerase antibodies, anti-histone antibodies, anti-nucleoporin 62 antibodies or anti-p62 antibodies, anti-sp 100 or anti-sp 100 nuclear antigen antibodies, anti-nucleoporin 210 kDA antibodies or anti-glycoporin-210 antibodies, anti-transglutaminase antibodies including anti-tTG antibodies and anti-eTG antibodies, anti-ganglioside antibodies including anti-ganglioside GQ1B antibodies, anti-ganglioside GD3 antibodies, and anti-ganglioside GM1 antibodies, anti-actin antibodies, anti-cyclic citrulllinated peptide antibodies, anti-liver kidney microsomal type 1 antibodies, anti-lupus anticoagulant antibodies, anti-thrombin antibodies, anti-phospholipid antibodies, anti-neutrophil antibodies including anti-c-ANCA antibodies and anti-p-ANCA antibodies, anti-rheumatoid factor antibodies, anti-smooth muscle antibodies, anti-mitochondrial antibodies, anti-signal recognition particle (SRP) antibodies, anti-nicotinic acetylcholine receptor (AChR) antibodies, anti-muscle-specific kinase (MUSK) antibodies, anti-voltage-gated calcium channel (VGCC) antibodies including anti-P/Q-type voltage-gated calcium channel antibodies, anti-thyroid antibodies including anti-thyroid peroxidase (TPO) antibodies, anti-thyroglobulin antibodies (TgAbs), and anti-thyrotropin receptor antibodies (TRAbs), anti-Hu (ANNA-1) antibodies, anti-Yo antibodies, anti-Ma antibodies, anti-Ri (ANNA-2) antibodies, anti-Tr antibodies, anti-amphiphysin antibodies, anti-glutamate decarboxylase (GAD) antibodies, anti-voltage-gated potassium channel (VGKC) antibodies, anti-collapsin response mediator protein 5 (CRMP-5) antibodies, anti-N-methyl-D-aspartate receptor (NMDAr) antibodies, and anti-aquaporin or anti-NMO antibodies. In some embodiments, the autoantibody binds to an acetylcholine receptor (e.g., a nicotinic acetylcholine receptor).

In some embodiments, when a particular autoantibody is known to interact with a particular self-antigen target to cause an autoimmune disease or disorder, the disclosed methods may be used to diagnose or confirm that a patient has, or is at risk of developing, a particular form of autoimmune disease or autoimmune-associated disease.

For example, when a patient is suspected of having systemic lupus erythematosus (SLE), the underlying cause of that SLE may be confirmed and/or attributed to the presence of anti-SSA/Ro autoantibodies, anti-double-stranded DNA (dsDNA) antibodies, anti-histone antibodies, anti-snRNP core proteins antibodies or anti-Smith antibodies and/or anti-lupus anticoagulant antibodies or anti-thrombin autoantibodies by the methods described herein.

When a patient is suspected of having neonatal heart block, the underlying cause may be confirmed and/or attributed to the presence of anti-SSA/Ro autoantibodies by the methods described herein.

When a patient is suspected of having primary Sjögren's syndrome the underlying cause of the syndrome may be confirmed and/or attributed to the presence of anti-SSA/Ro autoantibodies or anti-La/SS-B autoantibodies by the methods described herein.

When a patient is suspected of having CREST syndrome the underlying cause of the syndrome may be confirmed and/or attributed to the presence of anti-centromere antibodies by the methods described herein.

When a patient is suspected of having inflammatory myopathy, the underlying cause may be confirmed and/or attributed to the presence of anti-Jo1 antibodies or anti-histidine-tRNA ligase autoantibodies by the methods described herein.

When a patient is suspected of having mixed connective tissue disease, the underlying cause may be confirmed and/or attributed to the presence of anti-ribonucleoprotein or anti-RNP autoantibodies by the methods described herein.

When a patient is suspected of having systemic sclerosis, the underlying cause of the disease may be confirmed and/or attributed to the presence of anti-Scl-70 antibodies or anti-type I topoisomerase antibodies by the methods described herein.

When a patient is suspected of having primary biliary cirrhosis, the underlying cause of the disease may be confirmed and/or attributed to the presence of anti-nucleoporin 62 antibodies or anti-p62 antibodies, anti-sp100 or anti-sp100 nuclear antigen antibodies, anti-nucleoporin 210 kDA antibodies or anti-glycoporin-210 antibodies by the methods described herein.

When a patient is suspected of having celiac disease, the underlying cause of the disease may be confirmed and/or attributed to the presence of anti-transglutaminase (tTG) antibodies by the methods described herein.

When a patient is suspected of having dermatitis herpetiformis, the underlying cause of the disease may be confirmed and/or attributed to the presence of anti-transglutaminase (eTG) antibodies by the methods described herein.

When a patient is suspected of having Miller-Fisher syndrome the underlying cause of the syndrome may be confirmed and/or attributed to the presence of anti-ganglioside GQ1B antibodies by the methods described herein.

When a patient is suspected of having acute motor axonal neuropathy (AMAN) the underlying cause of the disease may be confirmed and/or attributed to the presence of anti-ganglioside GD3 antibodies by the methods described herein.

When a patient is suspected of having multifocal motor neuropathy with conduction block (MMN) the underlying cause of the disease may be confirmed and/or attributed to the presence of anti-ganglioside GM1 antibodies by the methods described herein.

When a patient is suspected of having rheumatoid arthritis the underlying cause of the disease may be confirmed and/or attributed to the presence of anti-cyclic citrullinated peptide (CCP), or anti-rheumatoid factor antibodies by the methods described herein.

When a patient is suspected of having autoimmune hepatitis, or chronic autoimmune hepatitis, the underlying cause of the disease may be confirmed and/or attributed to the presence of anti-liver kidney microsomal type 1 antibodies or anti-smooth muscle antibodies by the methods described herein.

When a patient is suspected of having antiphospholipid syndrome the underlying cause of the syndrome may be confirmed and/or attributed to the presence of anti-phospholipid antibodies by the methods described herein.

When a patient is suspected of having granulomatosis with polyangiitis the underlying cause of the disease may be confirmed and/or attributed to the presence of anti-neutrophil cytoplasmic (c-ANCA) antibodies by the methods described herein.

When a patient is suspected of having microscopic polyangiitis, eosinophilic granulaomatosis with polyangiitis, or systemic vasculitides, the underlying cause of the disease may be confirmed and/or attributed to the presence of anti-neutrophil perinuclear (p-ANCA) antibodies by the methods described herein.

When a patient is suspected of having primary biliary cirrhosis the underlying cause may be confirmed and/or attributed to the presence of anti-mitochondrial antibodies by the methods described herein.

When a patient is suspected of having polymyositis the underlying cause may be confirmed and/or attributed to the presence of anti-signal recognition particle (SRP) antibodies by the methods described herein.

When a patient is suspected of having scleromyositis the underlying cause may be confirmed and/or attributed to the presence of anti-exosome complex antibodies by the methods described herein.

When a patient is suspected of having myasthenia gravis the underlying cause may be confirmed and/or attributed to the presence of anti-acetylcholine receptor (anti-AChr), or anti-muscle-specific kinase (MUSK) antibodies by the methods described herein.

When a patient is suspected of having Lambert-Eaton myasthenic syndrome the underlying cause of the syndrome may be confirmed and/or attributed to the presence of anti-voltage-gated calcium channel (P/Q-type) (VGCC) antibodies by the methods described herein.

When a patient is suspected of having Hashimoro's thyroiditis or Graves' disease the underlying cause may be confirmed and/or attributed to the presence of anti-thyroid peroxidase (TPO) antibodies, anti-thyroglobulin antibodies (TgAbs), or anti-thyrotropin receptor antibodies (TRAbs) by the methods described herein.

When a patient is suspected of having paraneoplastic cerebellar degeneration, limbic encephalitis, encephalomyelitis, subacute sensory neuronopathy, or choreathetosis, the underlying cause of the disease may be confirmed and/or attributed to the presence of anti-Hu (ANNA-1) autoantibodies, anti-Yo autoantibodies, or anti-amphiphysin antibodies by the methods described herein.

When a patient is suspected of having opsoclonus myoclonus syndrome the underlying cause of the syndrome may be confirmed and/or attributed to the presence of anti-Ri (ANNA-2) antibodies by the methods described herein.

When a patient is suspected of having paraneoplastic cerebellar syndrome the underlying cause of the syndrome may be confirmed and/or attributed to the presence of anti-Tr or anti-glutamate receptor autoantibodies by the methods described herein.

When a patient is suspected of having stiff person syndrome the underlying cause of the syndrome may be confirmed and/or attributed to the presence of anti-amphiphysin or anti-glutamate decarboxylase (anti-GAD) autoantibodies by the methods described herein.

When a patient is suspected of having Isaac's syndrome (autoimmune neuromyotonia) or limbic encephalitis the underlying cause may be confirmed and/or attributed to the presence of anti-voltage-gated potassium channel (anti-VGKC) autoantibodies by the methods described herein.

When a patient is suspected of having optic neuropathy or chorea the underlying cause may be confirmed and/or attributed to the presence of anti-collapsin response mediator protein 5 (anti-CRMP-5) autoantibodies by the methods described herein.

When a patient is suspected of having Sydenham's chorea or pediatric autoimmune neuropsychiatric disease associated with *Streptococcus* (PANDAS), the underlying cause may be confirmed and/or attributed to the presence of anti-basal ganglial neuron autoantibodies by the methods described herein.

When a patient is suspected of having anti-N-methyl-D-aspartate (NDMA) receptor encephalitis the underlying cause may be confirmed and/or attributed to the presence of anti-NDMAr autoantibodies by the methods described herein.

When a patient is suspected of having neuromyelitis optica (Devic's syndrome) the underlying cause may be confirmed and/or attributed to the presence of anti-aquaporin-4 autoantibodies or NMO antibodies by the methods described herein.

The specific examples described above to confirm the underlying cause of a given autoimmune disease or autoimmune-related disease are only exemplary. Indeed, the disclosed methods may be used to diagnose a wide range of known autoimmune or autoimmune-related diseases, including: Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticarial, Axonal & neuronal neuropathies, Balo disease, Behcet's disease, Bullous pemphigoid, Cardiomyopathy, Castleman disease, Celiac disease, Chagas disease, Chronic fatigue syndrome-associated autoimmune diseases, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia-associated autoimmune diseases, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease (chronic), Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA)).

In some embodiments, the affinity of the first and/or second targeting domains to the corresponding target regions may be greater than the affinity of the peptide fragments of the split protein to the remaining peptide fragment(s) of the split protein, thereby reducing background signal. In some embodiments the affinity of the first and/or second targeting domains to the corresponding target regions may be at least 1, 2, 3, and/or 4 orders of magnitude greater than the affinity of a peptide fragment of the split protein to the remaining peptide fragment(s) of the split protein complex. In some embodiments, the first targeting domain and the second targeting domain do not bind directly to each other. In other words, the first targeting domain and the second targeting domain may be brought near each other not through any direct interaction between the first targeting domain and the second targeting domain but through binding to the same analyte.

Related kits may be used to detect an analyte. In some embodiments, the kit includes a first vector. The first vector may include a first sequence that encodes a first peptide fragment of a tripartite split enzyme. The vector may be configured to facilitate insertion of a nucleotide sequence for a first targeting domain such that expression of the resulting vector yields a fusion protein that includes both the first targeting domain and the first peptide fragment.

In some embodiments, the kit may additionally or alternatively include a second vector. The second vector may include a second sequence that encodes a second peptide fragment of a tripartite split enzyme. The vector may be configured to facilitate insertion of a nucleotide sequence for a second targeting domain such that expression of the resulting vector yields a fusion protein that includes both the second targeting domain and the second peptide fragment.

In some embodiments, the kit may include a third fragment of the tripartite split enzyme. The third peptide fragment may have a mass of between 16 kDa and 17 kDa. In some embodiments, the third peptide fragment has at least 70%, 80%, 90%, 95%, or 100% sequence identity to the sequence of SEQ ID NO 3. In some embodiments, the third peptide fragment is between 140 and 150 amino acids. For example, in some embodiments, the third peptide is between 145 and 150 amino acids (e.g., 148 amino acids). In some embodiments, the kit may additionally or alternatively include a vector for expressing the third fragment of the tripartite split enzyme.

In other embodiments, a kit may include a first agent, a second agent, and a third agent, as defined above. The first agent may include a first targeting domain and a first peptide fragment of a split reporter protein. The second agent may include a second targeting domain and a second peptide fragment of the split reporter protein. The third agent may include a third fragment of the split reporter protein. In some such embodiments, the first and second targeting domains determine the antigen to be detected using the kit. Such a kit may optionally include the reagents necessary to generate a detectable signal when the first, second and third fragments of the split reporter protein are assembled into a functional reporter protein, such as a functional enzyme reporter. In such embodiments, the kit may optionally include the substrate for the assembled functional enzyme reporter, and instructions for use of the kit for detecting a specific antigen. In some embodiments of such kits, the specific analyte to be detected may be selected from any of the analytes disclosed herein. In some embodiments of such kits, the specific analyte to be detected may be selected from an antibody formed in response to an allergen, a bacterial infection, or a viral infection, a therapeutic antibody, or and autoantibody that binds a self-antigen.

Some embodiments within the scope of this disclosure may be detection reagents. Some detection reagents may include a targeting domain and a peptide fragment of a tripartite split reporter protein. The peptide fragment of the detection reagent may have a mass of less than 3 kDa. In some embodiments, the peptide fragment is 15, 14, 13, 12, 11, or 10 amino acids in length. In some embodiments, the peptide fragment has at least 80%, 90%, 95%, and/or 100% sequence identity to the sequence of SEQ ID NO 1. In other embodiments, the peptide fragment has at least 80%, 90%, 95%, and/or 100% sequence identity to the sequence of SEQ ID NO 2. The peptide fragment of a detection reagent may be capable of forming a complex with one or more other peptide fragments to form an intact split reporter protein.

Some embodiments may be nucleic acids. For example, some nucleic acids may include a sequence that includes a promoter, an insertion site, and a region that encodes a peptide fragment of a split reporter enzyme. The nucleic acid may be configured such that insertion of a sequence that encodes a targeting domain at the insertion site allows for expression of a fusion protein that includes the targeting domain and the peptide fragment. Stated differently, the sequence of the resulting nucleotide, which encodes a fusion protein, may be operably linked to a promoter.

Some embodiments include methods for detecting an analyte in a mixture (e.g., a mixture in a vessel). The method may include the step of delivering a plurality of agents into a mixture, wherein each of the agents includes a portion of a split reporter protein. For example, some methods may include the steps of delivering a first agent into the mixture, and delivering a second agent into the mixture. The first agent may include a first targeting domain and a first peptide fragment of the split reporter protein. The second agent may include a second targeting domain and a second peptide fragment of the split reporter protein. In some embodiments, the split reporter protein is a binary split reporter protein (i.e., the split reporter protein has only two fragments). In other embodiments (e.g., where the split reporter protein is a ternary split reporter protein), the method may further include the step of delivering a third agent into the mixture. The third agent may include or consist essentially of a third fragment of the split reporter protein. In some embodiments, the first agent and the second agent are delivered in substantially equimolar amounts (e.g., a ratio of 1:1 (±0.2)). In some embodiments, the first agent and the second agent are not delivered in substantially equimolar amounts. In some embodiments, the first agent and the second agent are delivered as purified proteins.

Upon delivery into the mixture, the first targeting domain of the first agent may bind to a first target region of the analyte. Similarly, the targeting domain of the second agent may bind to a second target region of the analyte. Such binding may increase the local concentration of these components. In embodiments that involve a binary split reporter protein, the first agent and the second agent may bind to one another to form an active complex. In embodiments that involve a ternary split reporter protein, the first agent and the second agent may bind (e.g., non-covalently) to a third agent to form an active complex. In both cases, the active complex is formed essentially only where the first agent and the second agent are in close proximity. These methods, in which binding of the individual peptide fragments to form an active complex is driven by the binding of targeting domains to an analyte, may be termed "target-binding activated complementation" or "target-engaged complementation."

In some embodiments, the first agent and the second agent are delivered to the mixture prior to delivery of the third agent. In other embodiments, the first agent, the second agent, and the third agent are simultaneously delivered to the mixture. Numerous different ordering of steps is possible, as will be understood by a skilled artisan having the benefit of this disclosure.

In some embodiments, the method further includes the step of delivering a substrate of the active complex into the mixture. Some methods may include the step of detecting light emitted from the mixture after the first agent, the second agent, and the third agent have been delivered to the mixture. The amount of light emitted from the mixture may be proportional to the amount of analyte that is contained therein. In some embodiments, the method is capable of detecting the analyte at concentrations of less than 5 pM, such as concentrations of less than 1 pM.

In some embodiments, the method is practiced outside of living cells. Stated differently, in some embodiments, the analyte to be detected is not disposed within a cell. In some embodiments, the analyte is detected in or from a cell lysate. In some embodiments, the method is carried out in a biological fluid. For example, some methods may be carried out in human serum or in a mixture that includes human serum. Other methods may be carried out in saliva or in a mixture that includes saliva. Other methods may be carried out in urine or in a mixture that includes urine. Detection of one or more analytes from other biological fluids is also contemplated.

In some embodiments, the method for detecting the analyte does not include a blocking step. Stated differently, in some embodiments, the method does not require delivery of a blocking agent, such as bovine serum albumin or milk proteins.

In some embodiments, the method for detecting the analyte does not include a wash step. Stated differently, in some embodiments, an unbound first agent and second agent need not be removed from the mixture prior to detection.

In some embodiments, the method for detecting the analyte does not involve immobilization of the analyte. In other words, in some embodiments, the analyte may be in solution (e.g., a homogeneous solution) when detected. In other embodiments, the analyte is immobilized onto a surface. In other embodiments, the analyte is present on the surface of a tissue or tissue sample (e.g., a prepared tissue sample mounted on a microscope slide).

In some embodiments, the method does not require the use of protein disulfide isomerase. Stated differently, in some methods, none of the first peptide fragment, the second peptide fragment, or the third peptide fragment contacts a protein disulfide isomerase.

FIG. 1 shows an embodiment of a split reporter system 100. The split reporter system 100 includes a first agent 110 and a second agent 120. The first agent 110 includes a first targeting domain 112 and a first peptide fragment 114 of a split reporter protein 101. The second agent 120 includes a second targeting domain 122 and a second peptide fragment 124 of the split reporter protein 101. Each targeting domain 112, 122 has an affinity to a particular target region 51, 52 of an analyte 50. In the depicted embodiment, the targeting domains are Fabs and the analyte 50 is a corresponding bivalent antigen.

When the first agent 110 and the second agent 120 are mixed with the antigen 50, the first targeting domain 112 of the first agent binds to a first epitope 51 of the antigen 50 and the second targeting domain 122 of the second agent 120 binds to the second epitope 52 of the antigen 50, thereby bringing the first peptide fragment 114 and the second peptide fragment 124 into close proximity. The close proximity of the first peptide fragment 114 to the second peptide fragment 124 leads to formation of an active reporter protein complex (i.e., intact split reporter protein 101). The active reporter protein complex can produce a detectable signal (e.g., fluorescence of luminescence). Thus, the signal produced by the active reporter protein complex may be used to detect the presence (and/or determine the quantity) of analyte 50 in a mixture.

Figure 2:
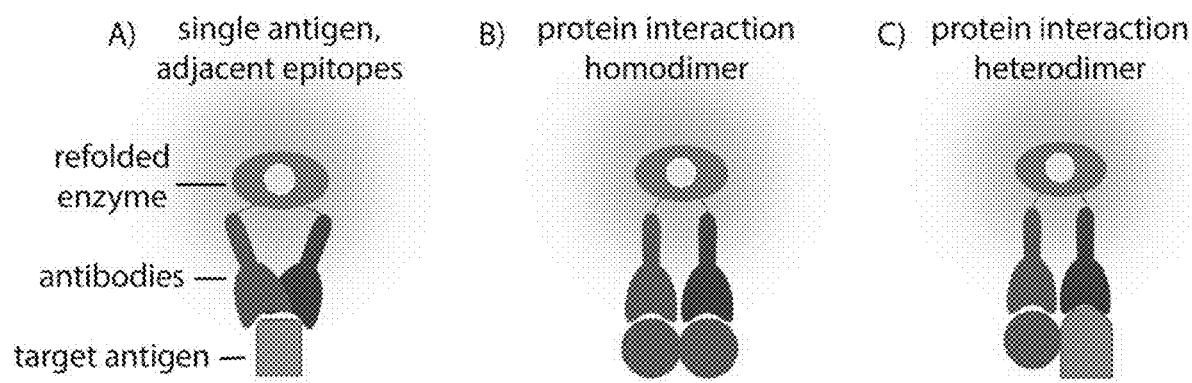
FIG. 2 is a schematic that shows alternative targeting modes for activating complementation in a split reporter system.

FIG. 2 is a schematic showing various targeting modes (FIGS. 2A-2C) for activating fragment complementation in a split reporter system. For example, FIG. 2A shows binding of targeting domains (e.g., antibodies) to adjacent target regions (e.g., epitopes) on a single bivalent analyte (e.g., antigen). FIG. 2B shows binding of targeting domains to identical target regions on separate proteins of a homomultimeric protein complex. And FIG. 2C shows binding of targeting domains to different proteins of a heteromultimeric protein complex. Any of the targeting modes shown in FIG. 2 may be used to detect an analyte.

Figure 3:
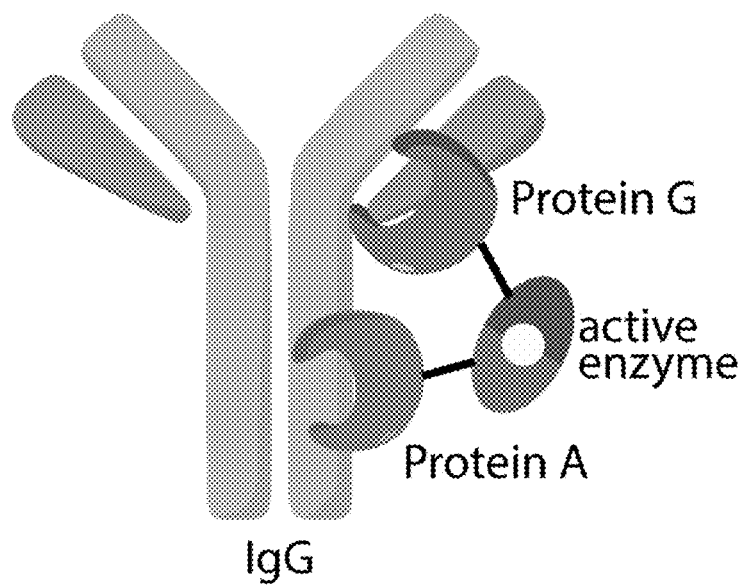
FIG. 3 is a schematic showing binding of fragment complementation components to an immunoglobulin antibody.

FIG. 3 is a schematic showing a fragment complementation system for detecting an antibody (e.g., IgG). In the depicted embodiment, a first agent includes (1) a first peptide fragment of a split reporter protein and (2) a first targeting domain (e.g., protein A) with affinity to a first target region of the antibody. The second agent includes (1) a second peptide fragment of a split reporter protein and (2) a second targeting domain (e.g., protein G) with affinity to a second target region of the antibody. When the first agent and the second agent are placed in a mixture that includes the antibody, the first agent and the second agent are drawn into proximity, which leads to formation of the split reporter protein complex.

Figure 4:
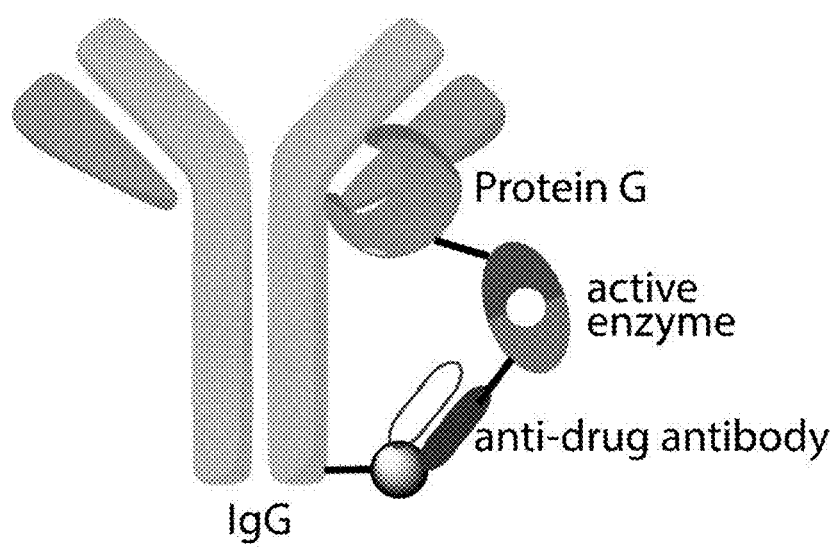
FIG. 4 is a schematic showing binding of fragment complementation components to a modified protein.

FIG. 4 is a schematic showing a fragment complementation system for detecting an antibody-drug conjugate. Such conjugates may be used, for example, to direct a drug to a particular location within a patient's body. In the depicted embodiment, the first agent includes a targeting domain with affinity to a drug that is attached to the antibody (e.g., via a linker), and the second agent includes a targeting domain (e.g., protein G) with affinity to a target region of the antibody. Such a fragment complementation system can be used to detect or quantify an antibody-drug conjugate in a mixture.

While the embodiments shown in FIGS. 1-4 are shown as two-component fragment complementation systems, a skilled artisan with the benefit of this disclosure will understand that analogous three-component fragment complementation systems are also within the scope of this disclosure.

Figure 5:
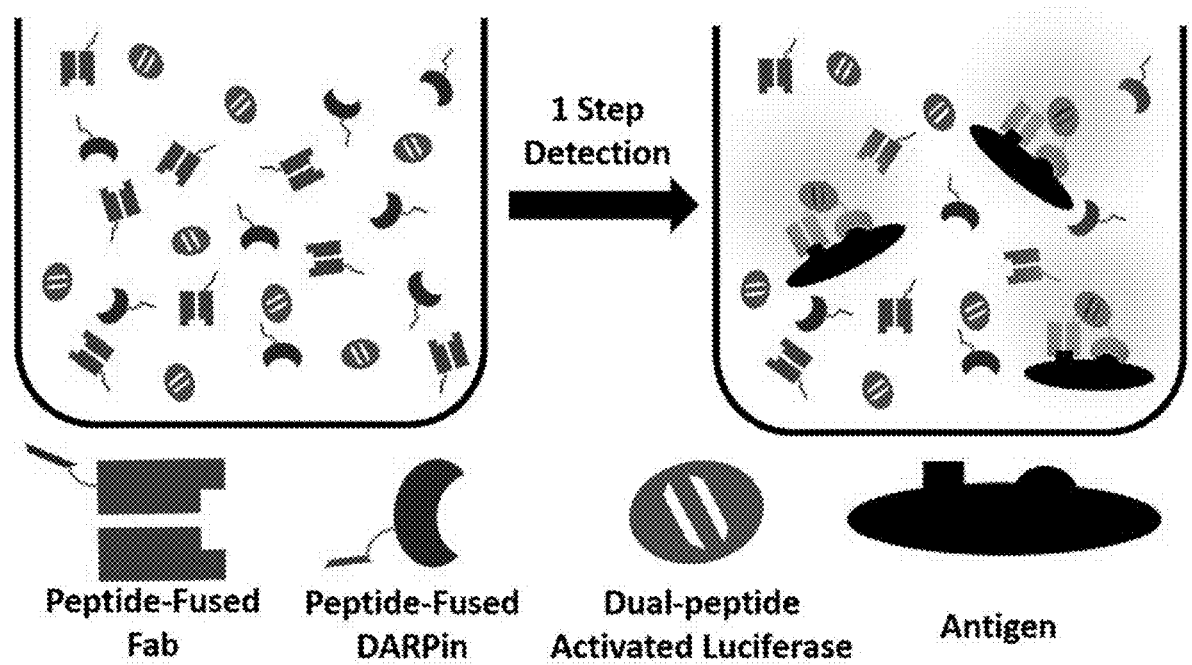
FIG. 5 is a schematic representation of a tripartite split reporter assay for detecting an analyte in a mixture.

FIG. 5 is a schematic showing detection of a single antigen via a tripartite fragment complementation system. More particularly, FIG. 5 shows a first agent that includes a first targeting domain (e.g., a Fab) and a first peptide fragment of a split reporter protein. The second agent includes a second targeting domain (e.g., a DARPin) and a second peptide fragment of a split reporter system. The embodiment shown in FIG. 5 also includes a third peptide fragment (i.e., a dual-peptide activated luciferase) of a split reporter system. When mixed in the presence of a bivalent antigen, the first agent and the second agent bind to different epitopes on the same bivalent antigen through their respective targeting domains. The first peptide fragment and the second peptide fragment may bind to the third peptide fragment to form an active split reporter protein complex (e.g., an active luciferase). In embodiments where the affinity of the first targeting domain and the second targeting domain to the antigen is significantly higher than the affinity of the components of the tripartite complex to each other, a signal generated from the activated complex (e.g., luminescence) may indicate the presence (or quantity) of antigen in a mixture. In some embodiments, one-step detection is possible. For example, an antigen may be added to a mixture that includes the three components of the tripartite fragment complementation system. The increase in signal from the activated complex may be used to detect and/or quantify the analyte.

Figure 6:
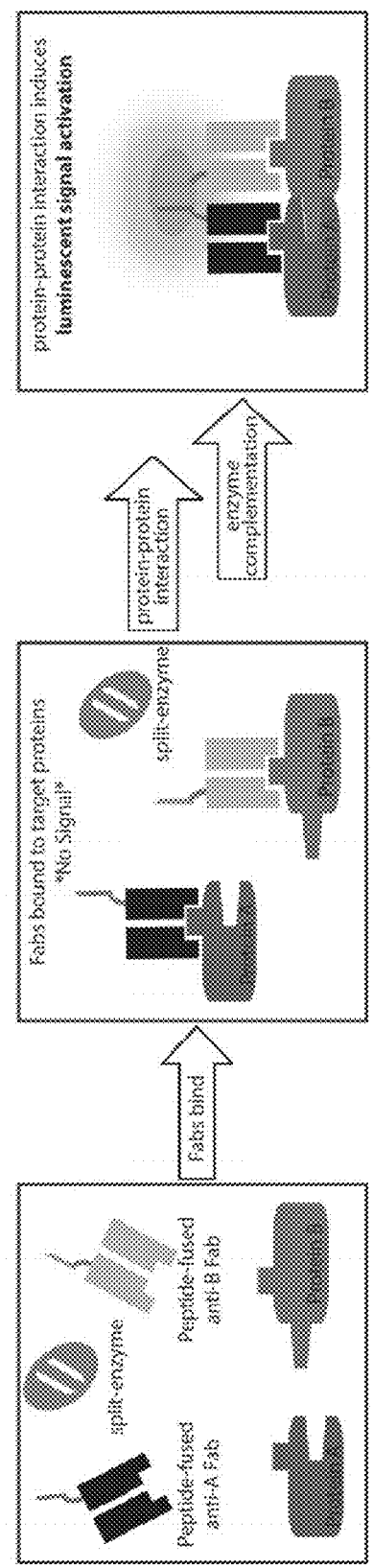
FIG. 6 is a schematic representation of a tripartite split reporter assay for detecting a molecular interaction.

FIG. 6 is a schematic that shows one embodiment for using a tripartite fragment complementation system to detect a protein-protein interaction. As shown in FIG. 6, the components of the fragment complementation system can be mixed with a pair of protein interaction partners. One agent of the fragment complementation system may bind to the first protein while a second agent of the fragment complementation system binds to a second protein. Upon (1) binding of the first protein to the second protein and (2) complementation with a third component of the fragment complementation system, an activated complex is formed, thereby allowing for detection of the interaction between the two proteins. In some embodiments, analogous detection can be accomplished where two proteins do not directly interact, but are in close proximity to one another.

Figure 7A:
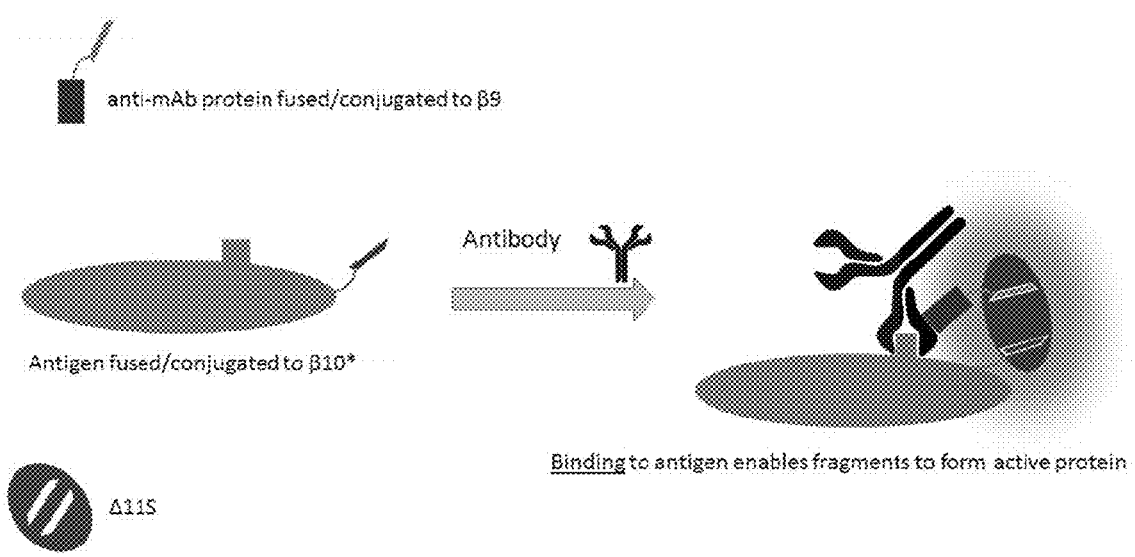
FIG. 7A is a schematic representation of a tripartite split reporter assay for detecting an antibody.
Figure 7B:
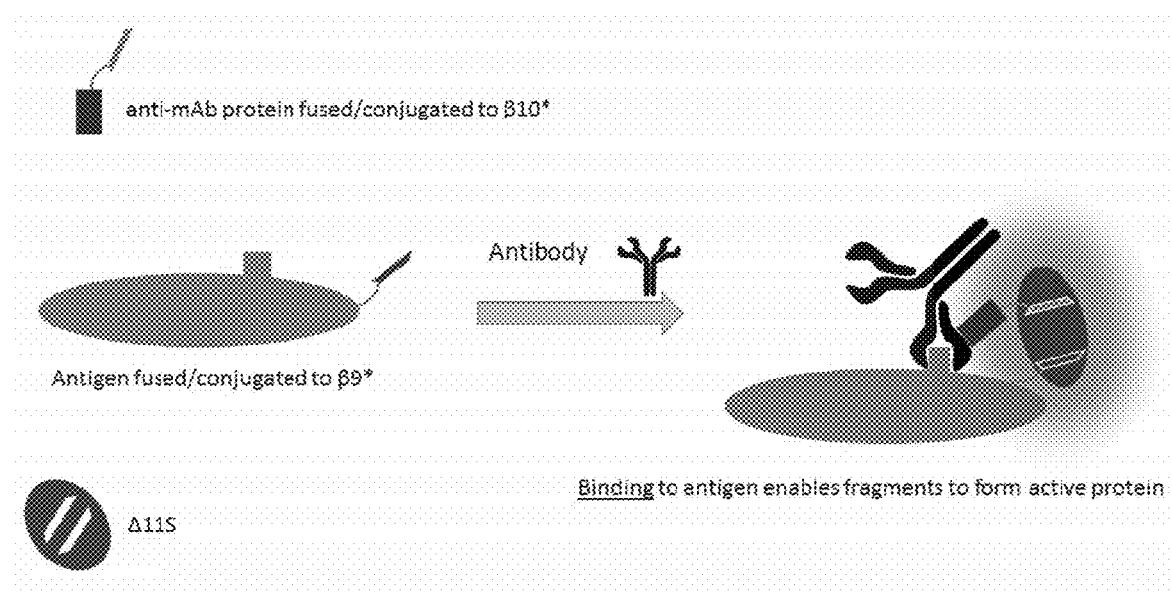
FIG. 7B is a schematic representation of a tripartite split reporter assay for detecting an antibody.

FIGS. 7A and 7B show alternative strategies for detection of an antibody (e.g., a therapeutic antibody or an autoantibody). In the schematics shown in FIGS. 7A and 7B, at least one component of the fragment complementation system is an agent that includes the corresponding antigen or epitope for the antibody. For example, in the depicted embodiments, a first agent includes a first peptide fragment and a first targeting domain that binds the antibody directly (e.g., an anti-mAb protein such as protein A, protein G, or protein L), while a second agent includes a second peptide fragment and a second targeting domain (e.g., the antigen or epitope to the targeted antibody). FIG. 7B differs from FIG. 7A in that, for FIG. 7A, the anti-mAb protein is fused or conjugated to β9 and the antigen is fused or conjugated to β10*. Conversely, in FIG. 7B, the anti-mAb protein is fused or conjugated to β10* while the antigen is fused or conjugated to β9. As shown in FIGS. 7A and 7B, binding of (1) the first targeting domain and the second targeting domain to the antibody and (2) the first peptide fragment and the second peptide fragment to a third fragment of the split reporter protein results in an active reporter protein complex, thereby allowing for detection of the antibody.

EXAMPLES

Recombinant Production of Split-Enzyme Reporter System Components

A tripartite split enzyme reporter system was engineered starting from NanoBiT®, a commercially available binary split enzyme reporter system for use in identifying protein-protein interactions. NanoBiT® includes an 11-amino acid peptide fragment (1.3 kDa) referred to as 114 and a 159-amino acid peptide fragment (18 kDa) referred to as 11S. The two fragments, when bound to one another, form a 10-stranded beta-barrel protein, with the 11S peptide fragment corresponding to the first nine beta stands of the protein, and 114 corresponding to the tenth beta strand.

Figure 8:
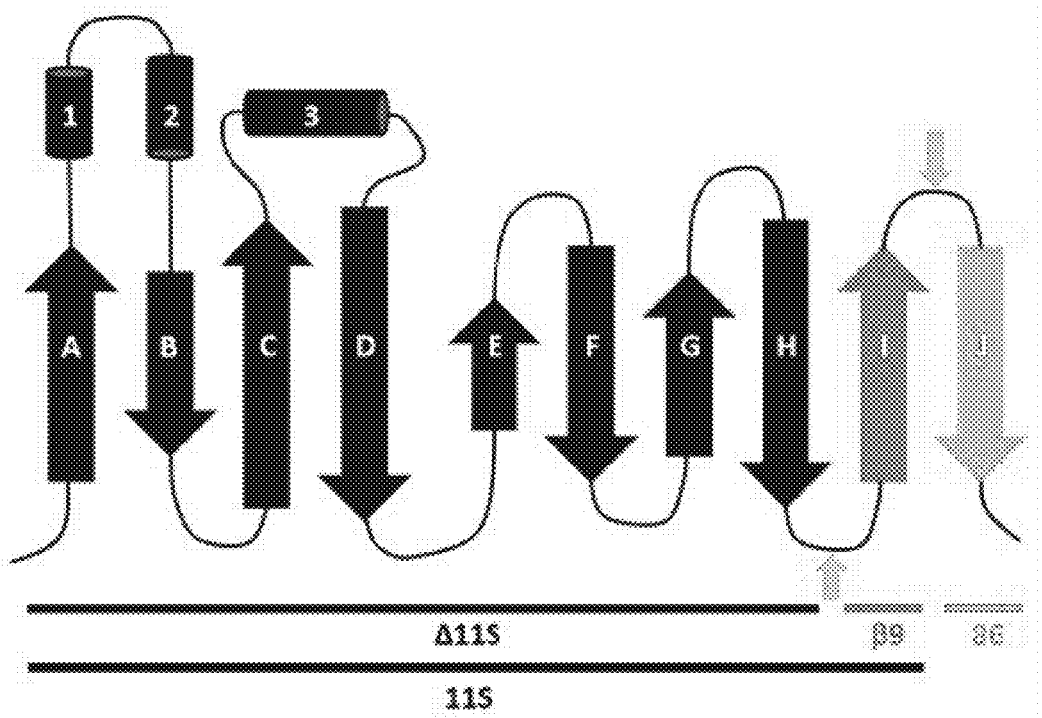
FIG. 8 is a topological representation of an engineered split luciferase. (β10* is sometimes referred to as "86" in the drawings.)

To develop the tripartite split enzyme, the 11S fragment was effectively split into two components: an 11-amino acid peptide (β9) corresponding to the most C-terminal amino acids of 11S, and a 148-amino acid peptide (Δ11S, 16.5 kDa) corresponding to the most N-terminal amino acids of 11S. Further, instead of using 114 (a relatively low affinity peptide, apparent $K_D$ of 190 μM) for the remaining β10 peptide fragment, a peptide "β10*" (VSGWRLFKKIS) with higher affinity (apparent $K_D$ of ~700 nM) for the remaining portions of the complex was used. In short, the tripartite enzyme reporter system included (1) a relatively large N-terminal fragment (Δ11S) that includes the first eight beta strands of the intact complex, (2) a relatively short peptide fragment (β9) that corresponds with the ninth beta strand, and (3) another relatively short peptide fragment (β10*) that corresponds with the tenth beta strand. Topological representations of the peptide fragments are depicted in FIG. 8. (β10* is sometimes referred to as 86 in the drawings.)

To generate the fragments of the tripartite split enzyme system, Δ11S was produced recombinantly, while β9 and β10* were synthesized by solid-phase peptide synthesis.

Enzymatic Activity and Kinetics of Split Enzyme System

Figure 9:
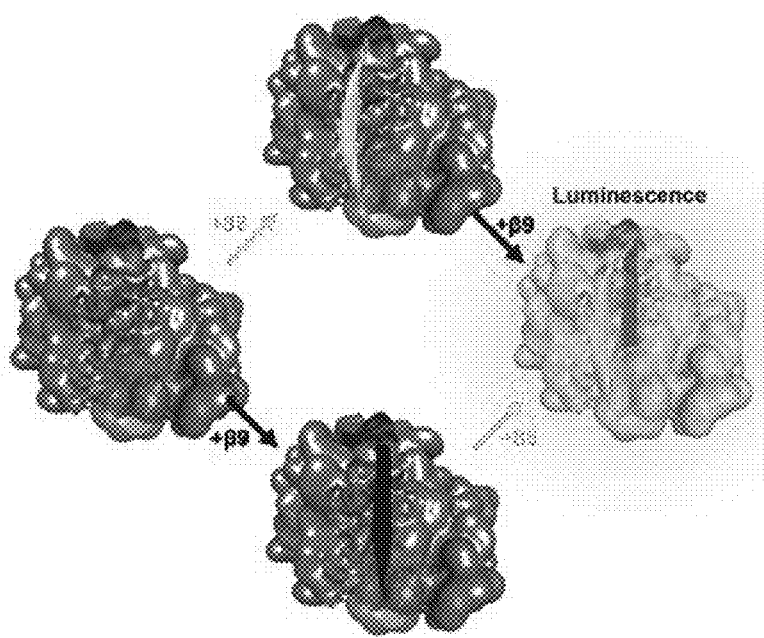
FIG. 9 is a structural model of different binding states for a tripartite split reporter protein.
Figure 10:
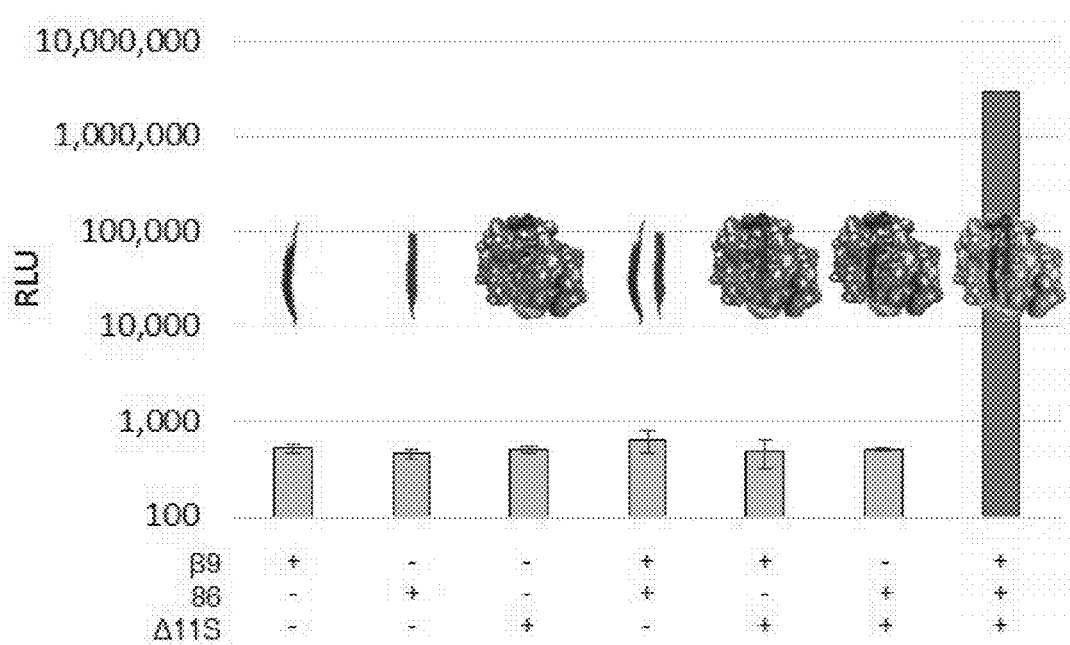
FIG. 10 is a bar graph showing luminescence of mixtures that have different components of a split reporter protein.

To confirm that the components of the reporter system were active only when all three peptide fragments were present as envisioned in the structural models shown in FIG. 9, the activity of various combinations of the peptide fragments (each at 1 μM concentration) was investigated in the presence of a substrate (furimazine). As shown in FIG. 10, the mixture of all three components is the only combination that produced significant luminescence. These findings confirmed that these fragments can be used to create a luminescent complementation system.

Figure 11:
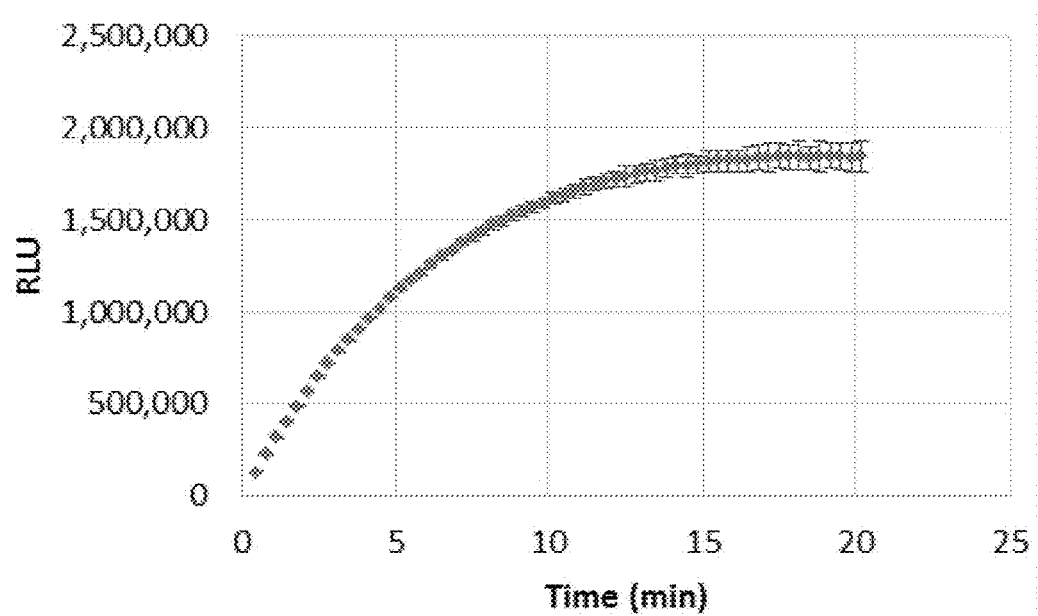
FIG. 11 is a scatterplot showing luminescence as a function of time for an analyte-detection assay.

Further, the luminescent signal was monitored after the addition of Δ11S (1 μM) into a solution that included both β9 and β10* (each at 1 μM). The results, as depicted in FIG. 11, show that, under the reaction conditions, 90% of the maximal signal was obtained within approximately 10 minutes, demonstrating that complex formation can be rapid.

Molecular Modeling and Screening to Identify Antibody Pairs for Target-Engaged Complementation in the Presence of HER2

Epidermal growth factor receptor 2 (HER2 or ErbB-2) was chosen for development and validation of a target-engaged complementation system. HER2 is a highly characterized biomarker (Kurebayashi, J., Breast Cancer 8, 45-51 (2001); Ross, J. S. et al. Mol Cell Proteomics 3, 379-98 (2004); Ross, J. S. et al., Oncologist 8, 307-25 (2003); Yu & Hung, Oncogene 19, 6115-21 (2000)) that has been the focus of significant research efforts stemming from its role in oncogenesis, including breast (Menard et al., J Cell Physiol 182, 150-62 (2000)), ovarian (Teplinsky & Muggia, Gynecol Oncol 135, 364-70 (2014); McAlpine et al., BMC Cancer 9, 433 (2009)), uterine (Santin et al., Clin Cancer Res 8, 1271-79 (2002); Todeschini et al., Br J Cancer 105, 1176-82 (2011)), gastric (Jorgensen, J. T., World J Gastroenterol 20, 4526-35 (2014); Hechtman & Polydorides, Arch Pathol Lab Med 136, 691-97 (2012)), and lung (Heinmoller et al., Clin Cancer Res 9, 5238-43 (2003)) cancers. HER2 expression levels can be used to diagnose and differentiate patients (Wesola & Jelen, Adv Clin Exp Med 24, 899-903 (2015)). Further, the extracellular domain of HER2 is often shed from cells, and its detection in serum can be used to monitor treatment and recurrence (Di Gioia et al., Clin Chim Acta 430, 86-91 (2014); Witzel et al., Breast Cancer Res Treat 123, 437-445 (2010); Esteva et al., Breast Cancer Res 7, R436-443 (2005)). Quantifying HER2 levels through targeted-engaged complementation can be simple and rapid, and may reduce the potential for error inherent to the multi-step protocols of typical immunoassays.

Figure 12:
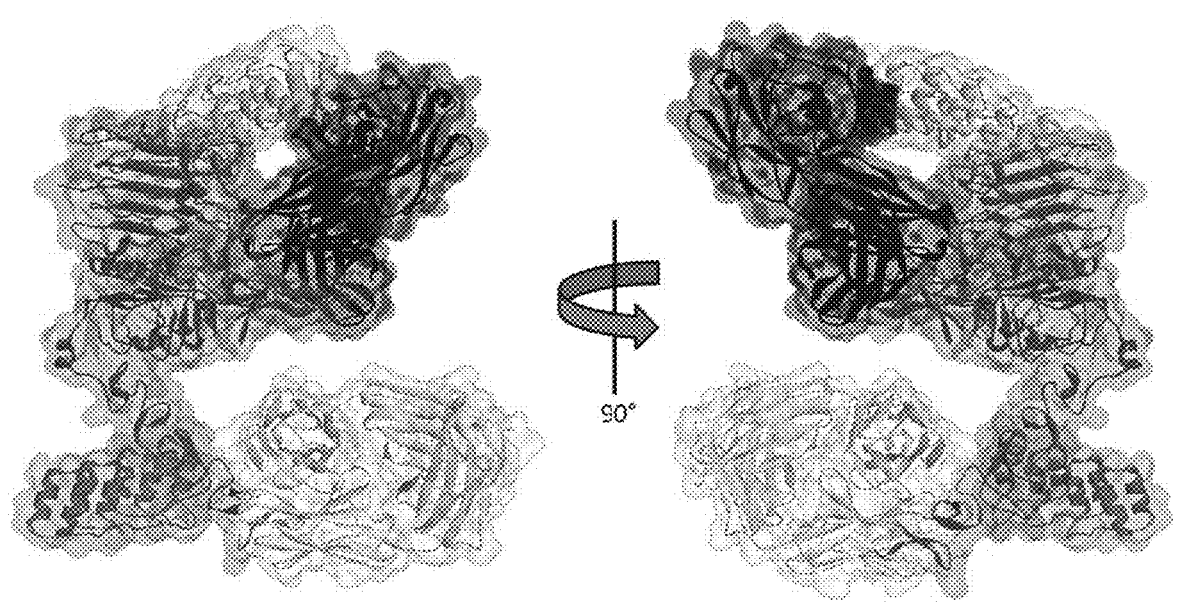
FIG. 12 is a molecular model of HER2 bound to various targeting domains.
Figure 13A:
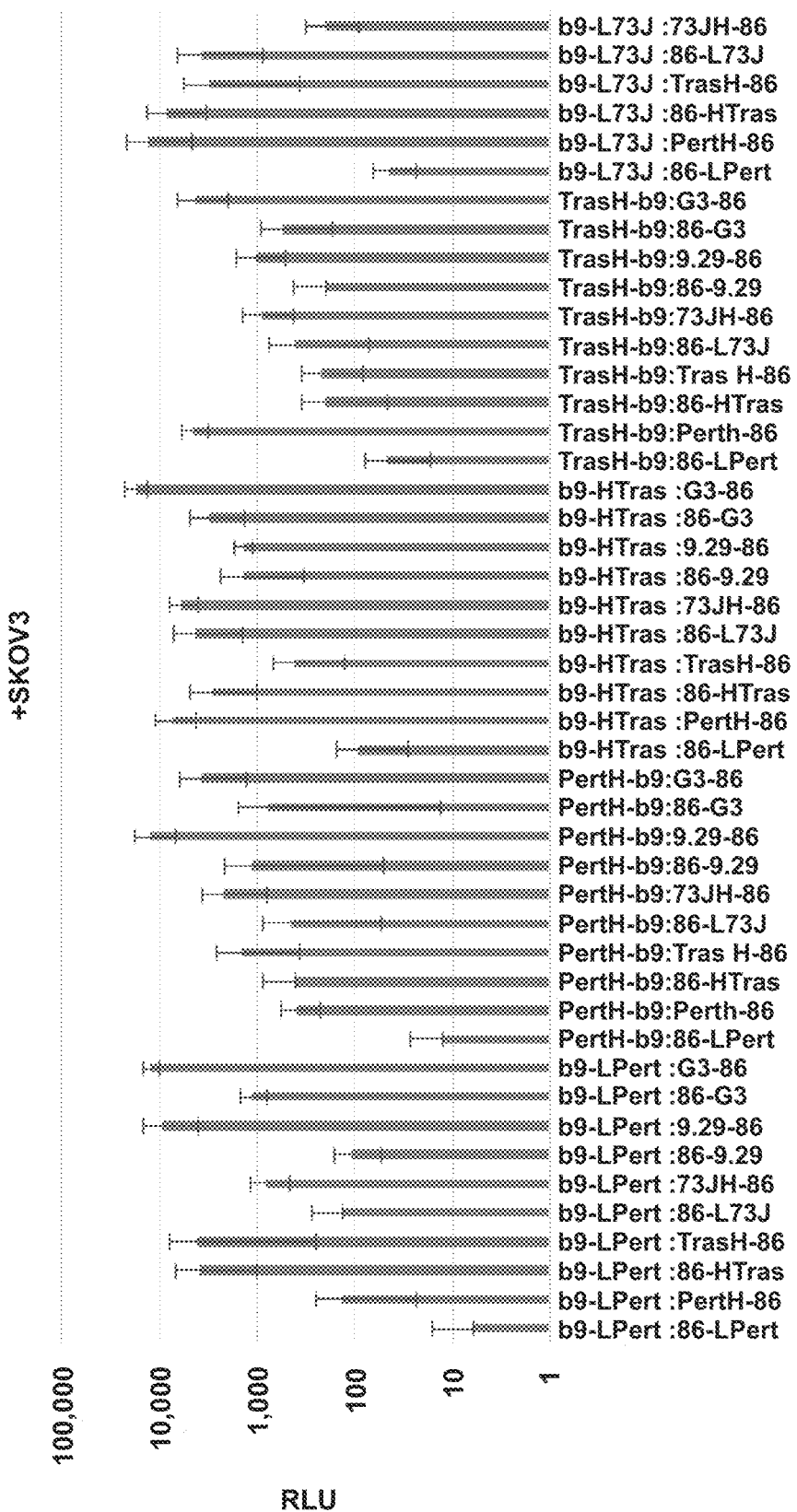
FIGS. 13A and 13B are a bar chart showing luminescence of various targeted split enzyme reporter systems in the presence of a target antigen.
Figure 13B:
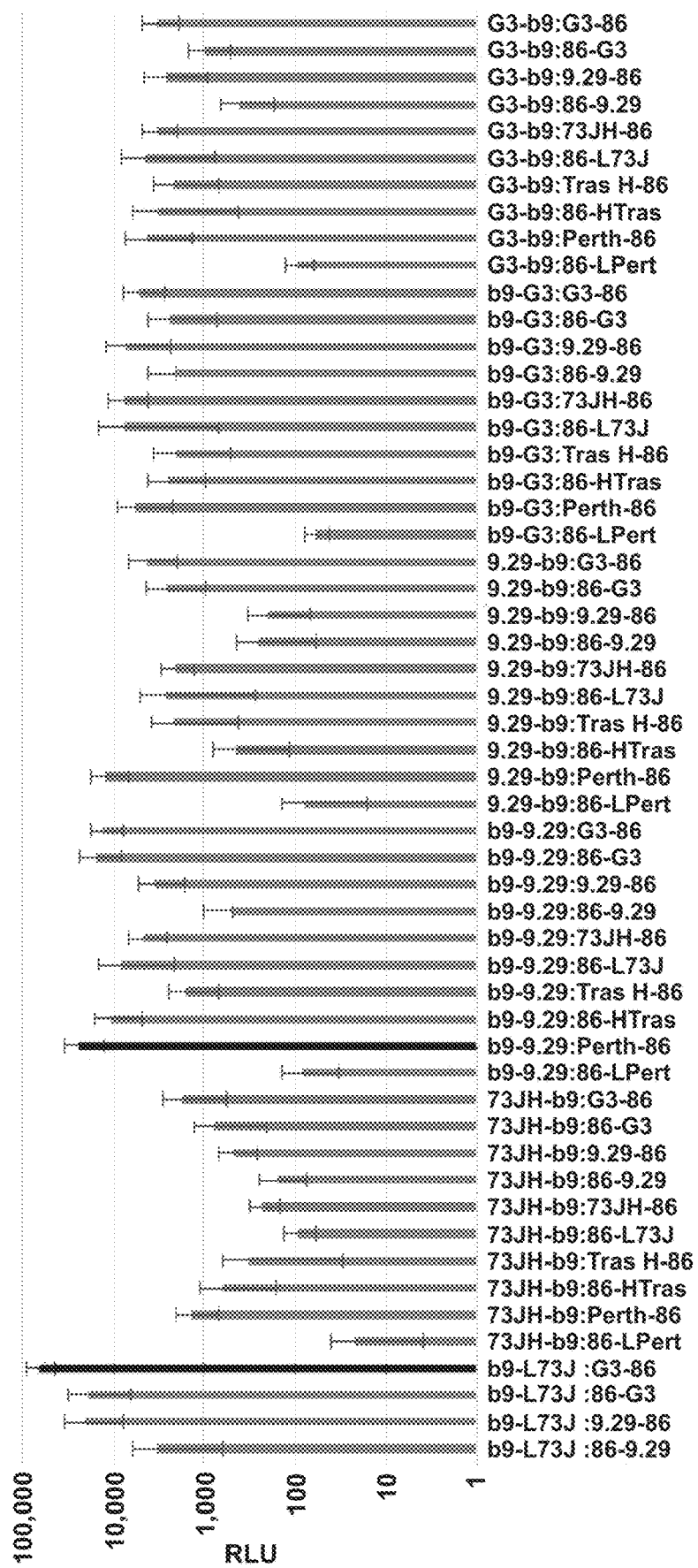
Figure 14A:
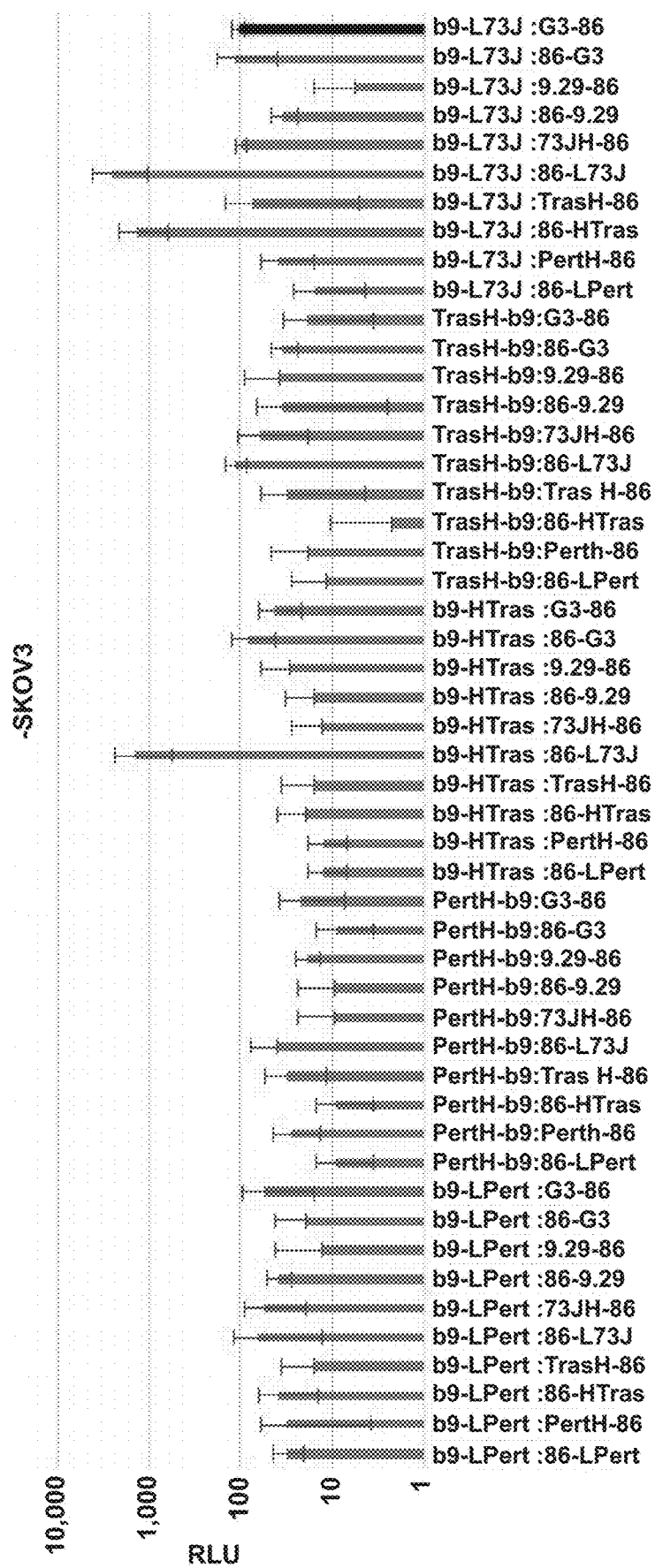
FIGS. 14A and 14B are a bar chart showing luminescence of various targeted split enzyme reporter systems in the absence of a target antigen.
Figure 14B:
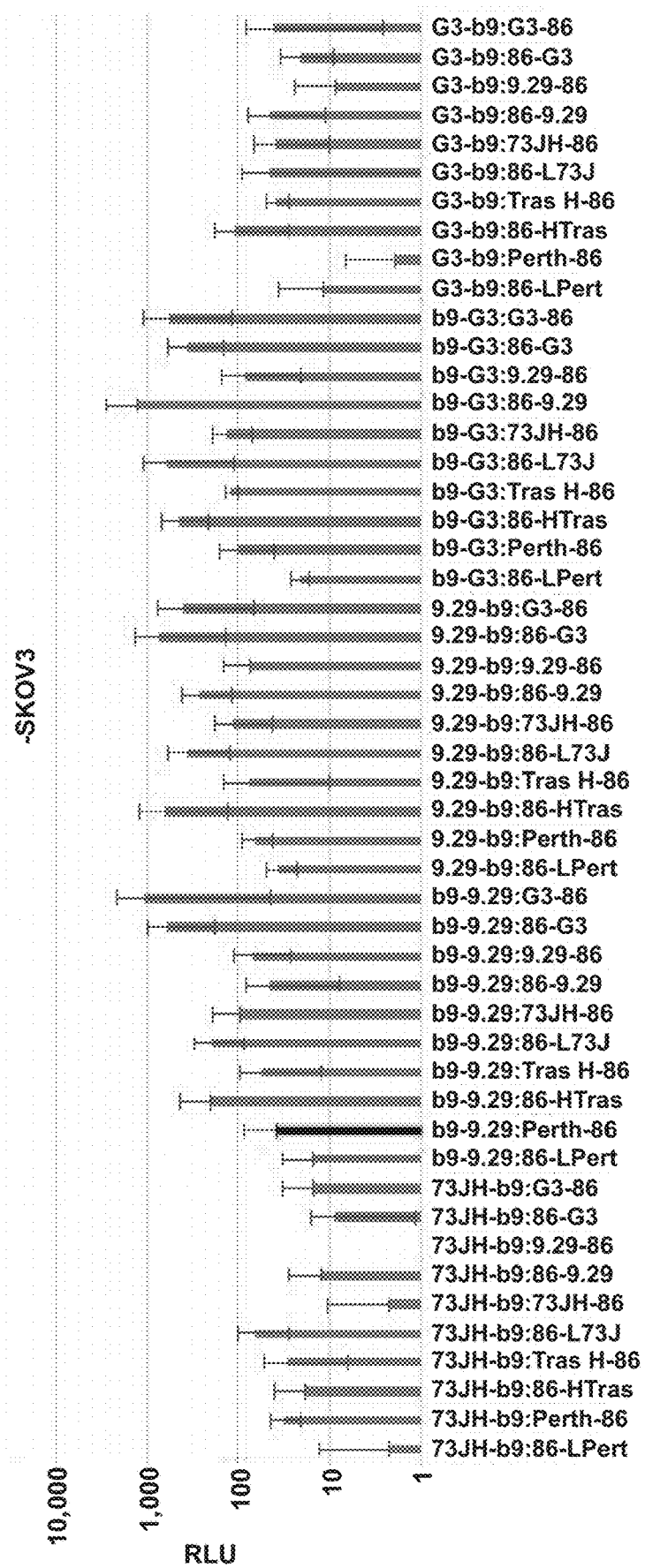

Molecular modeling was used to identify proximal, but non-overlapping epitopes on HER2. More specifically, crystal structures in the Protein Data Bank of antibodies and other binders bound to HER2 were analyzed by superimposing the HER2 portion of the crystal structures (Trastuzumab, PDB ID: 1N8Z; Pertuzumab, PDB ID: 1S78; DARPin G3, PDB ID: 4HRN; and DARPin 9.29, PDB ID: 4HRL (see e.g., Cho et al., Nature 421, 756-60 (2003); Zhou et al., J Biol Chem 286, 31676-83 (2011); Fisher et al., J Mol Biol 402, 217-29 (2010); Eigenbrot et al., PNAS 107, 15039-44 (2010)). The superimposed structures are shown in FIG. 12. Four HER2 binders were selected based primarily on their non-competitive binding of HER2 (see FIG. 12). The selected binders included two antibodies (Trastuzumab and Pertuzumab) (Franklin et al., Cancer Cell 5, 317-28 (2004); Pegram et al., J Clin Oncol 16, 2659-71 (1998); Walshe et al., Clin Breast Cancer 6, 535-39 (2006); Plosker & Keam, Drugs 66, 449-75 (2006); Jost et al., Structure 21, 1979-91 (2013); Owen et al., J Control Release 172, 395-404 (2013); Lewis et al., Nat Biotechnol 32, 191-98 (2014); Epa et al., PLoS One 8, e59163 (2013); Zahnd et al., J Mol Biol 369, 1015-28 (2007); Carter et al., PNAS 89, 4285-89 (1992)) and two designed ankyrin repeated proteins (DARPins, G3 and 9.29). Both Trastuzumab and Pertuzumab are FDA-approved drugs for the treatment of HER2-positive breast cancer. As shown in FIG. 12, each of these binders binds to separate regions of the extracellular domain of HER2. While Trastuzumab binds domain IV close to the cell surface and does not interfere with HER2 oligomerization, Pertuzumab binds the protruding knob of domain II that is necessary for dimerization. Like Trastuzumab, DARPin G3 also binds domain IV, but binds the opposite side from the Trastuzumab binding site. DARPin 9.29 binds domain I adjacent to Pertuzumab, suggesting that these two binders would be suitable binding domains for a target-engaged complementation pair. All four of these proteins bind HER2 with high affinity ($K_D$ values between 0.09 nM and 3 nM), and do so on four distinct epitopes, suggesting that any two of them could yield a functional target-engaged complementation pair. As such, these binders were selected for screening. In addition to these binders that bind to characterized epitopes, an additional antibody that has not been crystallized but is known to not compete with Trastuzumab for binding—73J—was also screened.

To screen for functional target-engaged complementation pairs, constructs were designed in which each peptide fragment is fused to all five binders (either on the N- or C-terminus). For the antibodies, a fragment antigen binding fragment (Fab) was used, providing the opportunity to make a fusion at either of the light or heavy chain termini. Selecting one of each of the N- and C-termini produced a set of fusion protein fragments for screening (10 fusions with β9×10 fusions with β10* for a total of 100 possible pairs). For each of these fusions, a linker of 18 amino acids (SEQ ID NO 4) was used between the binder and the peptide. If fully extended, the linker is capable of spanning ~70 angstroms, suggesting that the termini of each binding pair should be within ~140 angstroms. As determined by molecular modeling, and shown in Table 1 (below), all pairs of termini are within this distance. (The measured distances ranged from 43-141 angstroms.)

TABLE 1

| | Distance between potential binding pairs (angstroms) | | | | | | | | | |
|---|---|---|---|---|---|---|---|---|---|---|
| | β9-LPert | PertH-β9 | β9-HTras | TrasH-β9 | β9-L73J | 73JH-β9 | β9-9.29 | 9.29-β9 | β9-G3 | G3-β9 |
| β10*-LPert | | | 47 | 43 | | | 67 | 56 | 97 | 66 |
| PertH-β10* | | | 92 | 93 | | | 69 | 52 | 141 | 121 |
| β10*-HTras | 47 | 92 | | | | | 93 | 100 | 47 | 55 |

TABLE 1-continued

| | Distance between potential binding pairs (angstroms) | | | | | | | | |
|---|---|---|---|---|---|---|---|---|---|
| | β9-LPert | PertH-β9 | β9-HTras | TrasH-β9 | β9-L73J | 73JH-β9 | β9-9.29 | 9.29-β9 | β9-G3 | G3-β9 |
| TrasH-β10* | 43 | 93 | | | | | 108 | 97 | 111 | 73 |
| β10*-L73J | | | | | | | | | | |
| 73JH-β10* | | | | | | | | | | |
| β10*-9.29 | 67 | 69 | 93 | 108 | | | | | 102 | 87 |
| 9.29-β10* | 56 | 52 | 100 | 97 | | | | | 132 | 104 |
| β10*-G3 | 97 | 141 | 47 | 111 | | | 102 | 132 | | |
| G3-β10* | 66 | 121 | 55 | 73 | | | 87 | 104 | | |

To identify functional target-engaged complementation pairs, all 20 fusions were expressed in *E. coli*. The SEQ ID numbers corresponding to nucleotide sequences and amino acid sequences for the fusion proteins are set forth in Table 2.

TABLE 2

| | Sequence Listings |
|---|---|
| β9-L73J | SEQ ID NO 5 (nucleotide) |
| | SEQ ID NO 6 (amino acid: β9-His Tag-light chain) |
| | SEQ ID NO 7 (amino acid: heavy chain) |
| β10*-L73J | SEQ ID NO 8 (nucleotide) |
| | SEQ ID NO 9 (amino acid: β10*-His Tag-light chain) |
| | SEQ ID NO 10 (amino acid: heavy chain) |
| 73JH-β9 | SEQ ID NO 11 (nucleotide) |
| | SEQ ID NO 12 (amino acid: light chain) |
| | SEQ ID NO 13 (amino acid: heavy chain-His Tag-β9) |
| 73JH-β10* | SEQ ID NO 14 (nucleotide) |
| | SEQ ID NO 15 (amino acid: light chain) |
| | SEQ ID NO 16 (amino acid: heavy chain-His Tag-β9) |
| β9-HTras | SEQ ID NO 17 (nucleotide) |
| | SEQ ID NO 18 (amino acid: light chain) |
| | SEQ ID NO 19 (amino acid: β9-His Tag-heavy chain) |
| β10*-HTras | SEQ ID NO 20 (nucleotide) |
| | SEQ ID NO 21 (amino acid: light chain) |
| | SEQ ID NO 22 (amino acid: β10*-His Tag-heavy chain) |
| TrasH-β9 | SEQ ID NO 23 (nucleotide) |
| | SEQ ID NO 24 (amino acid: light chain) |
| | SEQ ID NO 25 (amino acid: heavy chain-His Tag-β9) |
| TrasH-β10* | SEQ ID NO 26 (nucleotide) |
| | SEQ ID NO 27 (amino acid: light chain) |
| | SEQ ID NO 28 (amino acid: heavy chain-His Tag-β10*) |
| β9-LPert | SEQ ID NO 29 (nucleotide) |
| | SEQ ID NO 30 (amino acid: β9-His Tag-light chain) |
| | SEQ ID NO 31 (amino acid: heavy chain) |
| β10*-LPert | SEQ ID NO 32 (nucleotide) |
| | SEQ ID NO 33 (amino acid: β10*-His Tag-light chain) |
| | SEQ ID NO 34 (amino acid: heavy chain) |
| PertH-β9 | SEQ ID NO 35 (nucleotide) |
| | SEQ ID NO 36 (amino acid: light chain) |
| | SEQ ID NO 37 (amino acid: heavy chain-His Tag-β9) |
| PertH-β10* | SEQ ID NO 38 (nucleotide) |
| | SEQ ID NO 39 (amino acid: light chain) |
| | SEQ ID NO 40 (amino acid: heavy chain-His Tag-β10*) |
| β9-G3 | SEQ ID NO 41 (nucleotide) |
| | SEQ ID NO 42 (amino acid: β9-His Tag-G3) |
| β10*-G3 | SEQ ID NO 43 (nucleotide) |
| | SEQ ID NO 44 (amino acid: β10*-His Tag-G3) |
| G3-β9 | SEQ ID NO 45 (nucleotide) |
| | SEQ ID NO 46 (amino acid: His Tag-G3-β9) |
| G3-β10* | SEQ ID NO 47 (nucleotide) |
| | SEQ ID NO 48 (amino acid: His Tag-G3-β10*) |
| β9-9.29 | SEQ ID NO 49 (nucleotide) |
| | SEQ ID NO 50 (amino acid: β9-His Tag-9.29) |
| β10*-9.29 | SEQ ID NO 51 (nucleotide) |
| | SEQ ID NO 52 (amino acid: β10*-His Tag-9.29) |
| 9.29-β9 | SEQ ID NO 53 (nucleotide) |
| | SEQ ID NO 54 (amino acid: 9.29-His Tag-β9) |
| 9.29-β10* | SEQ ID NO 55 (nucleotide) |
| | SEQ ID NO 56 (amino acid: 9.29-His Tag-β10*) |

The cells were then lysed, and the concentration was normalized through luminescence. All possible pairs were screened on HER2+ SKOV3 cells. More particularly, cells were incubated with the two binder fusion proteins at ambient temperature. The cells were then washed, Δ11 S and substrate (furimazine) were added, and luminescence was measured. The results are shown in FIGS. 13A-14B, with the −SKOV3 cells of FIGS. 14A and 14B serving as a control.

The average signal-to-background results from this screen (as performed on three separate days) are summarized in Table 3.

TABLE 3

| Signal-to-Background Measurements (Ratio of Relative Luminescence Units) | | | | | | | | | |
|---|---|---|---|---|---|---|---|---|---|
| | β9-LPert | PerH-β9 | β9-HTras | TrasH-β9 | β9-L73J | 73JH-β9 | β9-9.29 | 9.29-β9 | β9-G3 | G3-β9 |
| β10*-LPert | 0 ± 0 | 0 ± 0 | 3 ± 2 | 1 ± 1 | 1 ± 1 | 1 ± 1 | 2 ± 1 | 2 ± 2 | 2 ± 0 | 3 ± 1 |
| PerH-β10* | 4 ± 3 | 11 ± 4 | 211 ± 81 | 128 ± 31 | 367 ± 221 | 38 ± 17 | 671 ± 284 | 345 ± 130 | 65 ± 29 | 122 ± 80 |
| β10*-HTras | 108 ± 78 | 11 ± 12 | 80 ± 49 | 6 ± 4 | 7 ± 2 | 18 ± 13 | 167 ± 153 | 2 ± 1 | 5 ± 1 | 45 ± 26 |
| TrasH-β10* | 114 ± 104 | 40 ± 29 | 11 ± 7 | 6 ± 3 | 83 ± 71 | 9 ± 8 | 44 ± 22 | 60 ± 45 | 33 ± 26 | 61 ± 39 |
| β10*-L73J | 4 ± 4 | 12 ± 11 | 3 ± 1 | 6 ± 3 | 2 ± 1 | 3 ± 1 | 173 ± 208 | 9 ± 4 | 21 ± 23 | 126 ± 102 |
| 73JH-β10* | 23 ± 9 | 60 ± 37 | 170 ± 43 | 25 ± 12 | 6 ± 3 | 7 ± 2 | 81 ± 52 | 39 ± 26 | 219 ± 91 | 95 ± 35 |
| β10*-9.29 | 3 ± 1 | 31 ± 28 | 38 ± 26 | 5 ± 6 | 93 ± 72 | 4 ± 2 | 13 ± 13 | 1 ± 1 | 4 ± 4 | 12 ± 6 |
| 9.29-β10* | 265 ± 137 | 346 ± 135 | 40 ± 4 | 29 ± 14 | 597 ± 352 | 13 ± 5 | 99 ± 49 | 5 ± 3 | 122 ± 84 | 75 ± 48 |
| 8 β10* | 32 ± 8 | 21 ± 20 | 87 ± 45 | 15 ± 10 | 197 ± 80 | 21 ± 14 | 36 ± 13 | 11 ± 12 | 7 ± 3 | 28 ± 12 |
| G3-β10* | 353 ± 63 | 103 ± 62 | 508 ± 108 | 118 ± 58 | 1358 ± 455 | 47 ± 29 | 19 ± 12 | 31 ± 27 | 12 ± 7 | 93 ± 37 |

Within this set, each pair was tested with both possible orientations of the peptides (e.g., G3-β10*:TrasH-β9 and G3-β9:TrasH-β10*). There was little correlation between the results obtained upon swapping the peptide fused to each binder. Furthermore, only four of the top 20 pairs involved β9 as a C-terminal fusion. Similarly, four (but not the same four found with C-terminal β9) out of the top 20 pairs involved β10* as an N-terminal fusion. Together, the data suggest that the complementation system functions preferentially, but not exclusively, when β9 is an N-terminal fusion and β10* is a C-terminal fusion. Twenty-three pairs produced a signal (relative luminescence units) at least 100-fold higher than background. The top two pairs—β9-L73J:G3-β10* and β9-9.29:PertH-β10*—were selected for further characterization and analysis.

Validation of Target-Engaged Complementation

Figure 15:
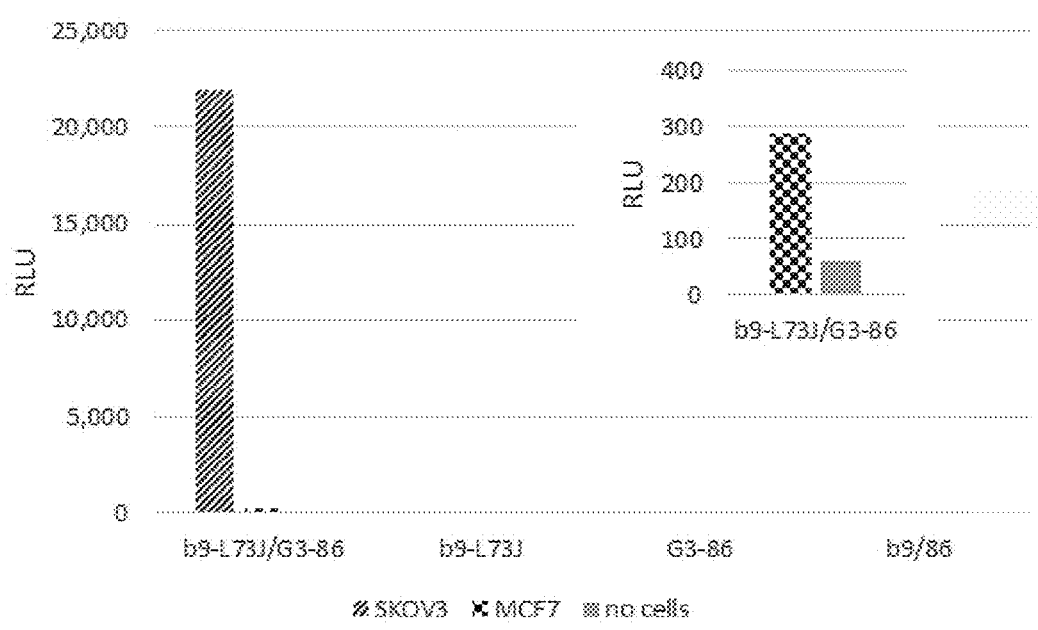
FIG. 15 is a bar graph depicting luminescent activity of various split enzyme reporter systems.
Figure 16:
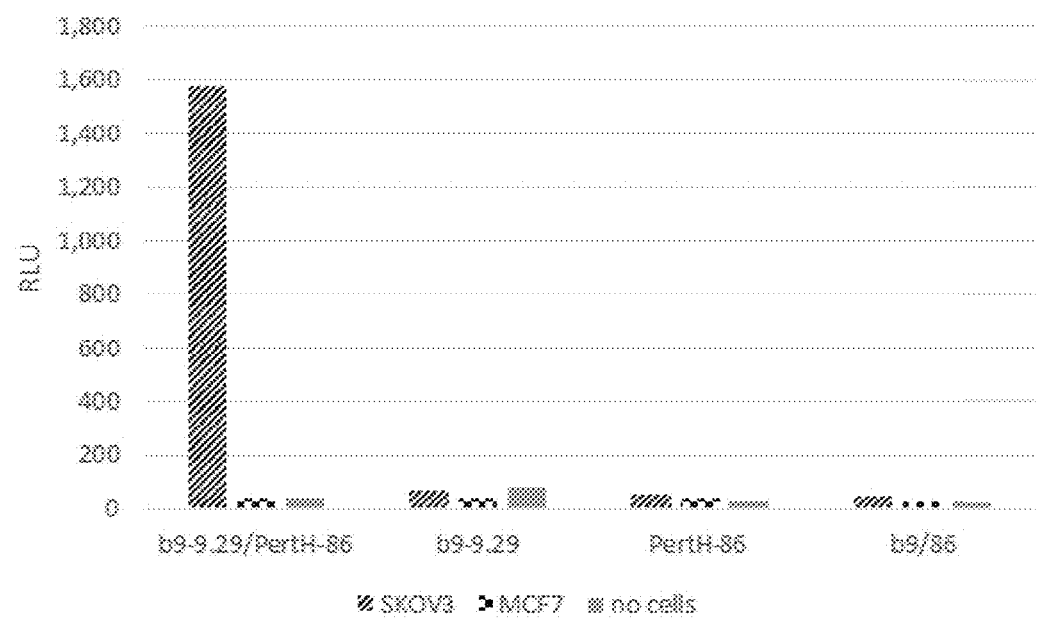
FIG. 16 is a bar graph depicting luminescent activity of various split enzyme systems.

Unpurified antibody and DARPin fusions (β9-L73J:G3-β10* and β9-9.29:PertH-β10*) from lysates were validated by their binding to HER2+ SKOV3 cells as described above. As shown in FIGS. 15-16, in the absence of HER2 (no cells), negligible signal is generated. Similarly, no significant luminescence was produced when less than all of the components of the fragment complementation system were added. However, when the proper pair of fusion proteins was introduced into the system, a luminescent signal was produced. The assay also distinguished between low (MCF-7) and high (SKOV3) HER2 expressing cells. See FIGS. 15-16.

Subsequently, the same assay was run with purified fusion proteins. More particularly, the β9-L73J:G3-β10* and β9-9.29:PertH-β10* fusion proteins were produced recombinantly in E. coli. Each of these fusion proteins included a His-Tag, enabling purification using standard immobilized metal affinity chromatography (IMAC) procedures. Block et al., 463 Methods Enzymol 439-73 (2009). The purified proteins retained ≥90% of the activity of the originating lysate, even after storage for over one month.

Figure 17:
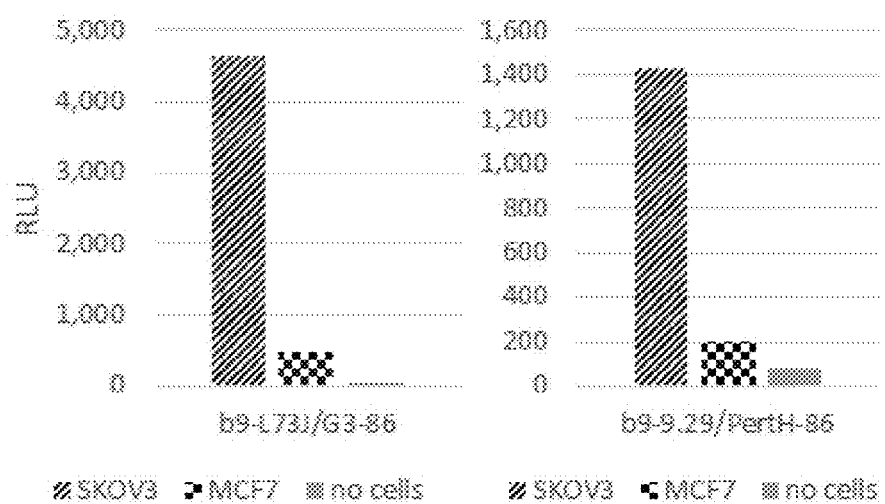
FIG. 17 is a bar graph depicting luminescent activity of two targeted split enzyme reporter systems using purified fusions.
Figure 18:
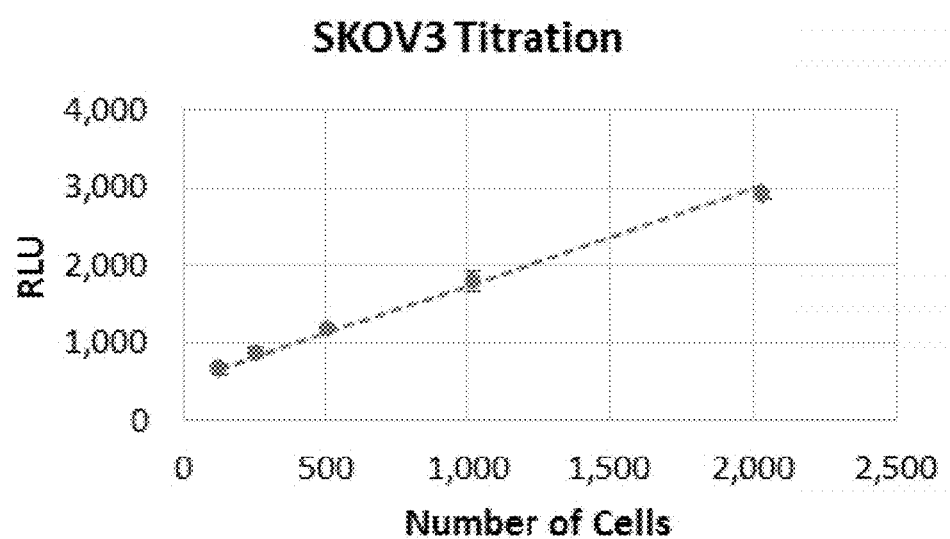
FIG. 18 is a plot showing luminescent activity as a function of the number of HER2$^+$ cells.

The data for the purified fusion proteins is shown in FIGS. 17 and 18. As shown in these figures, the purified proteins could be used to detect and quantify HER2, and could be used to differentiate between low (MCF-7) and high (SKOV3) HER2-expressing cells.

Immunoassay without Wash Step

HER2+ SKOV3 cells were introduced into wells of a multi-well plate. β9-binder, β10*-binder, Δ11S, and furimazine were added to each well. In contrast to other HER2 assays described herein, the unbound antibodies were not washed away. In other words, luminescence was detected without any intervening wash step.

Figure 19:
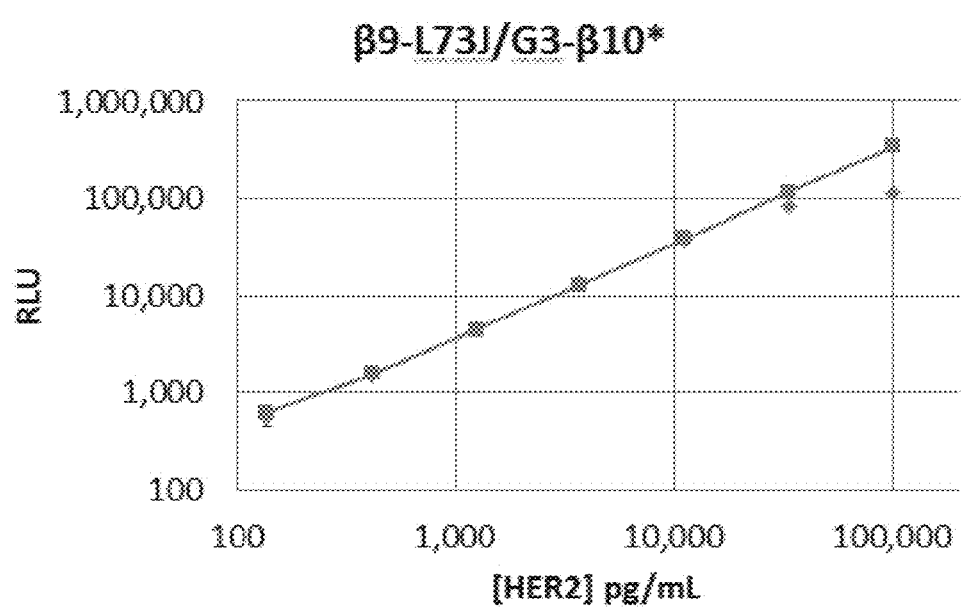
FIG. 19 is a plot showing luminescent activity of a targeted split enzyme reporter system as a function of HER2 concentration.
Figure 20:
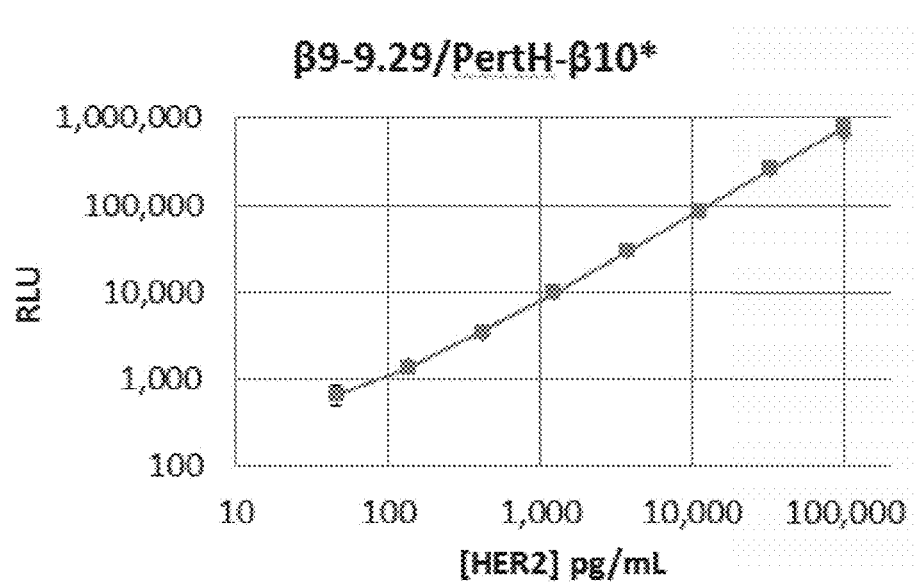
FIG. 20 is a plot showing luminescent activity of another targeted split enzyme reporter system as a function of HER2 concentration.

The concentration of each fusion protein was tailored so as to provide sufficient binder to bind the antigen (i.e., HER2) while keeping the concentration of the peptide relatively low so as to minimize complementation (and background signal) in the absence of the antigen. To this end, the concentration of each fusion in both target-engaged complementation pairs was optimized. Low nM concentrations were found to be appropriate. The resulting luminescence data collected two hours after incubation is shown in FIGS. 19-20. More particularly, FIG. 19 provides data for β9-L73J/G3-β10* target-engaged complementation. And FIG. 20 provides data for β9-9.29/PertH-β10* target-engaged complementation.

Figure 21:
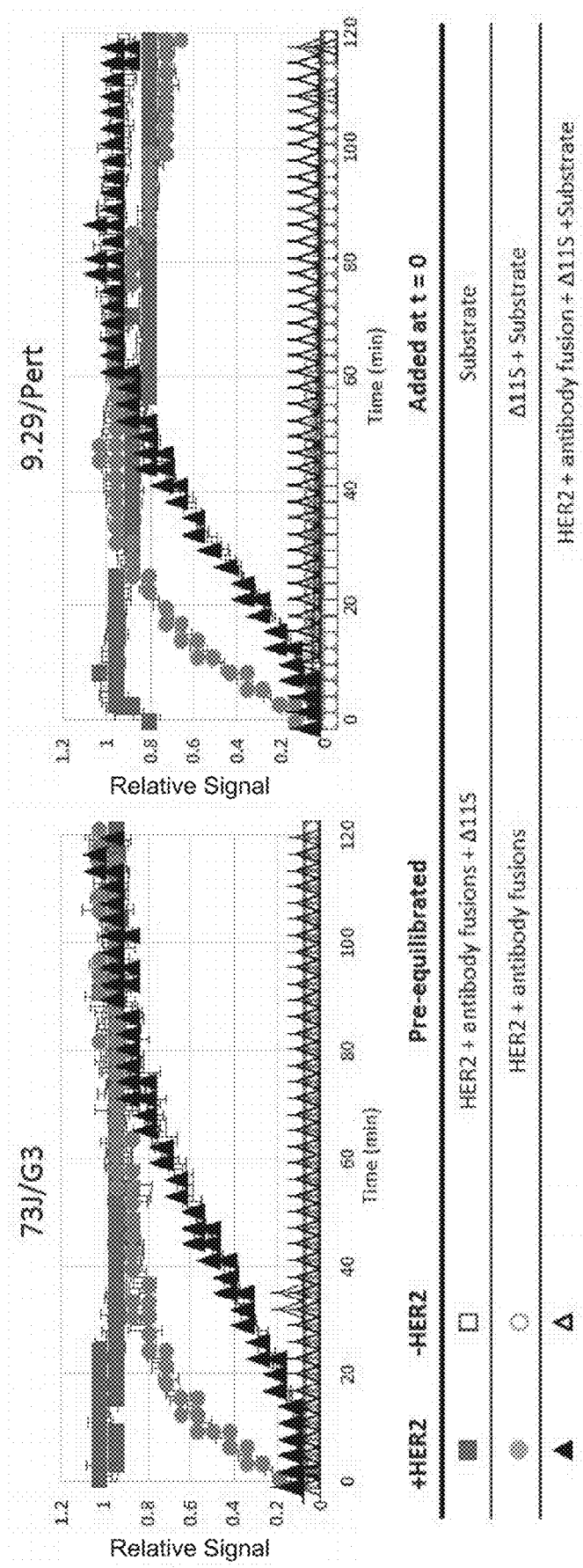
FIG. 21 includes scatterplots that illustrate the binding kinetics of components of a targeted split enzyme reporter system.

In assays such as this one, where each of the three components of the tripartite split enzyme are added at once, the binding kinetics may influence the optimal time for measuring luminescence. In addition to binding of the targeting domain (e.g., Fab or DARPin) to the analyte (e.g., HER2), Δ11S also needs to bind to β9/β10* to form the active luciferase complex. To evaluate when to measure the signal and to differentiate binding of the targeting domain from formation of the luciferase complex, kinetics studies were performed. As shown in FIG. 21, the signal kinetics from an experiment where each component of the target-engaged complementation system (and substrate) is simultaneously added to the mixture (HER2+β9-binder+β10*-binder+Δ11S+substrate; solid triangles) were compared to the kinetics where (1) both targeting domains (but not Δ11S or substrate) were pre-equilibrated with HER2 (HER2+β9-binder+β10*-binder) (closed circles) and (2) both targeting domains and Δ11S (but not substrate) were pre-equilibrated with HER2 (HER2+β9-binder+β10*-binder+Δ11S) (solid squares). When all components are pre-equilibrated with HER2 (solid squares), luminescence is immediately obtained. If Δ11S is not pre-equilibrated, but added with substrate to pre-equilibrated targeting domains (solid circles and solid triangles), the luminescent signal increases with time according to Δ11S binding and/or the formation of an active luciferase complex. The formation of the luciferase complex is slower for the 73J/G3 combination, reaching approximately 90% of the maximal signal at ~50 minutes, as compared to ~30 minutes for 9.29/Pertuzumab. Among other possibilities, this difference in rate may be a reflection of a larger distance of separation between the fused termini. As expected, when the targeting domains are not pre-equilibrated with HER2, an increased time was required to achieve the maximal signal, consistent with the requirement for both targeting domain and Δ11S binding. The kinetics data demonstrate that the maximal signal is obtained within two hours. Furthermore, for 9.29/Pertuzumab, signal-to-background of five was obtained within 20 minutes, demonstrating the feasibility of this relatively fast and simple single-step assay.

To determine the sensitivity of the assay, the following definitions were noted as outlined by Armbruster and Pry (Armbruster & Pry, *Clin Biochem Rev* 29 Suppl 1, S49-52 (2008)):

$$\text{Limit of Blank (LoB)} = \text{mean } RLU_{blank} + 1.645 \times SD_{blank}$$

$$\text{Limit of Detection (LoD)} = \text{LoB} + 1.645 \times SD_{low\ concentration\ sample}$$

As opposed to using the definition for the limit of detection and extrapolating to a concentration that had not actually been tested, the LoD was defined as the lowest concentration measured that produced a signal greater than the LoB+1.645 times the standard deviation. For 73J/G3, the LoD was 137 pg/mL and the linear range extended up to a concentration of 11 ng/mL. The combination of 9.29 and Pertuzumab was found to exceed these capabilities in terms of both the limit of detection and the linear range. The LoD for this pair was determined to be 45 pg/mL. Although 100 ng/mL seems to be close to lying within the linear range, the small standard deviation of this assay would suggest that it does not, and the highest concentration assayed that remained in the linear range was 33 ng/mL. A previous demonstration using complementation to detect HER2 reported the ability to detect 500 μM HER2 (Stains et al. *ACS Chem Biol* 5, 943-52 (2010)). These results demonstrate the ability to detect sub-picomolar concentrations (0.7 pM), an improvement of approximately 500-fold. Further, commercially available ELISA kits report sensitivities in the range of 8-24 pg/mL with linear ranges up to approximately 5 ng/mL. The sensitivity and dynamic range demonstrated here is comparable to the sensitivity and dynamic range of these commercially available ELISA assays. This is particularly impressive, considering that many standard ELISA kits involve signal amplification by binding multiple antibodies per antigen and/or multiple enzymes per antibody. In contrast, for every pair of bound targeting domains, the signal demonstrated here is limited to the signal generated from a single active luciferase complex that is formed via target-engaged complementation.

Analyte Detection in Human Serum

Figure 22:
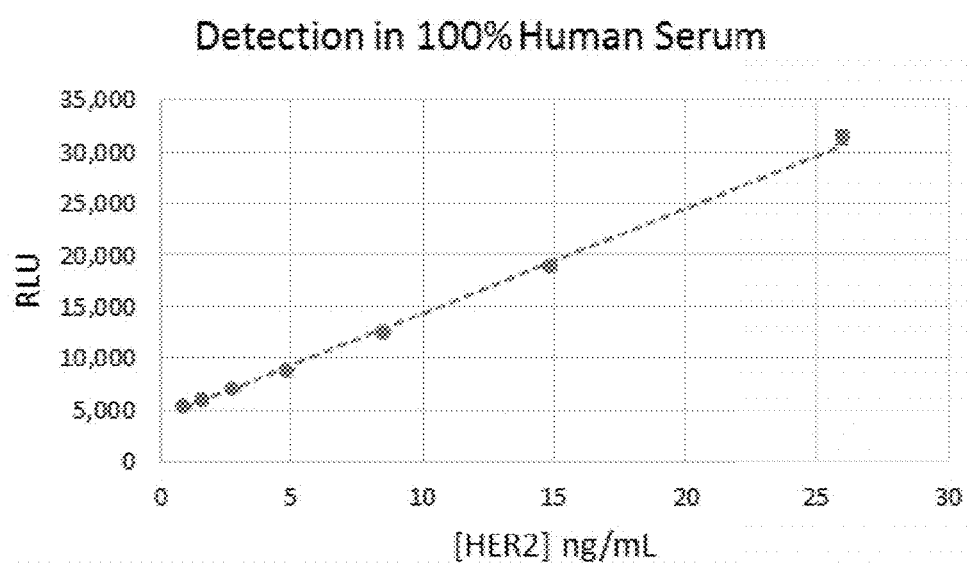
FIG. 22 is a graph showing luminescent activity as a function of HER2 concentration in human serum.

As soluble HER2 may be used to monitor the treatment efficacy and recurrence of cancer (see, e.g., Tse et al., *Cancer Treat Rev* 38, 133-42 (2012); Mokuyasu et al., *Rinsho Byori* 60, 612-20 (2012); Cook et al., *Anticancer Res* 21, 1465-70 (2001)), a target-engaged complementation reporter was used to investigate detection of HER2 in human serum. As the threshold for elevated HER2 in serum has been established at ≥15 ng/mL, HER2 was spiked into human serum at low ng/mL concentrations. A target-engaged complementation assay was then performed using the combination of 9.29 and Pertuzumab (for β9-9.29/PertH-β10*). Given the complex nature and high concentration of proteins in serum, serum is a particularly challenging mixture for a solution-based application of target-engaged complementation. Despite these challenges, target-engaged complementation successfully differentiated between small differences in HER2 concentrations and was linear across the low ng/mL range as shown in FIG. 22. This demonstrates that target-engaged complementation can be used to differentiate between biologically relevant concentrations of HER2 in human serum.

The foregoing data show that HER2 can be quantified via a simple, rapid, and sensitive method. The method is generalizable to other analytes (e.g., proteins) of interest. Further, while the data disclosed herein is most analogous to a traditional ELISA, analogous methods may be used in immunocytochemistry and immunohistochemistry as well.

Figure 23:
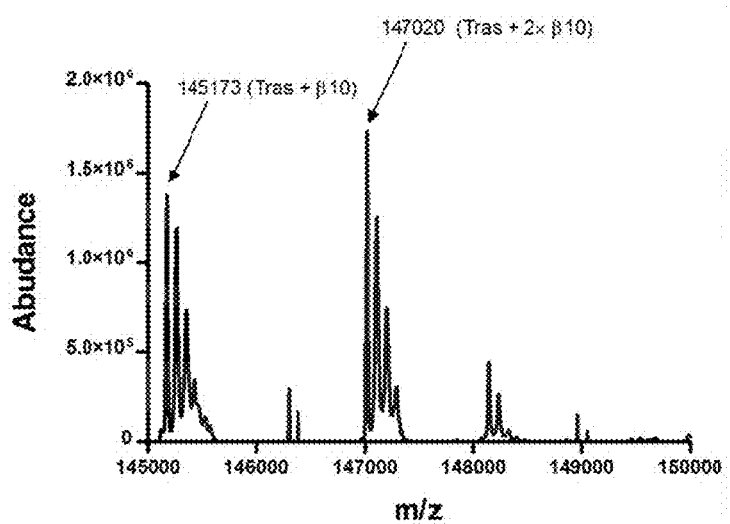
FIG. 23 provides mass spectrometry data of a chemically conjugated agent that includes a peptide fragment and a targeting domain.
Figure 24:
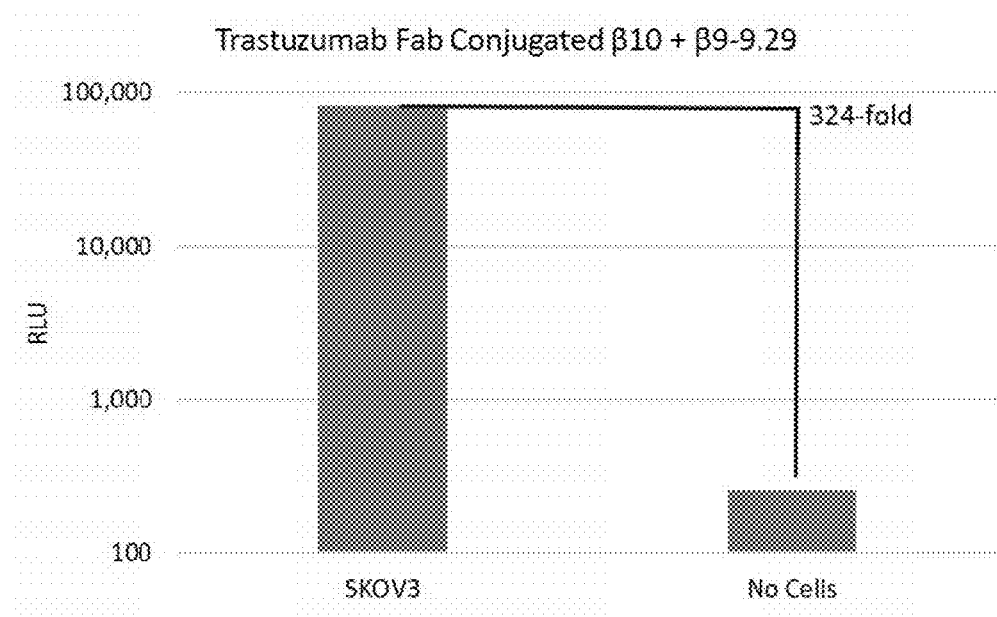
FIG. 24 is a bar graph showing luminescence from a targeted split enzyme reporter system that includes a chemically conjugated peptide fragment.

Target-Engaged Complementation with Split Enzyme Fragments that are Produced by Chemical Conjugation A maleimide-β10* peptide was chemically conjugated to the full IgG form of Trastuzumab using 2-iminothiolane. Conjugation was verified by mass spectrometry as shown in FIG. 23. The mass spectrometry data showed that either one or two β10* fragments were conjugated per antibody. The utility of the chemically conjugated fragment for use in target-engaged complementation was then investigated by combining the chemically conjugated fragment with complementary peptide fragments (β9-9.29 and Δ11S) in the presence and the absence of HER2+ cells (SKOV3). The results are shown in FIG. 24. A 324-fold increase in signal was observed in the presence of HER2$^+$ cells, demonstrating that a chemically conjugated peptide fragment can be used for target-engaged complementation.

Figure 25:
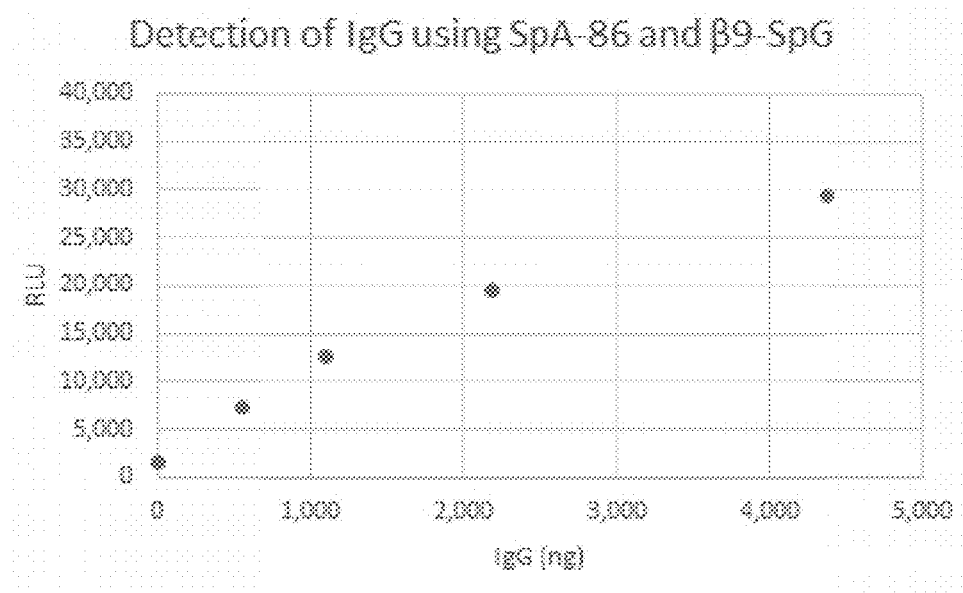
FIG. 25 is a scatterplot showing luminescent detection of IgG with a split enzyme reporter system having a first peptide fragment that is conjugated to Protein A and a second peptide fragment that is conjugated to Protein G.
Figure 26:
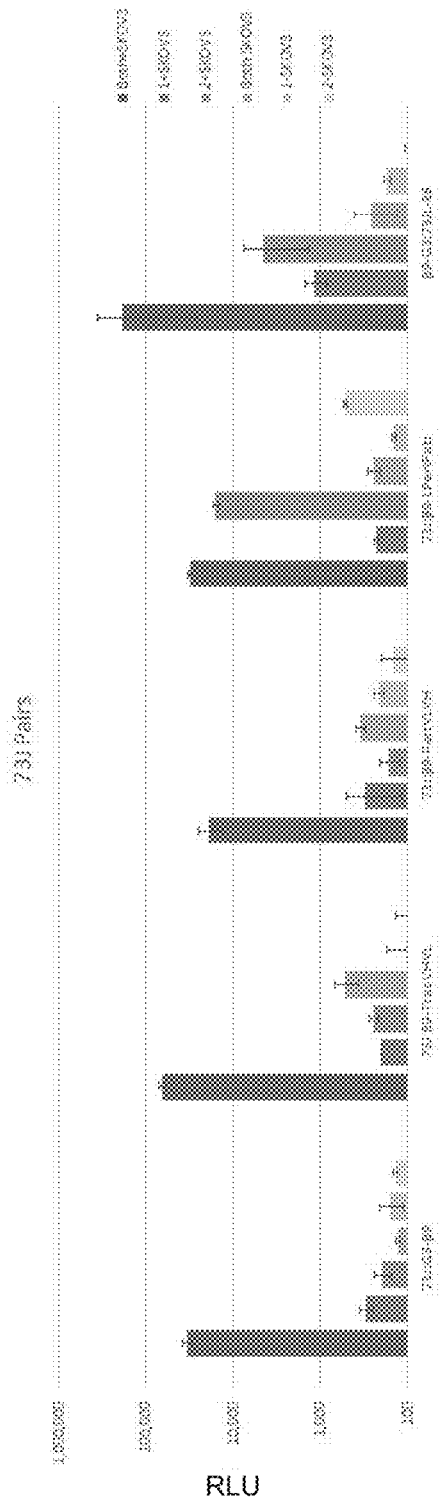
FIG. 26 is a bar chart showing luminescence generated by various targeted split reporter systems.
Figure 27:
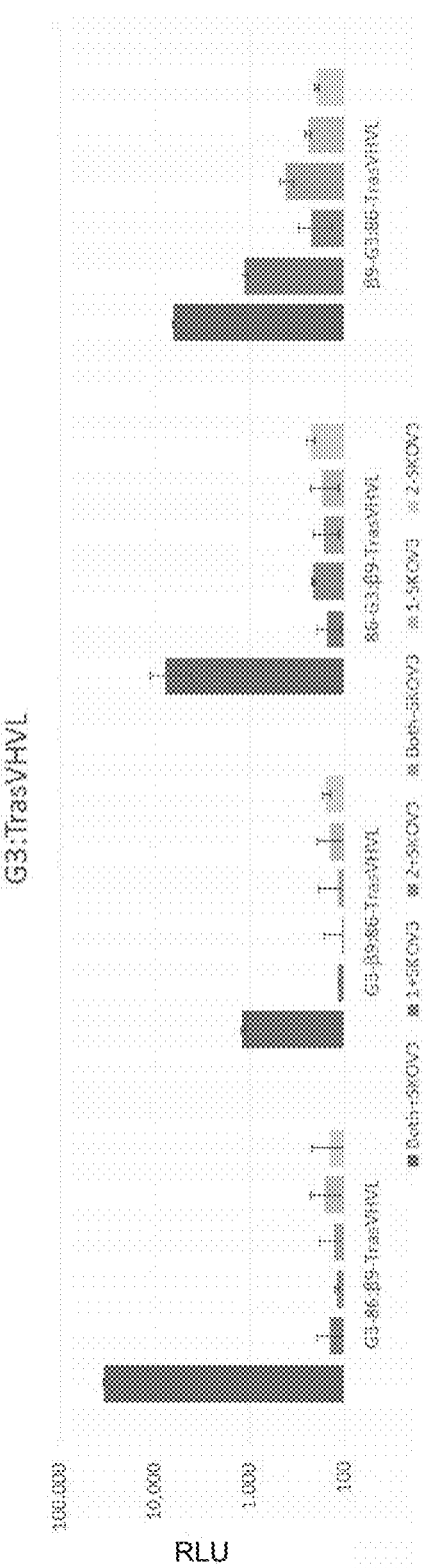
FIG. 27 is a bar chart showing luminescence generated by various targeted split reporter systems.
Figure 28:
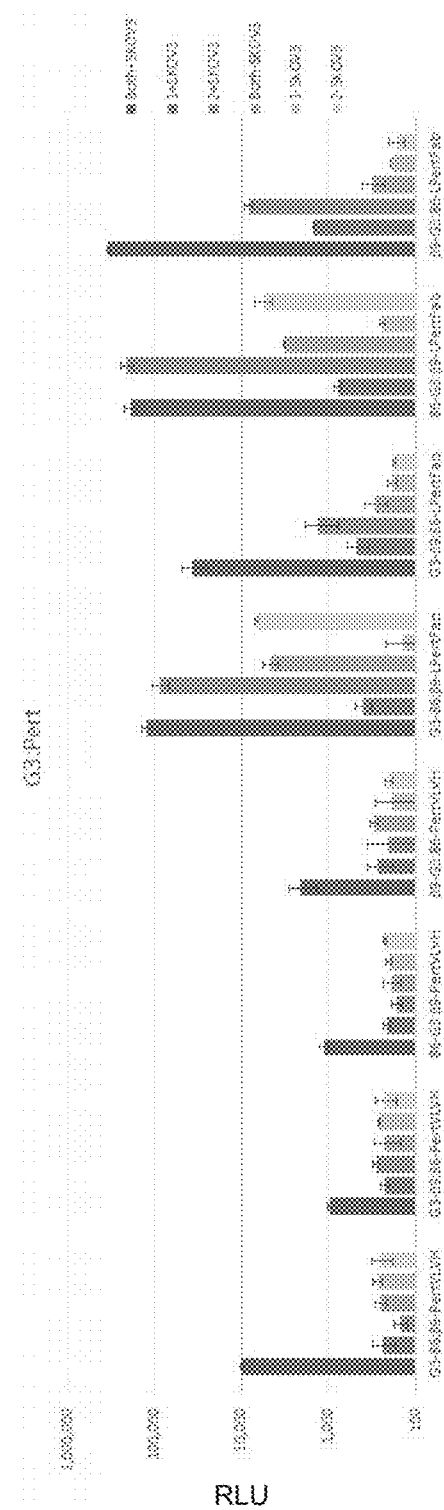
FIG. 28 is a bar chart showing luminescence generated by various targeted split reporter systems.
Figure 29:
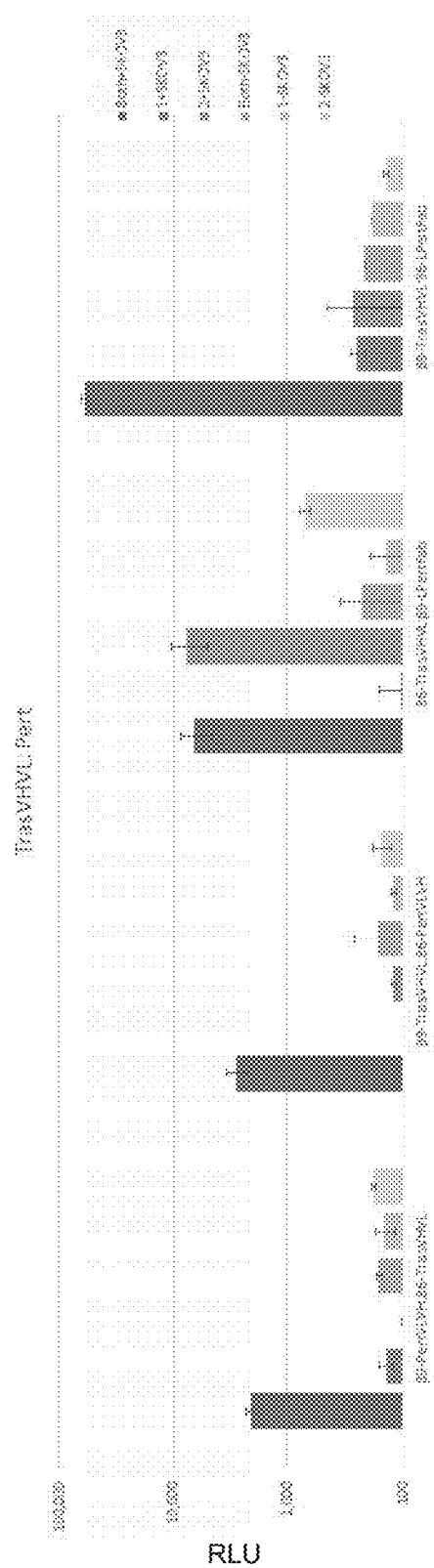
FIG. 29 is a bar chart showing luminescence generated by various targeted split reporter systems.

Target-Engaged Complementation Using Protein a and Protein G as Targeting Domains A split reporter system was used to detect IgG in solution. More specifically, a Protein A-β10* fusion protein and a Protein G-β9 fusion protein were produced recombinantly. The ability of these peptide fragments to detect IgG (based on the affinity of Protein A and Protein G for IgG) was evaluated by target-engaged complementation. More specifically, the two fusion protein fragments were combined with Δ11S in the presence of various amounts of IgG, and luminescence was measured. The resulting data is shown in FIG. 25. The data show that increased luminescent signal is generated with increasing concentrations of IgG, and that this target-engaged complementation system can be used to assess IgG concentrations in solution.

Further Target-Engaged Complementation Studies

The various fusion proteins shown in FIGS. 26-29 were recombinantly produced. More particularly, 73J and PertFab domains were produced as Fabs, G3 was produced as a DARPin, and TrasVHVL and PertVLVH were produced as single-chain variable fragments (scFv). Each fragment of each split enzyme reporter system was combined with various other fragments of the split enzyme reporter system. For example, as shown in the first set of bar graphs of FIG. 26 for 73J-β10*:G3-β9, each of the following combinations of elements was combined with Δ11S and substrate in either the presence or the absence of HER2$^+$ cells: (1) 73J-β10* and G3-β9, (2) 73J-β10* alone, and (3) G3-β9 alone. Similar tests were carried out for twenty other protein complexes. The results shown in FIGS. 26-29 show that a wide variety of different targeting domains may be used for target-engaged complementation.

Detection of Adalimumab

Embodiments of the protein-fragment complementation system described herein (see FIG. 7 for a representative depiction) were used to detect adalimumab (also known as Humira), which is a monoclonal antibody with affinity to an epitope of tumor necrosis factor (TNF), also known as tumor necrosis factor alpha (TNFα). For instance, fusion proteins were created, where each fusion protein included both (1) a targeting domain (e.g., TNF, protein L, or Protein A) with affinity for adalimumab and (2) a peptide fragment (β9 or β10*) of a split reporter protein.

More particularly, Protein A (SpA), Protein L (PpL), and TNF (as a fusion to HaloTag® ("HT")) were expressed in *E. coli* (T7 SHuffle Express) as fusions with β9 or β10* at the N- or C-terminus. A lysate was prepared by sonicating the cells and centrifuging to separate out the insoluble material. Each TNF lysate was tested in combination with the opposite peptide (β9 with β10, or β10 with β9) fusion of Protein A and Protein L diluted in PBST. The luminescence produced in the absence (−Adal) or presence (+Adal) of 10 µg/mL adalimumab is shown in the bar graph of FIG. 30. The values shown are the averages from three replicate wells±standard deviation. The sequence listings for some of the fusion proteins (and corresponding nucleotide sequences) are identified in Table 4.

TABLE 4

Sequence Listings

| | |
|---|---|
| HT-β9-TNF | SEQ ID NO 57 (nucleotide) |
| | SEQ ID NO 58 (amino acid) |
| HT-TNF-β9 | SEQ ID NO 59 (nucleotide) |
| | SEQ ID NO 60 (amino acid) |
| HT-β10*-TNF | SEQ ID NO 61 (nucleotide) |
| | SEQ ID NO 62 (amino acid) |
| HT-TNF-β10* | SEQ ID NO 63 (nucleotide) |
| | SEQ ID NO 64 (amino acid) |
| β9-TNF | SEQ ID NO 65 (nucleotide) |
| | SEQ ID NO 66 (amino acid) |
| TNF-β9 | SEQ ID NO 67 (nucleotide) |
| | SEQ ID NO 68 (amino acid) |
| β10*-TNF | SEQ ID NO 69 (nucleotide) |
| | SEQ ID NO 70 (amino acid) |
| TNF-β10* | SEQ ID NO 71 (nucleotide) |
| | SEQ ID NO 72 (amino acid) |
| β9-PpL | SEQ ID NO 73 (nucleotide) |
| | SEQ ID NO 74 (amino acid) |
| PpL-β9 | SEQ ID NO 75 (nucleotide) |
| | SEQ ID NO 76 (amino acid) |
| β10*-PpL | SEQ ID NO 77 (nucleotide) |
| | SEQ ID NO 78 (amino acid) |
| PpL-β10* | SEQ ID NO 79 (nucleotide) |
| | SEQ ID NO 80 (amino acid) |
| β9-SpA | SEQ ID NO 81 (nucleotide) |
| | SEQ ID NO 82 (amino acid) |
| SpA-β9 | SEQ ID NO 83 (nucleotide) |
| | SEQ ID NO 84 (amino acid) |
| β10*-SpA | SEQ ID NO 85 (nucleotide) |
| | SEQ ID NO 86 (amino acid) |
| SpA-β10* | SEQ ID NO 87 (nucleotide) |
| | SEQ ID NO 88 (amino acid) |
| β9-SpGA1 | SEQ ID NO 89 (nucleotide) |
| | SEQ ID NO 90 (amino acid) |
| SpGA1-β9 | SEQ ID NO 91 (nucleotide) |
| | SEQ ID NO 92 (amino acid) |
| β10*-SpGA1 | SEQ ID NO 93 (nucleotide) |
| | SEQ ID NO 94 (amino acid) |
| SpGA1-β10* | SEQ ID NO 95 (nucleotide) |
| | SEQ ID NO 96 (amino acid) |

Figure 30:
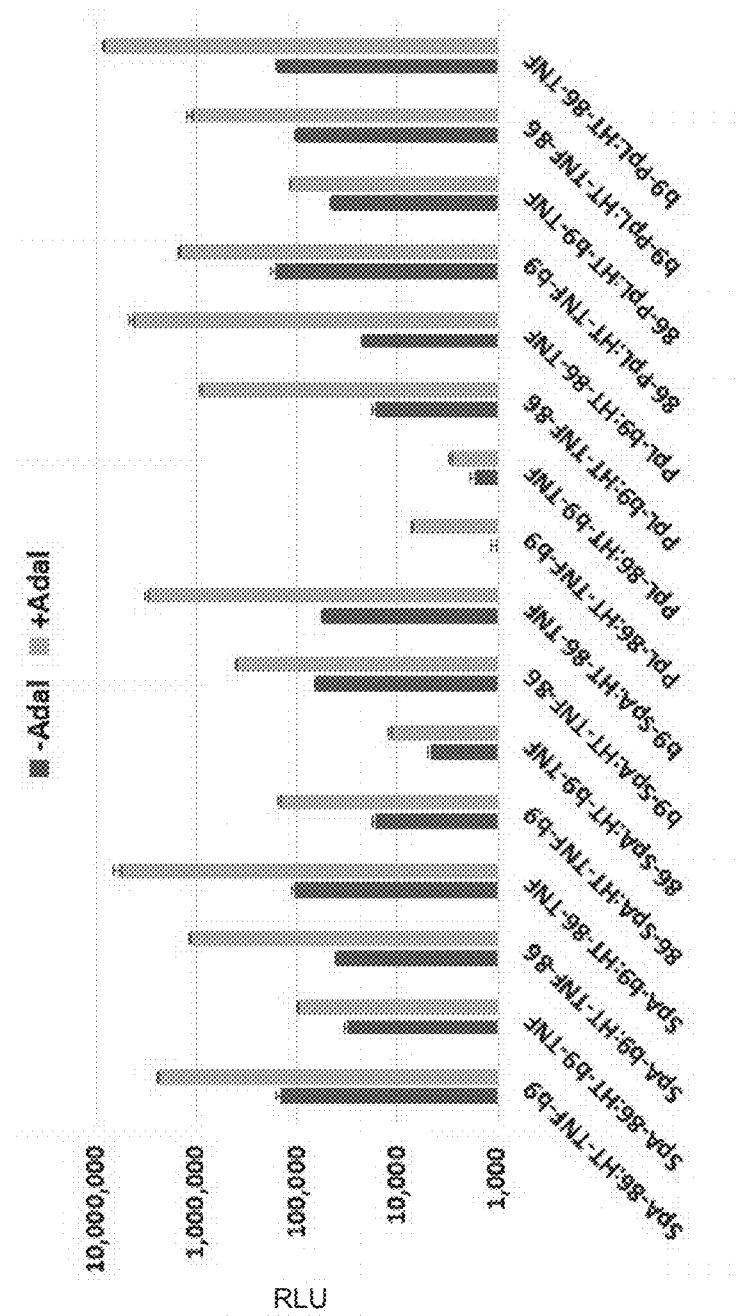
FIG. 30 is a bar chart showing luminescence generated by various targeted split enzyme reporter systems.
Figure 31:
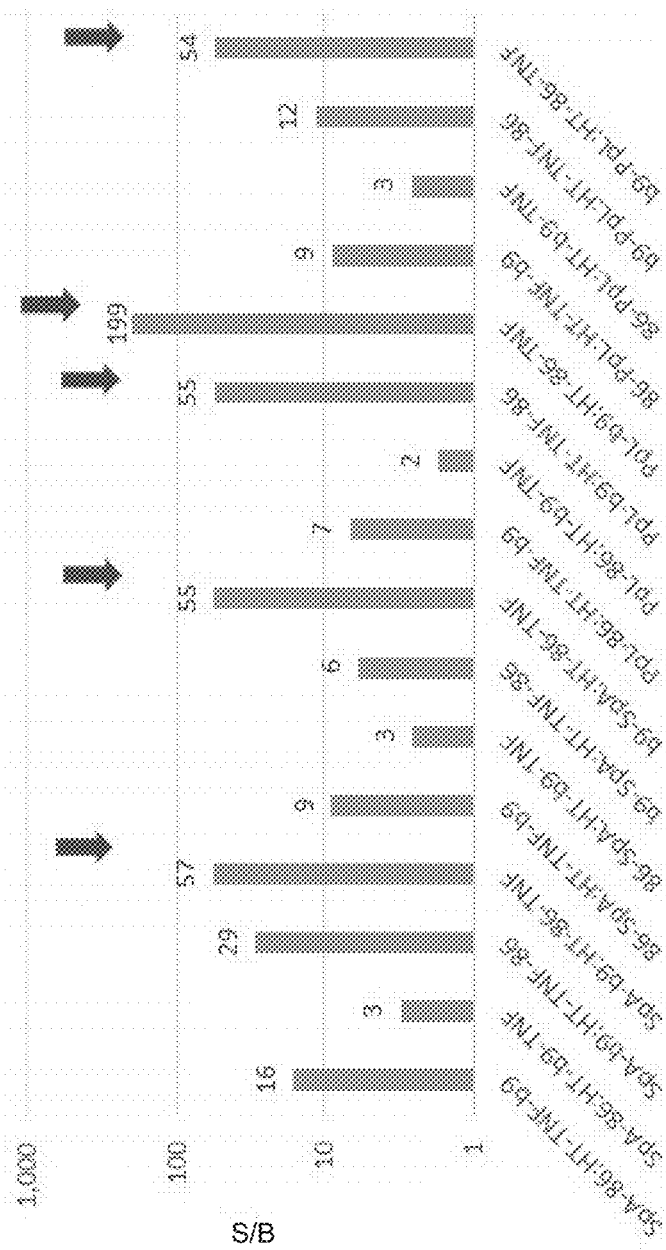
FIG. 31 is a bar chart showing the signal-to-background ratio for luminescence generated by the targeted split enzyme reporter systems of FIG. 32.

As shown in FIG. 30, increased luminescent signal was observed in the presence of adalimumab, demonstrating that the assay may be used to detect the antibody. The ratio of signal to noise for each pair of fusion proteins is shown in FIG. 31. Signal-to-background values were determined by dividing the luminescence produced in the presence of adalimumab (+Adal) by the luminescence produced in the absence of adalimumab (−Adal).

Four of the pairs of fusion proteins (protein A-β9:HT-β10*-TNF; β9-protein A: HT-β10*-TNF; protein L-β9: HT-TNF-β10*; protein L-β9:HT-β10*-TNF) were selected for further studies based on the high signal-to-noise ratio observed in the experiments reported in FIGS. 30 and 31.

Figure 32:
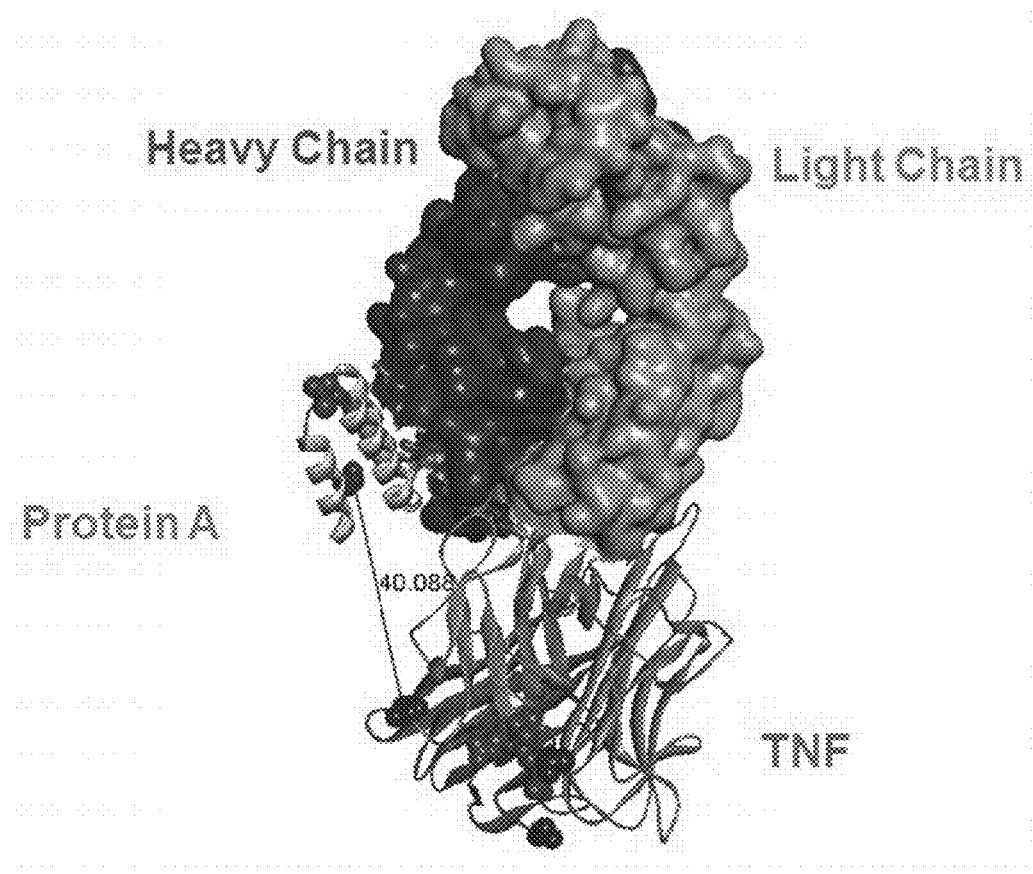
FIG. 32 is a structural model showing the binding of protein A and tumor necrosis factor (TNF) to adalimumab.
Figure 33:
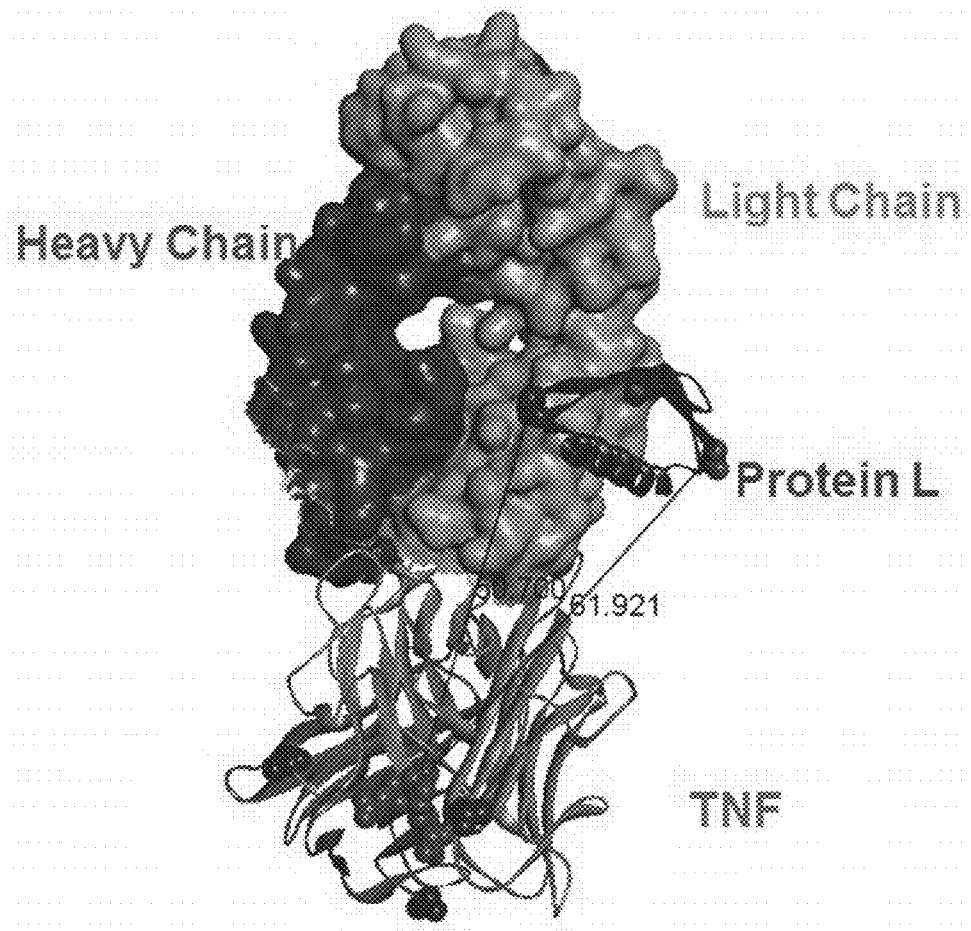
FIG. 33 is a structural model showing the binding of protein L and tumor necrosis factor to adalimumab.

For example, the four pairs of fusion proteins were used to detect adalimumab and infliximab (another antibody with affinity for TNF). Infliximab is shown bound to TNF and protein A in FIG. 32 and bound to TNF and protein L in FIG. 33. More particularly, infliximab was superimposed with trastuzumab using crystal structures in which infliximab is bound to TNF (PDB ID: 4G3Y) and trastuzumab is bound by Protein A and Protein L (PDB ID: 4HKZ). Once superimposed, trastuzumab was removed leaving infliximab, Protein A, Protein L, and TNF in their expected positions within the complex. The distance from the N-terminus of Protein A to the N-terminus of TNF was estimated to be 40 Å as shown in FIG. 32. The distance from the N-terminus and C-terminus of Protein L to the C-terminus of TNF were estimated to be 50.7 Å and 61.9 Å, respectively, as shown in FIG. 33.

Figure 34:
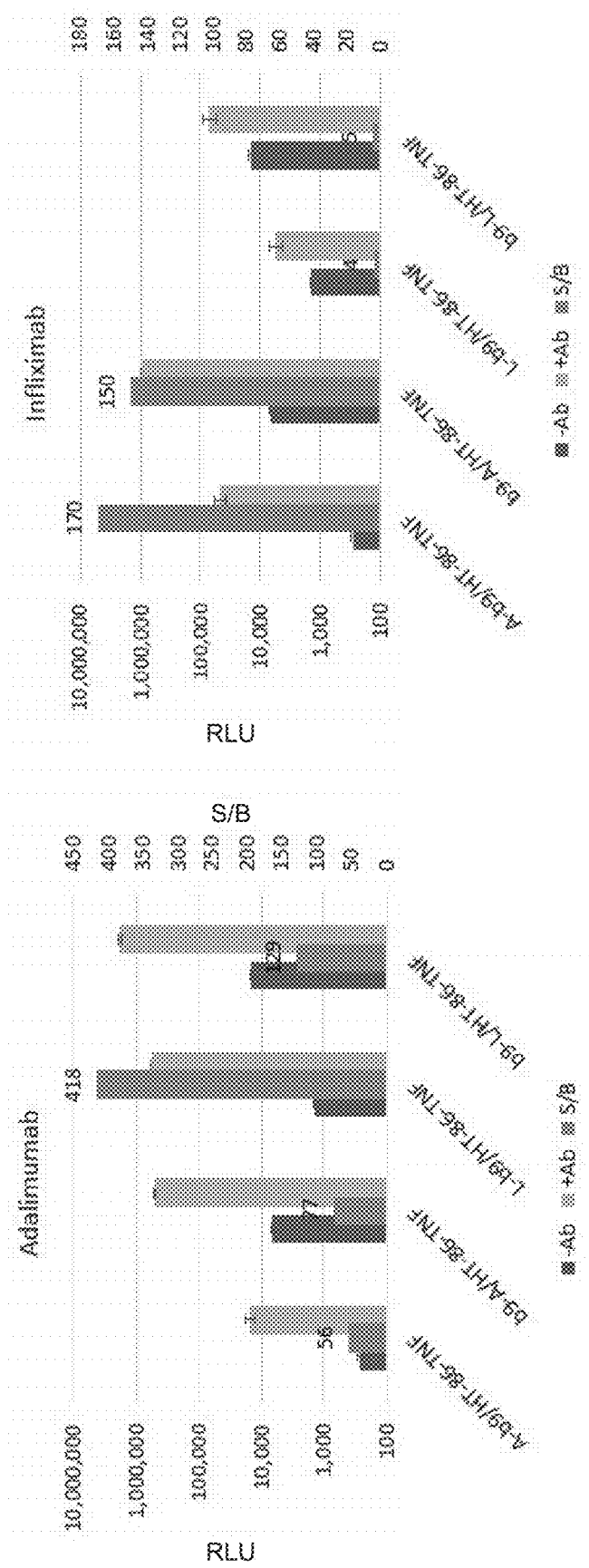
FIG. 34 is a bar chart showing both luminescence and the signal-to-background ratio for various split enzyme reporter systems.

A lysate of HaloTag®-β10*-TNF was tested combination with β9 at the N- and C-terminus of Protein A and Protein L. The luminescence in the absence of antibody (−Ab) or presence of 10 µg/mL antibody (+Ab) is shown (FIG. 34; left y-axis) as well as the signal-to-background ratio (FIG. 34; +Ab signal divided by −Ab signal; right y-axis). Values shown are the averages from three replicate measurement±standard deviation.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Each of the references cited herein is hereby incorporated by reference in its entirety. Further, reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A method for detecting an analyte that is configured to selectively bind to tumor necrosis factor (TNF), the method comprising:
    delivering a first agent into a vessel, wherein the first agent comprises (1) a first targeting domain for binding to the analyte that is configured to selectively bind to TNF, and (2) a first peptide fragment of a split reporter protein;
    delivering a second agent into the vessel, wherein the second agent comprises (1) a second targeting domain for binding to the analyte that is configured to selectively bind to TNF and (2) a second peptide fragment of the split reporter protein; and
    delivering a third agent into the vessel, wherein the third agent comprises a third fragment of the split reporter protein;
    wherein the first targeting domain is configured to selectively bind to a first target region of the analyte that is configured to selectively bind to TNF and the second targeting domain is configured to selectively bind to a second target region of the analyte that is configured to selectively bind to TNF, and the first and second target regions of the analyte that is configured to selectively bind to TNF are different from one another; and
    wherein the third agent binds to the first and second agents to form an active reporter complex.

2. The method of claim 1, wherein the analyte is an anti-TNF antibody or a portion thereof.

3. The method of claim 2, wherein the anti-TNF antibody or portion thereof is selected from the group consisting of infliximab, adalimumab, certolizumab pegol, golimumab, etanercept, or a pharmaceutical equivalent or pharmaceutical alternative thereof.

4. The method of claim 3, wherein the analyte is adalimumab.

5. The method of claim 3, wherein the analyte is infliximab.

6. The method of claim 3, wherein the analyte is selected from the group consisting of certolizumab pegol, golimumab, and etanercept.

7. The method of claim 1, wherein the first targeting domain comprises tumor necrosis factor or a portion thereof.

8. The method of claim 1, wherein the second targeting domain comprises an immunoglobulin-binding protein or a portion thereof.

9. The method of claim 1, wherein a biological sample is disposed within the vessel, and the method is designed to detect or quantify the analyte in the biological sample.

10. The method of claim 1, further comprising detecting a signal that is generated from a complex formed by the first agent, the second agent, and the third agent.

11. The method of claim 1, wherein the split reporter protein is a split enzyme.

12. The method of claim 1, wherein the split reporter protein is a beta-barrel protein.

13. The method of claim 1, wherein the split reporter protein is a dual-peptide activated luciferase.

14. A method for detecting human epidermal growth factor receptor 2 (HER2), the method comprising: delivering a first agent into a vessel, wherein the first agent comprises (1) a first targeting domain for binding to HER2 and (2) a first peptide fragment of a split reporter protein; delivering a second agent into the vessel, wherein the second agent comprises (1) a second targeting domain for binding to HER2 and (2) a second peptide fragment of the split reporter protein; and delivering a third agent into the vessel, wherein the third agent comprises a third fragment of the split reporter protein; wherein both the first targeting domain and the second targeting domain are configured to selectively bind to HER2, and the first and second targeting domains are different from one another and bind different sites on HER2; and wherein the third agent binds to the first and second agents to form an active reporter complex.

15. The method of claim 14, further comprising detecting a signal that is generated from a complex formed by the first agent, the second agent, and the third agent.

16. The method of claim 14, wherein the split reporter protein is a dual-peptide activated luciferase.

17. A method for detecting an immunoglobulin (Ig) or a fragment or portion thereof, the method comprising: delivering a first agent into a vessel, wherein the first agent comprises (1) a first targeting domain for binding to Ig and (2) a first peptide fragment of a split reporter protein; delivering a second agent into the vessel, wherein the second agent comprises (1) a second targeting domain for binding to Ig and (2) a second peptide fragment of the split reporter protein; and delivering a third agent into the vessel, wherein the third agent comprises a third fragment of the split reporter protein; wherein the first targeting domain is configured to selectively bind to a first target region of Ig and the second targeting domain is configured to selectively bind to a second target region of Ig, and the first and second targeting domains are different from one another and bind different sites on Ig; and wherein the third agent binds to the first and second agents to form an active reporter complex.

18. The method of claim 17, wherein the first targeting domain is selected from the group consisting of protein A, protein L, protein G, and protein A/G, or a portion thereof.

19. A method for detecting an analyte that is configured to selectively bind to acetylcholine receptor, the method comprising:

delivering a first agent into a vessel, wherein the first agent comprises (1) a first targeting domain for binding to the analyte that is configured to selectively bind to acetylcholine receptor, and (2) a first peptide fragment of a split reporter protein;

delivering a second agent into the vessel, wherein the second agent comprises (1) a second targeting domain for binding to the analyte that is configured to selectively bind to acetylcholine receptor and (2) a second peptide fragment of the split reporter protein; and delivering a third agent into the vessel, wherein the third agent comprises a third fragment of the split reporter protein;

wherein the first targeting domain is configured to selectively bind to a first target region of the analyte that is configured to selectively bind to acetylcholine receptor and the second targeting domain is configured to selectively bind to a second target region of the analyte that is configured to selectively bind to acetylcholine receptor, and the first and second target regions of the analyte that is configured to selectively bind to acetylcholine receptor are different from one another; and wherein the third agent binds to the first and second agents to form an active reporter complex.

20. The method of claim 19, wherein the analyte is an anti-acetylcholine receptor antibody or a portion thereof.

* * * * *